(12) United States Patent
Pamer et al.

(10) Patent No.: US 12,257,284 B2
(45) Date of Patent: *Mar. 25, 2025

(54) LANTIBIOTICS, LANTIBIOTIC-PRODUCING BACTERIA, COMPOSITIONS AND METHODS OF PRODUCTION AND USE THEREOF

(71) Applicant: MEMORIAL SLOAN-KETTERING CANCER CENTER, New York, NY (US)

(72) Inventors: Eric Pamer, Montclair, NJ (US); Sohn Kim, New York, NY (US); Peter McKenney, New York, NY (US); Silvia Caballero, Cambridge, MA (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/563,772

(22) Filed: Dec. 28, 2021

(65) Prior Publication Data

US 2022/0370547 A1 Nov. 24, 2022

Related U.S. Application Data

(63) Continuation of application No. 16/659,199, filed on Oct. 21, 2019, now Pat. No. 11,207,374, which is a continuation of application No. PCT/US2018/028629, filed on Apr. 20, 2018.

(60) Provisional application No. 62/488,480, filed on Apr. 21, 2017.

(51) Int. Cl.

| | | |
|---|---|---|
| *A61K 38/00* | (2006.01) | |
| *A61K 38/12* | (2006.01) | |
| *A61K 38/44* | (2006.01) | |
| *A61P 31/04* | (2006.01) | |
| *C12N 1/20* | (2006.01) | |
| *C12P 21/00* | (2006.01) | |

(52) U.S. Cl.
CPC .......... *A61K 38/12* (2013.01); *A61K 38/443* (2013.01); *A61P 31/04* (2018.01); *C12N 1/20* (2013.01); *C12P 21/00* (2013.01); *C12Y 101/0112* (2013.01)

(58) Field of Classification Search
None
See application file for complete search history.

(56) References Cited

U.S. PATENT DOCUMENTS

| | | | |
|---|---|---|---|
| 8,299,020 B2 | 10/2012 | Yousef et al. | |
| 11,207,374 B2* | 12/2021 | Pamer | A61K 38/12 |
| 2002/0128186 A1 | 9/2002 | Hillman | |
| 2007/0037963 A1 | 2/2007 | Hillman et al. | |
| 2010/0041613 A1 | 2/2010 | Coleman et al. | |
| 2011/0150917 A1 | 6/2011 | Hancock et al. | |
| 2017/0087196 A1 | 3/2017 | Pamer et al. | |
| 2022/0096567 A1* | 3/2022 | Pamer | A61K 9/0031 |

FOREIGN PATENT DOCUMENTS

| | | |
|---|---|---|
| WO | WO 2009/135945 A1 | 11/2009 |
| WO | WO 2015/077794 A1 | 5/2015 |
| WO | WO 2017/091753 A1 | 6/2017 |

OTHER PUBLICATIONS

Semantic scholar. Accessed Aug. 19, 2020 at https://www.semanticscholar.org/topic/Blautia-producta/647602 (Year: 2020).*
Kitagawa et al. Nisin, a food preservative produced by Lactococcus lactis, affects the localization pattern of intermediate filament protein in HaCaT cells. (2017). Anatomical Science International (2019) 94:163-171 (Year: 2017).*
Ridlon et al. Clostridium scindens : a human gut microbe with a high potential to convert glucocorticoids into androgens (2013). Journal of Lipid Research vol. 54, 2013 (Year: 2013).*
U.S. Appl. No. 16/659,199 (U.S. Pat. No. 11,207,374), filed Oct. 21, 2019 (Dec. 28, 2021).
U.S. Appl. No. 16/659,199, filed Nov. 24, 2021 Issue Fee Payment.
U.S. Appl. No. 16/659,199, filed Aug. 25, 2021 Notice of Allowance.
U.S. Appl. No. 16/659,199, filed Jul. 20, 2021 Request for Continued Examination (RCE).
U.S. Appl. No. 16/659,199, filed Apr. 21, 2021 Notice of Allowance.
U.S. Appl. No. 16/659,199, filed Feb. 18, 2021 Response to Non-Final Office Action.
U.S. Appl. No. 16/659,199, filed Aug. 28, 2020 Non-Final Office Action.
U.S. Appl. No. 16/659,199, filed Jul. 10, 2020 Response to Restriction Requirement.
U.S. Appl. No. 16/659,199, filed May 22, 2020 Restriction Requirement.
Begley et al., "Bile Salt Hydrolase Activity in Probiotics," Appl Environ Microbiol. 72(3):1729-1738 (2006).
Buffie et al., "Microbiota-mediated colonization resistance against intestinal pathogens," Nature Reviews Immunology 13:790-801 (2013).
Buffie et al., "Precision microbiome reconstitution restores bile acid mediated resistance to Clostridium difficile," HHS Public Access Author Manuscript, 517(7533):1-25 (2015).

(Continued)

*Primary Examiner* — Aradhana Sasan
*Assistant Examiner* — Mercy H Sabila
(74) *Attorney, Agent, or Firm* — Baker Botts L.L.P.

(57) ABSTRACT

The present disclosure relates to novel lantibiotics, lantibiotic pharmaceutical compositions, isolated and recombinant lantibiotic-producing bacteria, bacterial pharmaceutical compositions, methods of producing novel lantibiotics from lantibiotic-producing bacteria, and methods of using such lantibiotics, lantibiotic pharmaceutical compositions, and bacterial pharmaceutical compositions to treat gram-positive bacteria infections, including vancomycin resistant enterococci infections, in patients, and to treat food and other objects to avoid gram-positive bacteria contamination.

20 Claims, 33 Drawing Sheets

Specification includes a Sequence Listing.

(56) References Cited

OTHER PUBLICATIONS

Caballero et al., "Cooperating Commensals Restore Colonization Resistance to Vancomycin-Resistant Enterococcus faecium," Cell Host & Microbe 21(5):592-602 (2017).
Cheigh et al., "Simple one-step purification of nisin Z from unclarified culture broth of *Lactococcus lactis* subsp. lactis A164 using expanded bed ion exchange chromatography," Biotechnol Letters 26:1341-1345 (2004).
Database EMBL [Online] Jul. 22, 2016 (Jul. 22, 2016), "*Blautia* sp. YL58, complete genome," XP55758007, retrieved from EBI accession No. EMBL: CP015405 Database accession No. CP015405 * sequence *.
Database UniProt [Online] Nov. 30, 2016 (Nov. 30, 2016), "SubName: Full=Lantibiotic nisin-A {ECO:0000313 I EMBL:ANU75750. 1};", XP55756681, retrieved from EBI accession No. UniProt:AOA1C7I7X6 Database accession No. AOA1C7I7X6.
Extended European Search Report dated Apr. 29, 2021 in Application No. EP18787096.
Ezaki et al., "16S Ribosomal DNA Sequences of Anaerobic Cocci and Proposal of *Ruminococcus hansenii* comb. nov. and *Ruminococcus productus* comb. nov.," Int J Syst Bacteriol. 44:130-136 (1994).
International Search Report mailed Aug. 7, 2018 in International Application No. PCT/US2018/028629.
Kim et al., "Microbiota-derived lantibiotic restores resistance against vancomycin-resistant Enterococcus," Nature 572(7771):665-669 (2019).
Kitagawa et al., "Nisin, a food preservative produced by *Lactococcus lactis*, affects the localization pattern of intermediate filament protein in HaCaT cells," Anatomical Science International 94:163-171 (2019).
Kluskens et al., "Post-translational modification of therapeutic peptides by NisB, the dehydratase of the lantibiotic nisin," Biochemistry 44(38):12827-12834 (2005).
Krafft et al., "Purification and Characterization of a Novel Form of 20α-Hydroxysteroid Dehydrogenase from Clostridium scindens," J Bacteriol. 171(6):2925-2932 (1989).
Liu et al., "Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces," Int. J. Syst. Evol. Microbiol., 58:1896-1902 (2008).
Lubelski et al., "Directionality and Coordination of Dehydration and Ring Formation during Biosynthesis of the Lantibiotic Nisin," J Biol Chem 284(38):25962-25972 (2009).
McAuliffe et al., "Genetic Analysis of Two Bile Salt Hydrolase Activities in Lactobacillus acidophilus NCFM," Appl Environ Microbiol. 71(8):4925-4929 (2005).
McAuliffe et al., "Lantibiotics: structure, biosynthesis and mode of action," FEMS Microbiology Reviews 25:285-308 (2001).
Morris et al., "*Clostridium scindens* sp. nov., a Human Intestinal Bacterium with Desmolytic Activity on Corticoids," Int J Syst Bacteriology 35(4):478-481 (1985).
Mulders et al., "Identification and characterization of the lantibiotic nisin Z, a natural nisin variant," Eur. J. Biochem. 201:581-584 (1991).
Partial Supplementary European Search Report dated Dec. 18, 2020 in Application No. EP 18787096.
Ridlon et al. Clostridium scindens : a human gut microbe with a high potential to convert glucocorticoids into androgens (2013). Journal of Lipid Research vol. 54, 2013.
Ridlon et al., "Bile salt biotransformations by human intestinal bacteria," J Lipid Res 47:241-259 (2006).
Ridlon et al., "Identification and characterization of two bile acid coenzyme A transferases from Clostridium scindens, a bile acid 7α-dehydroxylating intestinal bacterium," J. Lipid Res. 53:66-76 (2012).
Rink et al., "Dissection and Modulation of the Four Distinct Activities of Nisin by Mutagenesis of Rings A and B and by C-Terminal Truncation," Appl Environ Microbiol 73(18):5809-5816 (2007).
Semantic scholar. Accessed Aug. 19, 2020 at https://www.semanticscholar.org/topic/Blautia-producta/647602 (2020).
Suarez et al., "One-Step Purification of Nisin A by Immunoaffinity Chromatography," Appl Environ Microbiol 63(12):4990-4992 (1997).
Uteng et al., "Rapid Two-Step Procedure for Large-Scale Purification of Pediocin-Like Bacteriocins and Other Cationic Antimicrobial Peptides from Complex Culture Medium," Appl Environ Microbiol 68(2):952-956 (2002).

* cited by examiner

```
                          SEQUENCE LISTING

<160> NUMBER OF SEQ ID NOS: 21

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ile Thr Ser Lys Ser Leu Cys Thr Pro Gly Cys Val Thr Gly Ile Leu
1               5                   10                  15

Met Thr Cys Pro Val Gln Thr Ala Thr Cys Gly Cys Gln Ile Thr Gly
            20                  25                  30

Lys

<210> SEQ ID NO 2
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Lys Phe Asp Asp Phe Asp Leu Asp Val Thr Lys Thr Ala Ala
1               5                   10                  15

Gly Glu Gly Gly Val Glu Pro Arg Ile Thr Ser Lys Ser Leu Cys Thr
            20                  25                  30

Pro Gly Cys Val Thr Gly Ile Leu Met Thr Cys Pro Val Gln Thr Ala
        35                  40                  45

Thr Cys Gly Cys Gln Ile Thr Gly Lys
    50                  55

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Dehydrobutyrine
<220> FEATURE:
```

```
<221> NAME/KEY: MOD_RES
<222> LOCATION: (3)..(3)
<223> OTHER INFORMATION: Dehydroalanine
<220> FEATURE:
<221> NAME/KEY: MOD_RES
<222> LOCATION: (5)..(5)
<223> OTHER INFORMATION: Dehydroalanine
<220> FEATURE:
<221> NAME/KEY: MOD_RES
<222> LOCATION: (8)..(8)
<223> OTHER INFORMATION: Dehydrobutyrine
<220> FEATURE:
<221> NAME/KEY: MOD_RES
<222> LOCATION: (13)..(13)
<223> OTHER INFORMATION: Dehydrobutyrine
<220> FEATURE:
<221> NAME/KEY: MOD_RES
<222> LOCATION: (21)..(21)
<223> OTHER INFORMATION: Dehydrobutyrine
<220> FEATURE:
<221> NAME/KEY: MOD_RES
<222> LOCATION: (26)..(26)
<223> OTHER INFORMATION: Dehydrobutyrine
<220> FEATURE:
<221> NAME/KEY: MOD_RES
<222> LOCATION: (31)..(31)
<223> OTHER INFORMATION: Dehydrobutyrine
<220> FEATURE:
<221> NAME/KEY: MOD_RES
<222> LOCATION: (33)..(33)
<223> OTHER INFORMATION: Dehydrobutyrine
<220> FEATURE:
<221> NAME/KEY: MOD_RES
<222> LOCATION: (39)..(39)
<223> OTHER INFORMATION: Dehydrobutyrine

<400> SEQUENCE: 3

Ile Xaa Xaa Ile Xaa Leu Ala Xaa Pro Gly Ala Lys Xaa Gly Ala Leu
1               5                   10                  15

Met Gly Ala Val Xaa Gly Ile Leu Met Xaa Ala Pro Val Gln Xaa Ala
            20                  25                  30

Xaa Ala Gly Ala Gln Ile Xaa Gly Lys
        35                  40

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Dehydrobutyrine
<220> FEATURE:
<221> NAME/KEY: MOD_RES
<222> LOCATION: (3)..(3)
<223> OTHER INFORMATION: Meso-lanthionine
<220> FEATURE:
<221> NAME/KEY: MOD_RES
<222> LOCATION: (5)..(5)
<223> OTHER INFORMATION: Dehydroalanine
<220> FEATURE:
<221> NAME/KEY: MOD_RES
<222> LOCATION: (8)..(8)
<223> OTHER INFORMATION: Threo-beta-lanthionine
<220> FEATURE:
<221> NAME/KEY: MOD_RES
<222> LOCATION: (13)..(13)
<223> OTHER INFORMATION: Threo-beta-lanthionine
<220> FEATURE:
<221> NAME/KEY: MOD_RES
<222> LOCATION: (18)..(18)
<223> OTHER INFORMATION: Dehydrobutyrine
```

```
<220> FEATURE:
<221> NAME/KEY: MOD_RES
<222> LOCATION: (23)..(23)
<223> OTHER INFORMATION: Threo-beta-lanthionine
<220> FEATURE:
<221> NAME/KEY: MOD_RES
<222> LOCATION: (25)..(25)
<223> OTHER INFORMATION: Threo-beta-lanthionine
<220> FEATURE:
<221> NAME/KEY: MOD_RES
<222> LOCATION: (31)..(31)
<223> OTHER INFORMATION: Dehydrobutyrine

<400> SEQUENCE: 4

Ile Xaa Xaa Lys Xaa Leu Ala Xaa Pro Gly Ala Val Xaa Gly Ile Leu
1               5                   10                  15

Met Xaa Ala Pro Val Gln Xaa Ala Xaa Ala Gly Ala Gln Ile Xaa Gly
            20                  25                  30

Lys

<210> SEQ ID NO 5
<211> LENGTH: 174
<212> TYPE: DNA
<213> ORGANISM: Brachycybe producta

<400> SEQUENCE: 5
atggcaaaat tgatgatttt cgatctggat gtaacaaaga cagcagcagg ggaaggcgga      60
gtagaaccgc gaatcacaag taagtccctg tgtacaccgg gttgtgtgac gggaatcctg     120
atgacctgcc cggttcagac agcaacctgc ggatgccaga ttactggtaa ataa           174

<210> SEQ ID NO 6
<211> LENGTH: 666
<212> TYPE: DNA
<213> ORGANISM: Brachycybe producta

<400> SEQUENCE: 6
atgtcaaaaa tacttgttat tgatgatgat aaaaaaatac tggaattagt atatgaggta      60
ttgatgcgag aagggtacga tgtagaaaca aaagagtata ttgaaaatat aaatatagcg     120
gaatttgaaa aattcgatct catttttactt gatattatga tgccagtatt tgatggattt     180
gaaatcctaa aaaaaataaa gtgtattatt tcgtgcccag taattttttct ttccgcaaaa    240 tctagcgaag atgcaaaggt aaaggattg atggaaggcg cggatgatta taacaaag       300 ccatttagca taaagaatt ggtggctaga ataaagttg cgctaagaag aaatacgaat       360
attaaagaag ataagtaga agttgatgga ttagtatttg atttaaatac aaattctatt     420
gcactagata taaaactat tatcttgact aagaatgaat ttagaatatg taaaattctt     480
gtacaaaatc aagggcaaac tttttcaaag gatatgttat atgatttttt atatgatttg     540
gatacggata ctcaattaag aacaatcacg gaatacattt attcaatacg gaagaaattc     600
aaacgttttg aaaagatcc aataaaaact gtatggggga ttggttatag atggtgcata     660
gattaa                                                                666

<210> SEQ ID NO 7
<211> LENGTH: 1374
<212> TYPE: DNA
<213> ORGANISM: Brachycybe producta

<400> SEQUENCE: 7
atggtgcata gattaatacc tatgaagaaa cagttaatgt tctatatatt acagttagta      60
```

| | | | | |
|---|---|---|---|---|
| ttaggattgg | taatagtagg | tatgggatgg | ctatttatca | caaatatatt gatatgtgcc | 120 |
| aagatagtta | ttcctgcaaa | ttatagtgaa | aatatattaa | aagaaaatag tgctaaatta | 180 |
| tcaactttgg | ataaagttac | atcagatttt | ttgccaatcg | gatgcgaatt tgctgtattt | 240 |
| gattttaata | ataataaaaa | atatggaaat | atgagttcga | ttaatgaaca acatgctttg | 300 |
| aacgttattc | ttggaaacga | gaataatatc | caaggaaata | agatttattc agtgatattt | 360 |
| agggaaaaag | aaatttgtgt | agttaaatat | aaatatgcgac | cttatttcaa tttgacgaaa | 420 |
| agaaatttgc | aacttcccaa | ttacgatatt | atttcctatg | cagttatgct aatagtgtat | 480 |
| gttatatatg | tttatatttc | tacattcagg | ctagtaaaaa | attggggaaa ggagtttgaa | 540 |
| aaaatcaaaa | aaataacttt | agagattgaa | aatgggaatt | tagattttga atattgttct | 600 |
| agtaaagtaa | aagagttttc | taacgctata | gattccttaa | taagaatgag atgctttta | 660 |
| aaagatacat | tatattcgaa | ttggaaaatg | gaatatgaaa | aaaatgaaga dataggtgcc | 720 |
| ttggcacatg | atattaaaat | tccattaact | attattaagg | gaaatacgga attagtatta | 780 |
| gattacaatt | ctgattcata | caattttta | catttgagaa | atgtgctaga ggcggctgaa | 840 |
| aaaatagaaa | aatatcttgt | agtgcttctt | caatatgtca | aagctaaaaa aatagaaaat | 900 |
| aataaaaggg | aacgaattga | ttgcgatacg | ttttccgaaa | ggatttgtct tgaagtgaaa | 960 |
| aagtacacag | ctaatttaca | tacaaaattt | gaattttcag | ttgaccatgt tagcggcatg | 1020 |
| atttatatag | attactttc | tatagaaagg | gccatattta | atatcataga taatgcgatt | 1080 |
| gagtataaag | tcgaagatga | taagatttta | tgtcatacga | tgctagagga tggaatgtat | 1140 |
| actatttctg | tatcaaatag | ttgtggacaa | tttgacaagg | aagttttagc gaatgctact | 1200 |
| aaattatttt | atacatcaga | taaaaataga | aatacattac | actacggaat tggattggca | 1260 |
| tatgtacaaa | gagtcgttga | aacgaacaat | ggatatatga | gtatatttaa ttcagataaa | 1320 |
| ttgggtgcga | cagtaaaaat | tcagttaccg | ataatatcaa | aagaaaatag ttga | 1374 |

<210> SEQ ID NO 8
<211> LENGTH: 3066
<212> TYPE: DNA
<213> ORGANISM: Brachycybe producta

<400> SEQUENCE: 8

| | | | | |
|---|---|---|---|---|
| atgaaaaaat | tattttatga | cattggagaa | tttatgtatc | gcagaccgac tgagtataag | 60 |
| tctcaaattg | acttttccga | acatgaggtt | aagttaatat | gtagcaatcc tgcatttagg | 120 |
| gaaaaagtaa | atattgcaag | tccttcattg | gtggaaatga | tggatatata tatgaaaaat | 180 |
| cctaaacaat | tatcagaaaa | gaaatcaaat | ggattaaata | tttctttatt gaaatattta | 240 |
| atccggagta | agaaaggac | tactccgttt | ggcttgttta | caggtgttgg aactggctgc | 300 |
| tttagcaaaa | gtgaaaaatt | ccccatattg | atgacgaaga | cagaaaaaaa agttaatgtt | 360 |
| gattctgaat | ggttatttgg | actagtaaat | attgtagaaa | aaattatgc tgagaaattg | 420 |
| gaatttaagt | ttaatgacgc | atgttatata | aaaggcaata | gagttatatt agtatactca | 480 |
| actgaaaaag | atgcagaaga | aatcagtatt | cgatttacaa | aagtttttaa ggtacttttt | 540 |
| gataaaatta | aggattacga | aagatatgaa | aaattcattg | aaatacttag ttctgaatat | 600 |
| ccgagtactt | caatgaagaa | atcaaattg | tatataaatg | aactgatttc taaaggtttt | 660 |
| ttgatttcta | atttgagacc | atcgtttagc | aatgcagatc | cgctaatgta ctttatcaag | 720 |
| cagtgtgagc | gaatgaaaat | tacagatata | tgtgaaaagg | ctaatgaaat atataaaatg | 780 |
| tgtgaggatt | atagcaaaac | agatattggt | aatgggataa | ttaagtataa tgcgataaaa | 840 |

-continued

```
acaaaaatgc agacattata taaatgctca tcatatttac aagtggatac tgttataggt      900
ggaggcgact ttcaacttaa tcaagacatt tccaaggcaa tatgtgaagt ggcaagtcta      960
tttgtgtatc ttagtaatag tcctaagaaa caacatggtt atttagaaca ttatagaaat     1020
aaatttattg aaaaatatgg aatagatcgg gaagtacctt tattggaaat gattgattct     1080
agtaatggta ttggagctcc aacaccatac ttaaagccac aaaatgattt ttacgatgag     1140
tacaatacaa aagacaatta taaatatgaa ctaaaaaatt attttttggt ggagtatgaa     1200
aaagctttgg ctaataattc atacattgat attaatatgg agactcttca aaaaataaca     1260
gattgtaccg tgcaagaaga agaaatccct atttctttag aattatattt tattttgaaa     1320
gtagaagatg gaaaagtgag tcttaatcta agtcctaatt gtggctcatt tgtggcaggt     1380
aaaacttttg gtaggttctc cgtacagtct gacaattttg caaatgtttt aaagaaatgt     1440
aacaaagaag aaagaaaaat tcgtagtccg catagtgaaa tttgtgaaat aagttttttg     1500
ccttctccaa cgagaaatgg aaatattgta agaacattat cgtttagaga aaagaaact      1560 gccgttttta cctgtggcag caaggataaa aaagacattg ttagtcttaa tgatatttat     1620
ataggaatat ttaacgaaaa gttttatgca agggataaaa agactgggaa actgattatt     1680
ttcgaatcaa acaatatgta taatccgatg cttaatccca atgttttag gttttttgcag     1740 gatatttctt atgaaggaaa aagggagtgg tctgagttcc catggagtta tatctatgca     1800
gatttgagac atattccaac aataaagtat aaaggaattg tactccaaaa tgaaaaatgg     1860
aaagttaata tacaagaact tgaattactc aaaaaggatt ttgaaagttt taagaaaaaa     1920
tttttagcat tgattattgg ccgcaacatg cctttgaata tttatattgt tgatgcagat     1980
aaccgtatta gacttaatct ggcaacagat ttatcgatgc ggattgttta tgacgaattt     2040
aagaagcata aggatagtga tttggttttt gaaaaagtag aaaatggttc agatattatt     2100
tatgatgatg ggaaaacgta tgcaacggaa atagttgttc cgcttttcag gaaaaataaa     2160
gaagaactat cattaattcc attatcccaa aagacgtata ccagagagca gcatatgatt     2220
ttgccattta taactggct ttatttaaaa ttgtattgta atgagaatcg agaggaggaa      2280
ttaattgcat tttatattat ggattttat gaatcattaa aggaaaaata tggtatttca      2340
tatttttata tgcgttatgc tgatccgaag ccacatataa gattgcgatt acatgcaaca     2400
agagaattgc tattgcaagt ctatccacaa atcttgaaat ggtactcaga attgttctca     2460
gatcagatag taggggatat gactatttct gtatatgatc gagaaattga agatatgga      2520 ggggcattgt tgatggatac tgcggaaaag gtattttttg aagatagtta tattgttgaa     2580
aacatactgc gtttaaaacg tttggggaaa atatctttaa atttggatga tgttgctgtt     2640
gtttccatca taatgtatgt ttcgcagttc tataataaat atgaagagca attgcagttt     2700
ttgtcaatca attatcattc ttccgatttt ataagcgaat tcaagaagaa aaagataat      2760 ctattaagaa tttgcgatat tgaaaatgaa tggaataatc taaatagcat gaaagacggt     2820
aaagttgttt atgaacttat gtggcgaaga tgtaaagtaa ttagcgagta tagtgaaaaa     2880
attaggaaga ttaatccaga tccgatgttt aaaaatagta ttgttgcaag tgttattcat     2940
ttacattgca atagattgat tggtacaaat cgtgaattag aaaggaagct gatggcatt      3000 gcagaaagtg tgttatatgc aaaaaaatat gtaatgagaa ggattgaagt caatggaaag     3060
aaatag                                                                3066
```

<210> SEQ ID NO 9

<211> LENGTH: 1806
<212> TYPE: DNA
<213> ORGANISM: Brachycybe producta

<400> SEQUENCE: 9

```
atggaaagaa atagaattgg aatcaaagat atactaatag ctttaaaaca attacctaaa      60
acggtttcta ttattatgca tgtaagtaag ggattgtttt ttcttattat attatttagt     120
gtggttgctg gagtttttcc ggtaattaca ctgattcttt cccaagaatt gattaattgt     180
cttgtgcaag ggaaaaactt ttttgatggt acatttataa tgtttgtatt atatttgctt     240
gcatcatttg ccggagaact aattattgaa gcaaaaggat ttatagaggg aaaatttcaa     300
tatttgttac agtatcgctt gaattatctg gttatggaaa aatgtacgga tctatctttg     360
gaagattttg aaaactctga atgtatgac agaatcgaaa aataacagg ggaaattgca      420
tatagaccat ttcagatttt tctggcgatt attaatcttt tgacatctgc gattactatg     480
atatcgtccg ctattttgct ttttagctgg aatccttata tatcaattgt tttattggtt     540
gttcctattg tttcagtact atattttttg aaaataggtc agcaggagtt tgatattata     600
tggaatcgtg caaagacga agaaagact tggtatttaa gctatttatt gacacatgat      660
ttttcttaca aggaaatatc tttattaaat ataaagact atcttttagg aaatttcata      720
aaaataagta atcgttttat tgaacaaaat atcaaaatct taaaaagaa aacagtattt      780
aacattatct atgagatgat catgcaagta gtaagtggct tgattattgg tgaggcaatt     840
atatcggcat acgcagggga tattcttgtt ggaaacgtta tgagctatat acggagcgtg     900
ggattagttc agagcaattc acaggctatt atggcaaata tctataccat atataatagc     960
tcattatata tggatatgtt atttgagttt ttgaaatatt gtggaaaagg taagattact    1020
gggaatatga aaaaaattga aggtgagatt acaacgatag atataaaaaa tctctctttc    1080
tcttataaaa ataaaaaga gacgttgaaa gatattagca tcagttttca aaaagggag      1140
aaaattgcat tagtaggtcc taatggctct gggaaaagta cattaattaa aatttaagt    1200
ggattatatg agattaagta tggcgaaatt ttgattaatg gcataccatct aaagaaaatt    1260
gatattgaag attatcatac gaaaatgtca gtactatttc aggactttgt aaaatatgaa    1320
ctcacattga aggaaaatat aggattgga gatataaagg aatttaattc aactgataga    1380
atgaaagaaa ttcttgataa acttcaaaca aagtttctaa aaaagatggt gaatatgat     1440
ttcgatatgc agcttggaaa ttggtttgat gatggacagc agttatcaca aggacaatgg    1500
caaaaagtgg cacttgcgcg agcatatttt aagaacgcat caatttatat cttgatgag    1560
ccgaatgctg cgcttgatac agtttctgaa cgggaaattt ttgatgattt ttttgaaata    1620
tcaaaggaa aaataggaat ttttatatca catcgactta atgcggcaaa aaaggcagac    1680
aaaataattg ttatggatga tggaagagtt gttggaatgg gtaaacatga agacttacta    1740
aaaaattgtc ttgtatatca aactttatat caggctgaga catacgagaa tgaggaggat    1800
atgtaa                                                              1806
```

<210> SEQ ID NO 10
<211> LENGTH: 1323
<212> TYPE: DNA
<213> ORGANISM: Brachycybe producta

<400> SEQUENCE: 10

```
atggataaca gcataatttc tattgtaaaa gagattgcta gaaacttagg cgactatgat      60
aatgtaaaga ggattgtagc ggataaagac aatatacgag tgatgggaga atttaatttt    120
```

```
cagggatggg aaccacttac attaagtcat ggaataccag gaatctgttt gctatatggg      180
aaattaatgg aatgctttcc tgatgaggag atttgggctg aattagcaca tcagtatctt      240
ggttatttgg tgcaggaaat aaataaagag gggtttcaaa ccttgtcaat gtttcagga       300 acttctggta ttgggttggc tgttgcaagt gtttcaaata attttgtaa ctataataaa       360 ctgttaaata cgataaattc gtatataatt aattggtttg atgagtttat tgatagtatt      420
gatttaaaaa aagggactag aagtatctgt tatgatgtaa tagaaggctt gagtggtatt      480
ttgagttatt gttcaatata ctatgaacag gaatcctttt ctccgatatt acttaaaggc      540
ttgaaaaaat tagttgaact tacatatgat attgaagtaa aaggatacca tgtgcctgga      600
tggtatattc catcggataa tcagtttagt actgtagaaa aagagttata tccatatggt      660
aattttaata caagttttc tcatggaatt gcaggtccat taacactact ttcagaaatg       720
aaaagtaaag gatttatgat tgaaggacaa gaagaggcaa ttgaaaagat tgtaaaattt      780
ctatttgatt ttagatctaa cgatcaaaaa cgagattttt ggaaaggcca aattgacttc      840
catgaatata taaccggaaa agtgtcagaa aaaaatataa ttcgtcgaga tgcttggtgt      900
tatgaaaatc cggagtgtg ttattcactt attatggctg gcaatgcaat gaaaaaccaa       960
agttggatag attatggaat acataatatg aaaaagacat tgagcgatgt aaaaggtata     1020
ttttcaccta cattttgtca tggtttttct ggattgtatc aagttgttaa ttctatagaa     1080
tttactattg gaaaggacat ttttatagt gagaaaaaag aattgcttaa taaaattatg      1140 agttttatg actctaacta tatttttgga tttagaaata tggaggtagg tgatgagaat      1200
ggaaatataa gagcttttga acatttaggt ttattagatg gtacaattgg agtatgtctg     1260
gctcttttag aaggagagca taagacaaag aacatttgga aaagagcttt tttgttagca     1320
tag                                                                   1323
```

<210> SEQ ID NO 11
<211> LENGTH: 702
<212> TYPE: DNA
<213> ORGANISM: Brachycybe producta

<400> SEQUENCE: 11

```
atgaatatga ttttaaaaac aacaaatctc tgcaaatcat tcagcgggca gacagccgta       60
aataacatat cgctgaacat tgaaaaaat tccgtctatg gattgttagg accaaacgga       120
gccggaaaat ccacaacact caaaatgata acaggcattt tgaagcccac atctgggagc      180
attgagtttg acgccacgc atggaagcgg agcgacttaa accatattgg agcattgatt       240
gaaatgccgc cgctttatga gaatttaacc gcctatgaaa atctgaaagt taggtcaacc      300
cttttagggc tgcacagacaa taggattgag gaagtgcttc aaatcgtccg gctgacagaa      360
acaggcagaa aaagagccgg acagttttct cttggaatga gcagcggct tggaattgca      420 attgcattat taaatagtcc gaagctgctt attcttgacg agcctacaaa cggtcttgac      480
ccggtgggga ttgaagaact tagggagctt atccgttcat ttccggaaaa gggaattacc      540
gttattttat ccagtcatat tctttccgag gtacaacaga ccgccgatca tatcggcatt      600
attgcgggcg gtgtcttagg ctatgagggg agacttaatg cgaatgaaaa tttggaacgg      660 cttttatgg acgttgtgaa aagcaatcac agggagggct aa                          702
```

<210> SEQ ID NO 12
<211> LENGTH: 723
<212> TYPE: DNA

<213> ORGANISM: Brachycybe producta

<400> SEQUENCE: 12

| | | |
|---|---|---|
| atgaattact taaaatcaga gcatttgaaa ttcaaaagga caatatcaaa caagctgctt | 60 | |
| ttcatcattc cgctaatcac agctattttt gcatggatag tgggaggttt tatcgggttt | 120 | |
| caatatacaa cgctttactg gtggtatgcg ttcctgcttc cgggagcaat cgcaatctta | 180 | |
| tgttccttat cacaccggaa agaagaaagt gcggggaaat attattctgt attttctatg | 240 | |
| cccttgaacc tttcaaaatt tgaaatggca aaaggaatga ttttgattga aaagctgctt | 300 | |
| gtggcaggag tattttttagc attgcttatc tcaatcagca atatcatttc cccggcaaca | 360 | |
| gcggtatatt ctgttccgca gagtatggca ggcagtatag cgattgtgat agcgtccgtc | 420 | |
| tggcaaatcc cattgtgcct gtaccttgcg cgtaaaatag acttttttgt accgataatg | 480 | |
| ctaaatactg tacttgggat atttcttcct atcctgttag gaaacacagc cgtttggtgg | 540 | |
| ctcatgccgt attgtgggc ggcgaagctg gcggagccgc ttatggggat tgaattaaac | 600 | |
| ggaacttttg cgggaaattc cggttttttct tgtaccattt ttatctctgt cgcactatca | 660 | |
| atattcttat tcattgtctt atcttttgta gacgcgaagg actttgcaaa aggaggtaga | 720 | |
| taa | 723 | |

<210> SEQ ID NO 13
<211> LENGTH: 732
<212> TYPE: DNA
<213> ORGANISM: Brachycybe producta

<400> SEQUENCE: 13

| | | |
|---|---|---|
| atgggctttc ttggggcggt tcgttccgaa ctaataaaag taaagcatac gtcctttggg | 60 | |
| gtaattcatt tatgcgtacc tgttcttggg gcgttactgt ttattgttta ctatgtccta | 120 | |
| tatggaaaca cagcggatta caaaaaacta aaatgatat tagagcttac ggcgactatt | 180 | |
| ttccctttgc tgataagtgt tgttgtgagc ttgaatgtct tattgaaga aaaggcttca | 240 | |
| cactttcaaa tattgctcgg agtgcctaac cggtataaag ttgtactgac aaaattagcc | 300 | |
| gttttatatg gagcaggaat aaccgcgctg ttttgtctat ccttgtcttt ctgctcggc | 360 | |
| gttcatttttt tgagaataga tgataccgta caacttagta tgttagtcaa agcagccgca | 420 | |
| ggaatggcat tttgtaattt aattatttat gcgctgcact tattccttag ctttcgattt | 480 | |
| ggactgggta tctcattgtt ttggggagta tttgaaagtc tgcaatgtat tctatacagt | 540 | |
| aatatcgaat aaaaggtgt agggcgatat atccccttg catggtctat gaactgggtg | 600 | |
| catgatgtta tgaacaacgt gctgtccact catgggacag aatggatagg aattgctgta | 660 | |
| ttgacaatgg gcggtgtatt attaacttta ctatggtttt ctcattggga gggacgaaaa | 720 | |
| aattatgaat aa | 732 | |

<210> SEQ ID NO 14
<211> LENGTH: 816
<212> TYPE: DNA
<213> ORGANISM: Brachycybe producta

<400> SEQUENCE: 14

| | | |
|---|---|---|
| atgaataaaa acaaaaaaat agttatattt ctgctgtttta cctttatcgt ttgtgtggct | 60 | |
| cttgcaggct gttctttaca ggacagaatc gaagaatatt ccagtgacaa agaacaatgc | 120 | |
| tatttgaata cggaaagcgt aacacgtttt tcctataagg gtaacgatta caccattttg | 180 | |
| gcagataccg tatcaaatgg tgggcttgga gaatggattg gatatatccg gcagcttgcc | 240 | |

```
gccatagatg agaacggaaa aatattgctg caagaaaatg ttgaaacggc gacttttcaa      300
tccttagcgg atttggcaga gaaagcacca gaagcctctt acattattcc gtttctcaat      360
gtatatgcag cacctaacgc agacgattat ctgattgtag atgtaaacgg agggtatcat      420
aaagctgtta tcagcgagaa tatcaaggat agcgatactg ttttttgattt taaggaaaca      480 gaaaaatcta taaacggcag ctttgaaatc aatccagaaa atgcgacaca gcttctttgt      540
ggcgggacgg tttatcaagt aacgtctgaa atggtatctg atgataaatt aggcagctac      600
attgatattc ttgcagaaag tgttacattt gacacagaaa cgaaaatccc tttgtcaaag      660
gaagatttaa gcaatgttga ctggtacggg gagaataccg gacaggggcg ggagtattgg      720
ttttacacag atgtctatga gatttacgga accgataaag cggaagcggt tgcggtcaag      780
ataaataata actactatat tgcaaagcgg caatga                              816
```

```
<210> SEQ ID NO 15
<211> LENGTH: 266
<212> TYPE: PRT
<213> ORGANISM: Clostridium scindens

<400> SEQUENCE: 15

Met Arg Leu Lys Asp Lys Val Ile Leu Val Thr Ala Ser Thr Arg Gly
1               5                   10                  15

Ile Gly Leu Ala Ile Ala Gln Ala Cys Ala Lys Glu Gly Ala Lys Val
            20                  25                  30

Tyr Met Gly Ala Arg Asn Leu Glu Arg Ala Lys Ala Arg Ala Asp Glu
        35                  40                  45

Met Asn Ala Ala Gly Gly Asn Val Lys Tyr Val Tyr Asn Asp Ala Thr
    50                  55                  60

Lys Glu Glu Thr Tyr Val Thr Met Ile Glu Ile Ile Glu Gln Glu
65                  70                  75                  80

Gly Arg Ile Asp Val Leu Val Asn Asn Phe Gly Ser Ser Asn Pro Lys
                85                  90                  95

Lys Asp Leu Gly Ile Ala Asn Thr Asp Pro Glu Val Phe Ile Lys Thr
            100                 105                 110

Val Asn Ile Asn Leu Lys Ser Val Phe Ile Ala Ser Gln Thr Ala Val
        115                 120                 125

Lys Tyr Met Ala Glu Asn Gly Gly Ser Ile Asn Ile Ser Ser
    130                 135                 140

Val Gly Gly Leu Ile Pro Asp Ile Ser Gln Ile Ala Tyr Gly Thr Ser
145                 150                 155                 160

Lys Ala Ala Ile Asn Tyr Leu Thr Lys Leu Ile Ala Val His Glu Ala
                165                 170                 175

Arg His Asn Ile Arg Cys Asn Ala Val Leu Pro Gly Met Thr Ala Thr
            180                 185                 190

Asp Ala Val Gln Asp Asn Leu Thr Asp Asp Phe Arg Asn Phe Phe Leu
        195                 200                 205

Lys His Thr Pro Ile Gln Arg Met Gly Leu Pro Glu Glu Ile Ala Ala
    210                 215                 220

Ala Val Val Tyr Phe Ala Ser Asp Ala Ala Tyr Thr Thr Gly Gln
225                 230                 235                 240

Ile Leu Thr Val Ser Gly Gly Phe Gly Leu Ala Thr Pro Ile Phe Gly
                245                 250                 255

Asp Leu Ser Glu Arg Ser Asp Ala Arg Gly
            260                 265
```

<210> SEQ ID NO 16
<211> LENGTH: 1305
<212> TYPE: DNA
<213> ORGANISM: Clostridium scindens

<400> SEQUENCE: 16

| | | |
|---|---|---|
| ggccggaatg cagaagttgt ccctggcgtt tttatgaagg cgaccggcat gagatattga | 60 |
| acgagacaga ccgggaacag gtatatgaag acctgttcca atggattgaa gatcagaaaa | 120 |
| tgacgcagca aaattaggac gctatactta agaaaagtat ccggataatg attacatgaa | 180 |
| tatgaaagat atctggaata ctaaaaataa atcatatgga gggattacac atgaggttaa | 240 |
| aagacaaagt gattctggtt acagcatcca ccagaggcat tggcctggct atcgctcagg | 300 |
| catgtgcgaa agaaggagcc aaagtctaca tgggcgccag gaatctggaa cgcgccaagg | 360 |
| cacgggctga cgagatgaat gcggcaggcg gcaatgtaaa gtatgtttac aatgatgcga | 420 |
| caaaagaaga gacatacgtg acgatgattg aggaaatcat cgagcaagaa gggcgcatag | 480 |
| acgtgcttgt aaataatttc ggctcatcaa atcccaagaa agatcttgga attgccaata | 540 |
| cagacccgga ggtattcatc aagacggtaa atatcaacct aaagagcgta tttatcgcaa | 600 |
| gccagacggc tgttaagtat atggcggaaa atggaggtgg aagcatcatc aatatctcat | 660 |
| ccgtaggagg cctgatacca gatatctctc agattgccta tggaaccagc aaagcggcaa | 720 |
| tcaactatct gacgaaactg atagccgtac acgaggcaag gcataacatc agatgcaatg | 780 |
| cggtacttcc aggaatgacg gcaacagatg cggtgcagga taatctgacg gatgacttcc | 840 |
| gaaacttctt cttgaagcat acgccaattc agcgtatggg gctcccggaa gagatcgcgg | 900 |
| cagccgtagt atacttcgca agcgatgatg ccgcatatac cacaggacag attcttaccg | 960 |
| tatctggcgg tttcggactg gcaacgccga tatttggaga tctgtctgaa cgctcagatg | 1020 |
| cccgcgggta gaatttcatg ggttaactta atcaaaagca gaatcaggaa aagagacagc | 1080 |
| cgggagcggc tgtctctttt atctatagtg cgcctagcgg cgcacgtttc taactttata | 1140 |
| ggaaagttct cctttcggag aacttgggga ctaaaatagc ccgctcaaaa gcgggcatag | 1200 |
| tgaatcagac ggtttggatt aaaagatgta aagccctct tcaccaaaat cgtcatcatc | 1260 |
| aaggttatca aattcatgta agaaataatc catatccaga agttc | 1305 |

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: modified_base
<222> LOCATION: (1)..(8)
<223> OTHER INFORMATION: This region may encompass 1-8 nucleotides
<220> FEATURE:
<221> NAME/KEY: modified_base
<222> LOCATION: (34)..(34)
<223> OTHER INFORMATION: a, c, t, g, unknown or other

<400> SEQUENCE: 17
nnnnnnnnnn nnnnnnnnnn aytgggydta aagng            35

-continued

```
<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
<220> FEATURE:
<221> NAME/KEY: modified_base
<222> LOCATION: (1)..(8)
<223> OTHER INFORMATION: This region may encompass 1-8 nucleotides

<400> SEQUENCE: 18
nnnnnnnnnn nnnnnnnnnn ccgtcaatty htttragt                              38

<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Dehydrobutyrine
<220> FEATURE:
<221> NAME/KEY: MOD_RES
<222> LOCATION: (3)..(3)
<223> OTHER INFORMATION: Dehydroalanine
<220> FEATURE:
<221> NAME/KEY: MOD_RES
<222> LOCATION: (5)..(5)
<223> OTHER INFORMATION: Dehydroalanine
<220> FEATURE:
<221> NAME/KEY: MOD_RES
<222> LOCATION: (8)..(8)
<223> OTHER INFORMATION: Dehydrobutyrine
<220> FEATURE:
<221> NAME/KEY: MOD_RES
<222> LOCATION: (13)..(13)
<223> OTHER INFORMATION: Dehydrobutyrine
<220> FEATURE:
<221> NAME/KEY: MOD_RES
<222> LOCATION: (23)..(23)
<223> OTHER INFORMATION: Dehydrobutyrine
<220> FEATURE:
<221> NAME/KEY: MOD_RES
<222> LOCATION: (25)..(25)
<223> OTHER INFORMATION: Dehydrobutyrine
<220> FEATURE:
<221> NAME/KEY: MOD_RES
<222> LOCATION: (29)..(29)
<223> OTHER INFORMATION: Dehydroalanine
```

```
<220> FEATURE:
<221> NAME/KEY: MOD_RES
<222> LOCATION: (33)..(33)
<223> OTHER INFORMATION: Dehydroalanine

<400> SEQUENCE: 20

Ile Xaa Xaa Ile Xaa Leu Ala Xaa Pro Gly Ala Lys Xaa Gly Ala Leu
1               5                   10                  15

Met Gly Ala Asn Met Lys Xaa Ala Xaa Ala His Ala Xaa Ile His Val
            20                  25                  30

Xaa Lys

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Dehydrobutyrine
<220> FEATURE:
<221> NAME/KEY: MOD_RES
<222> LOCATION: (3)..(3)
<223> OTHER INFORMATION: Dehydroalanine
<220> FEATURE:
<221> NAME/KEY: MOD_RES
<222> LOCATION: (5)..(5)
<223> OTHER INFORMATION: Dehydroalanine
<220> FEATURE:
<221> NAME/KEY: MOD_RES
<222> LOCATION: (8)..(8)
<223> OTHER INFORMATION: Dehydrobutyrine
<220> FEATURE:
<221> NAME/KEY: MOD_RES
<222> LOCATION: (13)..(13)
<223> OTHER INFORMATION: Dehydrobutyrine
<220> FEATURE:
<221> NAME/KEY: MOD_RES
<222> LOCATION: (18)..(18)
<223> OTHER INFORMATION: Dehydrobutyrine
<220> FEATURE:
<221> NAME/KEY: MOD_RES
<222> LOCATION: (23)..(23)
<223> OTHER INFORMATION: Dehydrobutyrine
<220> FEATURE:
<221> NAME/KEY: MOD_RES
<222> LOCATION: (25)..(25)
<223> OTHER INFORMATION: Dehydrobutyrine
<220> FEATURE:
<221> NAME/KEY: MOD_RES
<222> LOCATION: (31)..(31)
<223> OTHER INFORMATION: Dehydrobutyrine

<400> SEQUENCE: 21

Ile Xaa Xaa Lys Xaa Leu Ala Xaa Pro Gly Ala Val Xaa Gly Ile Leu
1               5                   10                  15

Met Xaa Ala Pro Val Gln Xaa Ala Xaa Ala Gly Ala Gln Ile Xaa Gly
            20                  25                  30

Lys
```

LANTIBIOTICS, LANTIBIOTIC-PRODUCING BACTERIA, COMPOSITIONS AND METHODS OF PRODUCTION AND USE THEREOF

CROSS-REFERENCE TO RELATED APPLICATIONS

The present application is a continuation of U.S. patent application Ser. No. 16/659,199, filed Oct. 21, 2019, now U.S. Pat. No. 11,207,374, which is a Continuation of International Patent Application No. PCT/US2018/028629, filed Apr. 20, 2018, which claims priority to U.S. Provisional Patent Application Ser. No. 62/488,480, filed Apr. 21, 2017, titled "Lantibiotics and Methods of Production and Use Thereof," which are incorporated by reference herein in their entireties.

STATEMENT OF GOVERNMENT INTEREST

This invention was made with government support under grant number AI042135, awarded by the National Institutes of Health. The government has certain rights in the invention.

SEQUENCE LISTING

The present specification makes reference to a Sequence Listing (submitted electronically as a .txt file named "072734_0948CON_SL.txt" on Dec. 28, 2021). The .txt file was generated on Dec. 28, 2021 and is 27,223 bytes in size. The entire contents of the Sequence Listing are hereby incorporated by reference.

TECHNICAL FIELD

The present disclosure relates to novel lantibiotics, lantibiotic pharmaceutical compositions containing such novel lantibiotics, and methods of making and using the lantibiotics, including their use as anti-microbial agents. The present disclosure also relates to isolated *B. producta* that produce these novel lantibiotics, recombinant bacteria that express genes encoding these novel lantibiotics and thus produce these novel lantibiotics, and to bacterial pharmaceutical compositions and methods for decreasing the risk of developing vancomycin-resistant Enterococci (VRE) infection or colonization and for treating VRE infection or colonization using isolated *B. producta* that produce these novel lantibiotics, or recombinant bacteria that express genes encoding these novel lantibiotics and thus produce these novel lantibiotics.

BACKGROUND

Lantipeptides are a group of ribosomally-synthesized peptides that are then post-translationally modified, often by dehydration, to include non-naturally occurring amino acids. Lantipeptides with anti-microbial activity are often referred to as lantibiotics.

Nisin is a common 34-amino acid lantibiotic produced by *Lactococcus lactis* (*L. lactis*) that is often used as a food preservative. Like nisin, lantibiotics are often produced by gram-positive bacteria and exhibit anti-microbial activity against other gram-positive bacteria.

The gastrointestinal tract of mammals is densely colonized by hundreds of microbial species that coexist symbiotically with their hosts. The microbes, collectively referred to as the microbiota, contribute to numerous aspects of host health, including nutrient metabolism, homeostasis of intestinal tissues, development of innate and adaptive immune responses, and more generally, defense against intestinal infection. Bacteria antagonize intestinal pathogens directly, through contact-dependent and soluble factor-mediated inhibition, as well as indirectly by calibrating and inducing host immune responses, but the contributions of individual bacteria to colonization resistance against specific pathogens are not well understood.

Enterococci are a genus of gram-positive, round-shaped bacteria that commonly live in the gut, although they can cause infection anywhere in the body. The genus has a high amount of intrinsic resistance to some classes of antibiotics, but is generally sensitive to vancomycin. However, particularly virulent strains that are resistant even to vancomycin are an emerging and are a growing problem, particularly in institutional settings. Such vancomycin-resistant strains are referred to as VRE. The two main VRE species are vancomycin-resistant *Enterococcus faecium* (*E. faecium*) and vancomycin-resistant *Enterococcus faecalis* (*E. faecalis*). VRE can exist in the body, typically in the gastrointestinal tract, without causing a disease or other harmful effects. However, VRE can sometimes cause local disease in the gastrointestinal tract and they can invade sites outside the gastrointestinal tract and cause disease, for example, in the bloodstream, abdomen, or urinary tract. VRE in the bloodstream can be particularly problematic because, once in the bloodstream, VRE can cause sepsis, meningitis, pneumonia, or endocarditis.

SUMMARY

The present disclosure provides a lantibiotic composition including an isolated lantibiotic including a domain having the amino acid sequence of SEQ. ID. No.: 3. According to further aspects, which can be combined with one another or implemented separately, the lantibiotic can be purified and/ or the domain having the amino acid of SEQ. ID. No.: 3 can further have a thioether cross-link between DHA3 and ALAI, DHB8 and ALA11, DHB13 and ALA19, DHB23 and ALA26, DHB25 and ALA28.

The present disclosure further provides any of the above compositions in a lantibiotic pharmaceutical composition also containing a pharmaceutically acceptable carrier. According to further aspects, which can be implemented separately or combined with one another unless clearly mutually exclusive: i) the lantibiotic pharmaceutical composition can be formulated for administration to a patient; ii) the lantibiotic pharmaceutical composition can be formulated to treat a gram-positive bacteria infection of the patient, and the lantibiotic can be present in a therapeutically effective amount; iii) the lantibiotic pharmaceutical composition can be formulated for administration to a food; iv) the lantibiotic pharmaceutical composition can be formulated to inhibit the growth of or kill a gram-positive bacteria in the food, and the lantibiotic can be present in an effective amount; v). the gram-positive bacteria can be a vancomycin resistant enterococci (VRE); vi) the gram-positive bacteria can be *S. aureus*, *E. faecalis*, *E. faecium*, or *L. monocytogenes*.

The present disclosure further provides a method of treating a gram-positive bacterial colonization or infection by administering to a patient in need of such treatment, a therapeutically effective amount of any lantibiotic pharmaceutical composition described herein. According to further aspects, which can be implemented separately or combined with one another unless clearly mutually exclusive: i) the lantibiotic pharmaceutical composition can include the lantibiotic in a formulation suitable for administration to the patient; ii) treating can include preventing a gram-positive bacteria colonization or infection; iii) treating can include inhibiting growth of the gram-positive bacteria in the patient, killing the gram-positive bacteria in the patient, and/or ameliorating at least one symptom of infection with the gram-positive bacteria in the patient.

The present disclosure also provides for the use of any of the above lantibiotic pharmaceutical compositions for treatment of a gram-positive bacteria colonization or infection in a patient. The use can include administering to the patient a therapeutically effective amount of the lantibiotic pharmaceutical composition. The use can further include actions described in connection with any of the methods described above.

The present disclosure also provides a lantibiotic-producing recombinant bacteria including at least one expressible nucleic acid comprising an exogenous a nucleic acid having the sequence of SEQ. ID. No.: 5, 6, 7, 8, 9, 10, 11, 12, 13 and/or 14 operably linked to a promoter and operable to produce a lantibiotic having the sequence of SEQ. ID. No.: 3. According to a further aspect, the lantibiotic-producing recombinant bacteria may further include at least one expressible nucleic acid encoding one or more enzymes operable to convert a primary bile acid to a secondary bile acid, the nucleic acid operably linked to a promoter and operable to produce the one or more enzymes operable to convert a primary bile acid to a secondary bile acid.

The present disclosure further provides a bacterial pharmaceutical composition including an isolated lantibiotic-producing $B.$ $producta$ bacteria or a lantibiotic-producing recombinant bacteria comprising at least one expressible nucleic acid comprising a nucleic acid having the sequence of SEQ. ID. No.: 5, 6, 7, 8, 9, 10, 11, 12, 13, and/or 14 and operable to produce a lantibiotic having the sequence of SEQ. ID. No.: 3 and a pharmaceutically acceptable carrier.

According to further aspects, which can be implemented separately or combined with one another unless clearly mutually exclusive: i) the bacterial pharmaceutical composition can further include at least one expressible nucleic acid encoding one or more enzymes operable to convert a primary bile acid to a secondary bile acid, the nucleic acid operably linked to a promoter and operable to produce the one or more enzymes operable to convert a primary bile acid to a secondary bile acid; ii) the bacterial pharmaceutical composition can further include at least one supplementary therapeutic bacteria, wherein the supplementary therapeutic bacteria is $Clostridium$ $scindens$ (C. $scindens$), $Clostridium$ $hiranonis$ (C. $hiranonis$), $Clostridium$ $hylemonae$ (C. $hylemonae$) bacteria, a non-lantibiotic producing $B.$ $producta$ bacteria, or any combinations thereof; iii) the bacterial pharmaceutical composition can further include at least one further supplementary therapeutic bacteria wherein the supplementary therapeutic bacteria is $Parabacteroides$ $distasonis$ (P. $distasonis$), $Bacteroides$ $sartorii$ (B. $sartorii$), $Clostridium$ $innocuum$ (C. $innocuum$), $Akkermansia$ $muciniphila$ (A. $muciniphila$), C. $bolteae$, $Blautia$ unclassified, $Eubacterium$ $dolichum$ (E. $dolichum$), or any combinations thereof; iv) the bacterial pharmaceutical composition can further include an isolated lantibiotic comprising a domain having the amino acid sequence of SEQ. ID. No.: 3; v) the bacterial pharmaceutical composition can further include nisin; vi) the lantibiotic-producing recombinant bacteria can further include an enzyme operable to convert a primary bile acid to a secondary bile acid; vii) the bacterial pharmaceutical composition can further include a secondary bile acid comprises 7-α-hydroxysteroid dehydrogenase; viii) the bacterial pharmaceutical composition can be in a formulation suitable for administration to the patient.

The present disclosure also provides a bacterial pharmaceutical composition including at least one bacteria, wherein the bacteria is $Clostridium$ $scindens$ (C. $scindens$), $Clostridium$ $hiranonis$ (C. $hiranonis$), $Clostridium$ $hylemonae$ (C. $hylemonae$) bacteria, a non-lantibiotic producing $B.$ $producta$ bacteria, or any combinations thereof. According to further aspects, which can be implemented separately or combined with one another unless clearly mutually exclusive: i) the bacterial pharmaceutical composition can further include at least one further bacteria, wherein the one further bacteria is $Parabacteroides$ $distasonis$ (P. $distasonis$), $Bacteroides$ $sartorii$ (B. $sartorii$), $Clostridium$ $innocuum$ (C. $innocuum$), $Akkermansia$ $muciniphila$ (A. $muciniphila$), C. $bolteae$, $Blautia$ unclassified, $Eubacterium$ $dolichum$ (E. $dolichum$), or any combinations thereof; ii) the bacterial pharmaceutical composition can further include an isolated lantibiotic comprising a domain having the amino acid sequence of SEQ. ID. No.: 3; iii) the bacterial pharmaceutical composition can further include nisin; iv) the bacterial pharmaceutical composition can further include an enzyme operable to convert a primary bile acid to a secondary bile acid; iv) the bacterial pharmaceutical composition can further include 7-α-hydroxysteroid dehydrogenase; v) bacterial pharmaceutical composition can be in a formulation suitable for administration to the patient.

The disclosure further provides a method of treating a gram-positive bacteria colonization or infection, the method including administering to a patient in need of such treatment, a therapeutically effective amount of any of the above bacterial pharmaceutical compositions. According to further aspects, which can be implemented separately or combined with one another unless clearly mutually exclusive: i) the gram-positive bacteria can be a vancomycin resistant enterococci (VRE); ii) the gram-positive bacteria can be $S.$ $aureus$, $E.$ $faecalis$, $E.$ $faecium$, or $L.$ $monocytogenes$; iii) treating can include preventing a gram-positive bacteria colonization or infection; iv) treating can include inhibiting growth of the gram-positive bacteria in the patient, killing the gram-positive bacteria in the patient, and/or ameliorating at least one symptom of infection with the gram-positive bacteria in the patient.

The present disclosure also provides for the use of any of the above bacterial pharmaceutical compositions for treatment of a gram-positive bacteria colonization or infection in a patient. The use can include administering to the patient a therapeutically effective amount of the bacterial pharmaceutical composition. The use can further include actions described in connection with any of the methods described above.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which:

In FIG. 37, bars represent the median, whiskers represent inter-quartile range. FIG. 37A is a graph of VRE CFU in mice feces over the study period. FIG. 37B is graph of amount of VRE spp. 16S sequence reads over the study period. FIG. 37C is a graph of the amount of *Blautia* spp. 16S sequence reads, *Clostridium* spp. 16S sequence reads, and VRE spp. 16S sequence reads at day 15 post-reconstitution.

FIG. 39A is a graph of VRE CFU in mice feces over the study period for a bacterial suspension of all the bacteria (7-mix). FIG. 39B is a graph of VRE CFU in mice feces over the study period for a variety of bacterial suspensions: *A. muciniphila, B. producta* (non-lantibiotic-producing strain), *C. bolteae, B.s sartorii*, and *P. distasonis* (5-mix); *B. producta* (non-lantibiotic-producing strain), *C. bolteae, B. sartorii*, and *P. distasonis* (4-mix); *C. bolteae, B. sartorii*, and *P. distasonis* (3-mix A); *B. producta* (non-lantibiotic-producing strain), *B. sartorii*, and *P. distasonis* (3-mix B); *B. producta* (non-lantibiotic-producing strain) and *C. bolteae*, (2-mix A); and *B. sartorii* and *P. distasonis* (2-mix B).

FIG. 40A is a graph of VRE CFU in mice feces over the study period. FIG. 40B is a graph of VRE CFU in intestinal content at the end of the study period.

DETAILED DESCRIPTION

Figure 1:
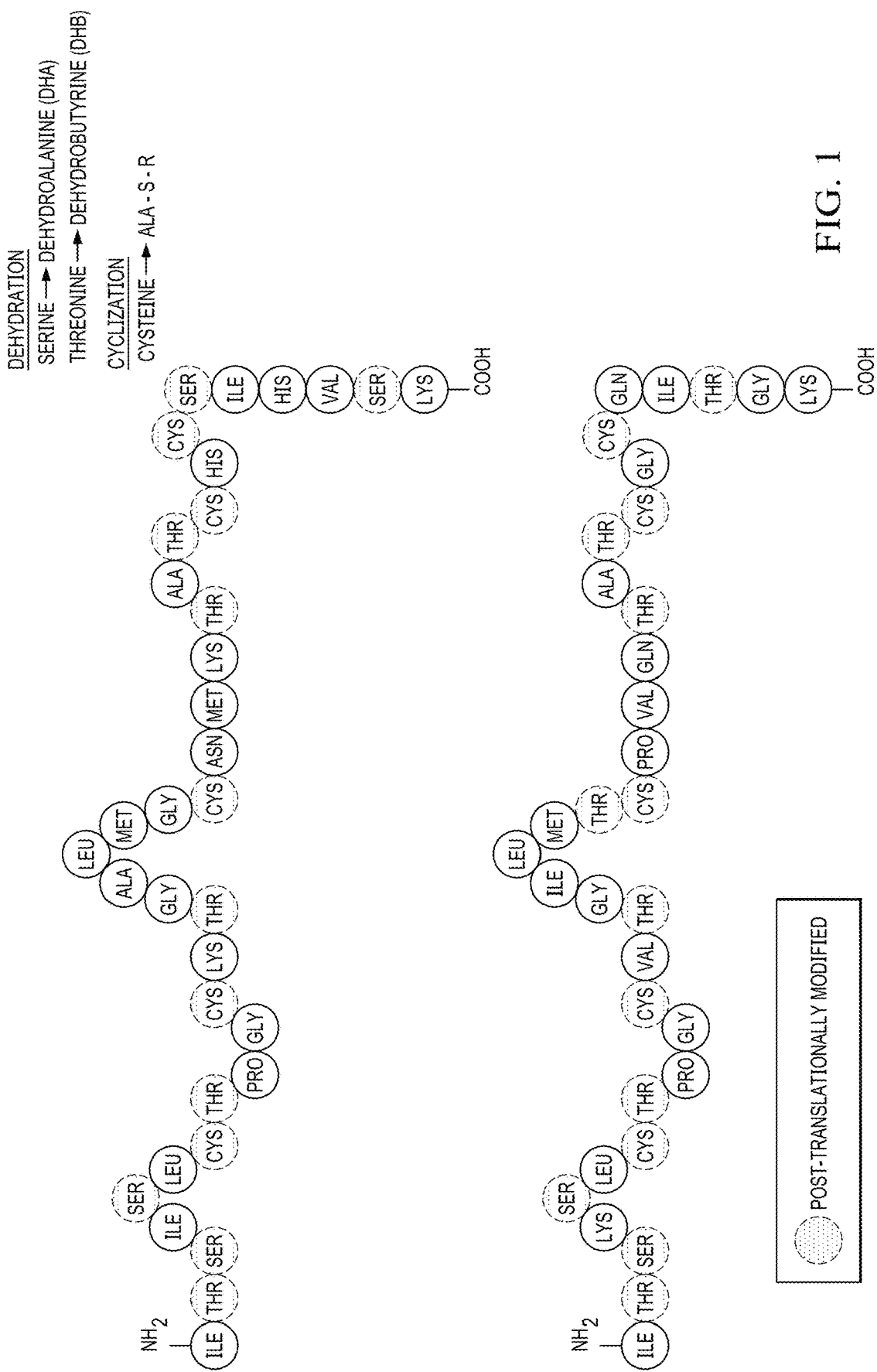
FIG. 1 is a schematic diagram of the amino acid sequence of a precursor peptide of nisin and a precursor peptide of a lantibiotic as disclosed herein and having SEQ. ID. No.: 1.

The present disclosure relates to lantipeptides, in particular lantibiotics, that inhibit growth of gram-positive bacteria, particularly gram-positive bacteria other than *Blautia producta*. The disclosure further provides novel lantibiotics, lantibiotic pharmaceutical compositions containing such novel lantibiotics, and methods of making and using the lantibiotics, including their use as anti-microbial agents. The present disclosure also relates to isolated *B. producta* that produce these novel lantibiotics, recombinant bacteria that express genes encoding these novel lantibiotics and thus produce these novel lantibiotics, and to bacterial pharmaceutical compositions and methods for decreasing the risk of developing vancomycin-resistant Enterococci (VRE) infection or colonization and for treating VRE infection or colonization using isolated *B. producta* that produce these novel lantibiotics, or recombinant bacteria that express genes encoding these novel lantibiotics and thus produce these novel lantibiotics.

For clarity of description, and not by way of limitation, this section is divided into the following subsections:
(i) Lantibiotics;
(ii) Lantibiotic-producing bacteria;
(iii) Methods of producing lantibiotics;
(iii) Pharmaceutical compositions; and
(iv) Methods of treatment and use.

The following are terms relevant to the present invention:

As used herein, the terms "isolated," and "isolate" denote a degree of separation from the original source or surroundings.

As used herein, an "isolated lantibiotic" is one which has been identified and separated and/or recovered from a component of its natural environment. "Synthetic lantibiotics" or "recombinant lantibiotics" are generally generated using recombinant technology or using peptide synthetic techniques known to those of skill in the art.

An "isolated" bacteria is also one which has been identified and separated and/or recovered from a component of its natural environment.

The terms "purified" and "purify" denote a degree of separation that is higher than isolated. A "purified" protein or nucleic acid is sufficiently free of other materials such that any impurities do not materially affect the biological properties of the protein or cause other adverse consequences. That is, a nucleic acid or polypeptide of the presently disclosed subject matter is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to post-translational modifications, as in the case of lantibiotics, different modifications can give rise to different isolated proteins, which can be separately purified.

As used herein "gram-positive bacteria" refers to a bacteria that gives a positive result in a Gram stain test. "Gram-positive bacteria" include, but are not limited to, VRE.

As used herein, "*B. producta*" refers generically to any bacteria with a 16S subunit gene having a nucleotide sequence at least 95% similar to that described for strain 2396 and contained in NCBI Reference Sequence: NR_036776.1. Specific strains of *B. producta* are also identified herein and may be identified by 16S subunit genes or by other conventional methods of strain-identification. Some strains, such as the Caballero strain, are lantibiotic-producing bacteria. Other strains are non-lantibiotic-producing bacteria unless recombinantly modified. A *B. producta* bacteria can be that described in Liu et al., "Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces," Int. J. Syst. Evol. Microbiol., 2008, 58:1896-1902 and/or Ezaki et al. "16S ribosomal DNA sequences of anaerobic cocci and proposal of *Ruminococcus hansenii* comb. nov. and *Ruminococcus productus* comb. nov.," Int J Syst Bacteriol. 1994, 44:130-136. A *B. producta* bacteria suitable for use the disclosure is as deposited in, and available from, the American Type Culture Collection (Manassas, VA), accession number ATCC 27340, Strain DSM2950. The *B. producta* can have the 16S ribosomal RNA gene sequence set forth in GenBank Accession Nos. D14144 and/or X94966. The *B. producta* can have the whole genome nucleic acid sequence set forth in GenBank Accession No. AUUC00000000.

As used herein, "VRE" means vancomycin-resistant *Enterococcus*/i, which include vancomycin-resistant *E. faecium* and/or vancomycin-resistant *E. faecalis*. VRE can refer to any bacteria with a 16S subunit gene having a nucleotide sequence at least 95% similar to that of 16S subunit gene sequence contained in NCBI Reference Sequence: CP014449.1. If a particular VRE species or strain is intended, such as in certain of the Examples, it is specified.

As used herein "*L. monocytogenes*" refers to any bacteria with a 16S subunit gene having a nucleotide sequence at least 95% similar to that of the 16S subunit gene sequence contained in NCBI Reference Sequence: NC_017544.1.

As used herein "*S. aureus*" refers to any bacteria with a 16S subunit gene having a nucleotide sequence at least 95% similar to that of the 16S subunit gene sequence contained in NCBI Reference Sequence: NC_007795.1.

As used herein "*C. bolteae*" refers to any bacteria with a 16S subunit gene having a nucleotide sequence at least 95% similar to that of the 16S subunit gene sequence contained in NCBI Reference Sequence: NZ AGYH00000000.1.

As used herein "*P. distasonis*" refers to any bacteria with a 16S subunit gene having a nucleotide sequence at least 95% similar to that of the 16S subunit gene sequence contained in NCBI Reference Sequence: NC_009615.1.

As used herein "*B. sartorii*" refers to any bacteria with a 16S subunit gene having a nucleotide sequence at least 95% similar to that of the 16S subunit gene sequence contained in NCBI Reference Sequence: NZ BAMF00000000.1.

As used herein "*C. dificile*" refers to any bacteria with a 16S subunit gene having a nucleotide sequence at least 95% similar to that of the 16S subunit gene sequence contained in NCBI Reference Sequence: NC_009089.1.

As used herein "*K. pneumoniae*" refers to any bacteria with a 16S subunit gene having a nucleotide sequence at least 95% similar to that of the 16S subunit gene sequence contained in NCBI Reference Sequence: NC_016845.1.

As used herein "*E. coli*" refers to any bacteria with a 16S subunit gene having a nucleotide sequence at least 95% similar to that of the 16S subunit gene sequence contained in NCBI Reference Sequence: NC_002695.1.

As used herein "*C. scindens*" refers to any bacteria with a 16S subunit gene having a nucleotide sequence at least 95% similar to that of the 16S subunit gene sequence contained in GenBank Accession No. AF262238. The *C. scindens* bacteria can also be that described in Morris et al., "*Clostridium scindens* sp. nov., a Human Intestinal Bacterium with Desmolytic Activity on Corticoids," Int J Syst Bacteriol, October 1985, 35:478-481, and/or Krafft et al., "Purification and characterization of a novel form of 20-alpha-hydroxysteroid dehydrogenase from *Clostridium scindens*," J Bacteriol. June 1989, 171:2925-2932. *C. scindens* bacteria suitable for use in the disclosure are as deposited in, and available from, the American Type Culture Collection (Manassas, VA), accession number ATCC 35704, Strain Designation VPI 13733. The a *C. scindens* bacteria can have the whole genome nucleic acid sequence is set forth in GenBank Accession No. ABFY 02000000. Examples of characteristics of *C. scindens* useful in the present disclosure are the ability to express at least one of 20-alpha-hydroxysteroid dehydrogenase, 7-beta-dehydrogenase, 7-alpha-dehydroxylase, and steroid desmolase.

As used herein, *A. muciniphila* refers to any bacteria with a 16S subunit gene having a nucleotide sequence at least 95% similar to that of the 16S subunit gene sequence contained in NCBI Reference Sequence: KT340103.1.

As used herein, *E. dolichum*, refers to any bacteria with a 16S subunit gene having a nucleotide sequence at least 95% similar to that of the 16S subunit gene sequence contained in NCBI Reference Sequence: NR_044647.2.

As used herein, *B. hansenii* refers to any bacteria with a 16S subunit gene having a nucleotide sequence at least 95% similar to that of the 16S subunit gene sequence contained in NCBI Reference Sequence: NR_118731.1.

Other bacterial identified herein, including, but not limited to *B. intestihominis* Buffie and Pamer, Nature Reviews Immunology 13:790-801, *P. capillosus, C. hiranonis, C. hylemonae, C. perfringens, C. sordellii, P. sphenisci,* Lachnospiraceae 5_1_57FAA, Clostridiales VE202-05 and/or Clostridiales VE202-26 *C. innocuum, Blautia* unclassified, *Lactococcus lactis, Bacillus subtilis, Bificobacterium bifidum,* and *Listeria innocua* may be identified through reference to NCBI reference sequences.

As used herein, the term "subject" or "patient" refers to any animal, including any mammal, including, but not limited to, humans, and non-human animals (including, but not limited to, non-human primates, dogs, cats, rodents, horses, cows, pigs, sheep, goats, mice, rats, hamsters, rabbits, and the like (e.g., which is to be the recipient of a particular treatment). The subject or patient can be a human.

As used herein, "colonization" refers to the presence of a bacterial population without clinically detectable infection and is included in "infection" as used herein.

As used herein, "VRE colonization" or colonization with VRE" as used herein designate colonization of a site in the gastrointestinal tract of a patient with VRE bacteria without a VRE infection symptom or without a VRE infection symptom attributable to VRE colonization. VRE can be detectable by the culture of VRE from or detection of VRE biomarkers in the feces, intestinal contents, sputum, blood, urine, or wound of the patient. VRE biomarkers include VRE-specific nucleic acids or proteins, including protein fragments, and/or nucleic acid or protein profiles, such as VRE-specific 16S rRNA. VRE biomarkers are detectable at least by sequencing, PCR-based tests, and protein assays, and nucleic and/or protein arrays, as applicable for the particular VRE biomarker(s).

As used herein, "infection" as used herein designates the presence of the indicated bacteria, for example colonization, and, optionally, also the presence of one or more clinical symptoms of infection. Common symptoms of bacterial infection can vary by location and bacteria, but can include general or localized pain and/or inflammation, fever, and/or chills. Common symptoms of gastrointestinal infection also include diarrhea, vomiting, abdominal tenderness, and/or abdominal pain.

As used herein, "VRE infection" and "infection with VRE" as used herein designate VRE colonization and, optionally, also the presence of one or more VRE infection symptoms. A "VRE infection symptom" includes include one or more symptoms of "Enterocolitis infectious" as defined in the Common Terminology Criteria for Adverse Events, Version 4 (CTCAE), one or more symptoms of "Sepsis" as defined in the CTCAE, and/or one or more of abdominal tenderness, abdominal pain, abdominal cramping, sepsis, endocarditis, meningitis, headache, stiff neck, confusion, back pain, pneumonia, fever, chills, diarrhea, urinary tract infection, endocarditis, elevated white blood cell count, and decreased serum albumin, when such symptom is attributable to VRE colonization.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and/or remission or improved prognosis. By preventing progression of a disease or disorder, a treatment can prevent deterioration due to the disease or disorder in an affected or diagnosed patient or in a patient suspected of having the disease or disorder, but also a treatment can prevent the onset of the disease or disorder or a symptom of the disease or disorder in a patient at risk for the disorder or suspected of having the disease or disorder. "Treatment" can specifically refer to avoiding and/or reducing the extent and/or duration of infection with gram-positive bacteria in general, a target set of gram-positive bacteria, or a target gram-positive bacteria. "Treatment" can also specifically refer to substantial clearance of gram-positive bacteria in general, a target set of gram-positive bacteria, or a target gram-positive bacteria, such as clearance from the intestinal tract. "Treatment" can further specifically refer to avoidance of even colonization with gram-positive bacteria in general, a target set of gram-positive bacteria, or a target gram-positive bacteria, or a reduction in the number of colonizing bacteria.

"Treatment" in the context of a gram-positive bacteria colonization, particularly VRE, *S. aureus, E. faecalis, E. faecium,* and/or *L. monocytogenes* bacteria colonization, can result in a 10%, 20%, 30%, 40%, 50%, 60%, 70%, 80%, 90%, 95%, 98% or 99% decrease in risk of the gram-positive bacteria, particularly the VRE, *S. aureus, E. faecalis, E. faecium,* and/or *L. monocytogenes* bacteria, colonization. The decrease can be measured by a decrease in fecal CFU of the gram-positive bacteria, particularly the VRE, *S. aureus, E. faecalis, E. faecium,* and/or *L. monocytogenes* bacteria, a decrease in fecal gram-positive bacteria, particularly VRE, *S. aureus, E. faecalis, E. faecium,* and/or *L. monocytogenes* bacteria, biomarker, a decrease in blood gram-positive bacteria, particularly VRE, *S. aureus, E. faecalis, E. faecium,* and/or *L. monocytogenes* bacteria, biomarker, and/or a decrease in urine gram-positive bacteria, particularly VRE, *S. aureus, E. faecalis, E. faecium,* and/or *L. monocytogenes* bacteria, biomarker, as compared to an untreated patient with the same gram-positive bacteria, particularly the same VRE, *S. aureus, E. faecalis, E. faecium,* and/or *L. monocytogenes* bacteria, colonization, an untreated patient without the same gram-positive bacteria, particularly the same VRE, *S. aureus, E. faecalis, E. faecium,* and/or *L. monocytogenes* bacteria, colonization, or the same patient prior to treatment.

"Treatment" in the context of a gram-positive bacteria infection, particularly a VRE, *S. aureus, E. faecalis, E. faecium,* and/or *L. monocytogenes* bacteria infection, and/or one or more gram-positive bacteria infection symptoms, particularly VRE, *S. aureus, E. faecalis, E. faecium,* and/or *L. monocytogenes* bacteria infection symptoms, can result in a 10%, 20%, 30%, 40%, 50%, 60%, 70%, 80%, 90%, 95%, 98% or 99% decrease in severity of the gram-positive bacteria, particularly VRE, *S. aureus, E. faecalis, E. faecium,* and/or *L. monocytogenes* bacteria, infection or the gram-positive bacteria, particularly VRE, *S. aureus, E. faecalis, E. faecium,* and/or *L. monocytogenes* bacteria, infection symptoms, such as a decrease in fecal CFU of the gram-positive bacteria, particularly the VRE, *S. aureus, E. faecalis, E. faecium,* and/or *L. monocytogenes* bacteria, a decrease in fecal gram-positive bacteria, particularly VRE, *S. aureus, E. faecalis, E. faecium,* and/or *L. monocytogenes* bacteria, biomarker, a decrease in blood gram-positive bacteria, particularly VRE, *S. aureus, E. faecalis, E. faecium,* and/or *L. monocytogenes* bacteria biomarker, and/or a decrease in urine gram positive bacteria, particularly VRE, *S. aureus, E. faecalis, E. faecium,* and/or *L. monocytogenes* bacteria, biomarker as compared to an untreated patient with the same gram-positive bacteria, particularly VRE, *S. aureus, E. faecalis, E. faecium,* and/or *L. monocytogenes* bacteria, infection or the same patient prior to treatment.

"Treatment" in the context of a gram-positive bacteria infection, particularly VRE, *S. aureus, E. faecalis, E. faecium,* and/or *L. monocytogenes* bacteria infection, and/or one or more gram-positive bacteria infection symptoms, particularly VRE, *S. aureus, E. faecalis, E. faecium,* and/or *L. monocytogenes* bacteria infection symptoms, can mean reducing the risk of gram-positive bacteria, particularly VRE, *S. aureus, E. faecalis, E. faecium,* and/or *L. monocytogenes* bacteria, infection, and/or increasing resistance to gram-positive bacteria, particularly VRE, *S. aureus, E. faecalis, E. faecium,* and/or *L. monocytogenes* bacteria, infection, and/or reducing the severity of gram-positive bacteria, particularly VRE, *S. aureus, E. faecalis, E. faecium,* and/or *L. monocytogenes* bacteria, infection in a patient or population. Treatment can also mean a decrease in the grade of a VRE infection as determine by reference to the CTCAE, or a decrease in the grade of another gram-positive bacteria infection, particularly *S. aureus, E. faecalis, E. faecium,* and/or *L. monocytogenes* bacteria infection, by reference to CTCAE or another established clinical grading standard.

"Treatment" can also mean a decrease in actual mortality for a patient as compared to a similar patient without treatment or a decrease in the length of time the gram-positive bacteria, particularly VRE, *S. aureus, E. faecalis, E. faecium,* and/or *L. monocytogenes* bacteria, is detectable by fecal CFU, fecal gram-positive bacteria, particularly VRE, *S. aureus, E. faecalis, E. faecium,* and/or *L. monocytogenes* bacteria, biomarker detection, and/or blood or urine gram-positive bacteria, particularly VRE, *S. aureus, E. faecalis, E. faecium,* and/or *L. monocytogenes* bacteria, biomarker detection in a patient or patient population as compared to a similar patient or patient population with the same gram-positive bacteria, particularly the same VRE, *S. aureus, E. faecalis, E. faecium,* and/or *L. monocytogenes* bacteria, infection and without treatment.

For both gram-positive bacteria infection and colonization, particularly VRE, *S. aureus, E. faecalis, E. faecium,* and/or *L. monocytogenes* bacteria infection and colonization, treatment can also mean a decrease in the quantity of gram-positive bacteria, particularly VRE, *S. aureus, E. faecalis, E. faecium,* and/or *L. monocytogenes* bacteria, detectable in a patient or population of patients after treatment as compared to a similar sample from the patient or population of patients prior to treatment, for example a quantitative decrease in the titer of gram-positive bacteria, particularly VRE, *S. aureus, E. faecalis, E. faecium,* and/or *L. monocytogenes* bacteria, detected in a fecal sample.

As used herein, an "effective amount" or "therapeutically effective amount" is an amount sufficient to effect a beneficial or desired clinical result upon treatment. An effective amount can be administered to a patient in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition and the form and effective concentration of the lantibiotic, lantibiotic pharmaceutical composition, or bacterial pharmaceutical composition, or other treatment being administered.

An effective amount can decrease the severity of and/or reduce the likelihood of a colonization or an infection in a patient by gram-positive bacteria in general, by a set of gram-positive bacteria, or by a target gram-positive bacteria, particularly VRE, *S. aureus, E. faecalis, E. faecium,* and/or *L. monocytogenes* bacteria, as compared to an untreated, otherwise clinically similar patient. The decrease can be a 10%, 20%, 30%, 40%, 50%, 60%, 70%, 80%, 90%, 95%, 98% or 99% decrease in a biological metric of colonization or infection in a sample from the patient, such as a decrease in colony forming units of a gram-positive bacteria, particularly VRE, *S. aureus, E. faecalis, E. faecium,* and/or *L. monocytogenes* bacteria, in a sample from the patient as compared to an untreated patient with gram-positive bacteria, particularly VRE, *S. aureus, E. faecalis, E. faecium,* and/or *L. monocytogenes* bacteria, colonization or infection. Suitable samples include a gastrointestinal sample, urine, blood, a respiratory sample, or a wound swab. The biological metric of colonization or infection can be CFU of the gram-positive bacteria, particularly VRE, *S. aureus, E. faecalis, E. faecium,* and/or *L. monocytogenes* bacteria.

In the context of administering a composition to reduce the risk of gram-positive bacteria, particularly VRE, *S. aureus, E. faecalis, E. faecium*, and/or *L. monocytogenes* bacteria, colonization and/or increase resistance to gram-positive bacteria, particularly VRE, *S. aureus, E. faecalis, E. faecium*, and/or *L. monocytogenes* bacteria, colonization in a patient, and/or reduce the amount of a gram-positive bacteria, particularly VRE, *S. aureus, E. faecalis, E. faecium*, and/or *L. monocytogenes* bacteria, colonizing the patient, an effective amount of a composition described herein is an amount sufficient to treat the gram-positive bacteria, particularly VRE, *S. aureus, E. faecalis, E. faecium*, and/or *L. monocytogenes* bacteria, colonization. An effective amount can decrease the severity of and/or reduce the likelihood of a gram-positive bacteria, particularly VRE, *S. aureus, E. faecalis, E. faecium*, and/or *L. monocytogenes* bacteria, infection.

In the context of administering a composition to reduce the risk of gram-positive bacteria, particularly VRE, *S. aureus, E. faecalis, E. faecium*, and/or *L. monocytogenes* bacteria, infection and/or increase resistance to the gram-positive bacteria, particularly VRE, *S. aureus, E. faecalis, E. faecium*, and/or *L. monocytogenes* bacteria, infection in a patient, including reducing such risk and increasing such resistance in a patient colonized with the gram-positive bacteria, particularly VRE, *S. aureus, E. faecalis, E. faecium*, and/or *L. monocytogenes* bacteria, administering a composition to reduce the severity of the gram-positive bacteria, particularly VRE, *S. aureus, E. faecalis, E. faecium*, and/or *L. monocytogenes* bacteria, infection in a patient, and/or administering a composition to reduce a gram-positive bacteria, particularly VRE, *S. aureus, E. faecalis, E. faecium*, and/or *L. monocytogenes* bacteria, infection symptom in a patient, an effective amount of a composition described herein is an amount sufficient to treat the gram-positive bacteria, particularly VRE, *S. aureus, E. faecalis, E. faecium*, and/or *L. monocytogenes* bacteria, infection. An effective amount can decrease the severity of and/or reduce the likelihood of the gram-positive bacteria, particularly VRE, *S. aureus, E. faecalis, E. faecium*, and/or *L. monocytogenes* bacteria, infection.

An effective amount with respect to gram-positive bacteria, particularly VRE, *S. aureus, E. faecalis, E. faecium*, and/or *L. monocytogenes* bacteria, colonization or infection can be administered in one or more administrations.

As used herein, the term "pharmaceutical composition" includes both lantibiotic pharmaceutical compositions and bacterial pharmaceutical compositions.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" is used to denote a nucleic acid molecule that is either linear or circular, into which another nucleic acid sequence fragment of appropriate size can be integrated. Such nucleic acid fragment(s) can include additional segments that provide for transcription of a gene encoded by the nucleic acid sequence fragment. The additional segments can include and are not limited to: promoters, transcription terminators, enhancers, internal ribosome entry sites, untranslated regions, polyadenylation signals, selectable markers, origins of replication and such, as known in the art. Expression vectors are often derived from plasmids, cosmids, viral vectors and yeast artificial chromosomes; vectors are often recombinant molecules containing nucleic acid sequences from several sources.

As used herein, the term "operably linked," when applied to nucleic acid sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

Lantibiotics

Lantibiotics of the present disclosure include isolated or purified post-translationally modified peptides that exhibit anti-microbial activity against gram-positive bacteria other than lantibiotic-producing *B. producta*. Lantibiotics as disclosed herein can generally have a structure as described in and be formed using methods disclosed for other lantibiotics, particularly Type A(I) lantibiotics, such as nisin, in McAuliffe et al. "Lantibiotics: structure, biosynthesis and mode of action," FEMS Microbiology Reviews 25 (2001) 285-308, which is incorporated by reference in its entirety herein.

Lantibiotics as disclosed herein can be formed from a precursor that is ribosomally or artificially synthesized to consist essentially of, consist of, or comprise a domain having the amino acid sequence: ITSKSLCTPGCVTGILMTCPVQTATCGCQITGK (SEQ. ID. No: 1), as shown in FIG. 1. Lantibiotics as disclosed herein can also be formed from a precursor that is ribosomally or artificially synthesized to consist essentially of, consist of, or comprise a domain having the amino acid sequence: MAKFDDFDLDVTKTAAGEGGVE-PRITSKSLCTPGCVTGILMTCPVQTATCGCQITGK (SEQ. ID. No: 2), also as shown in FIG. 1.

Figure 2:
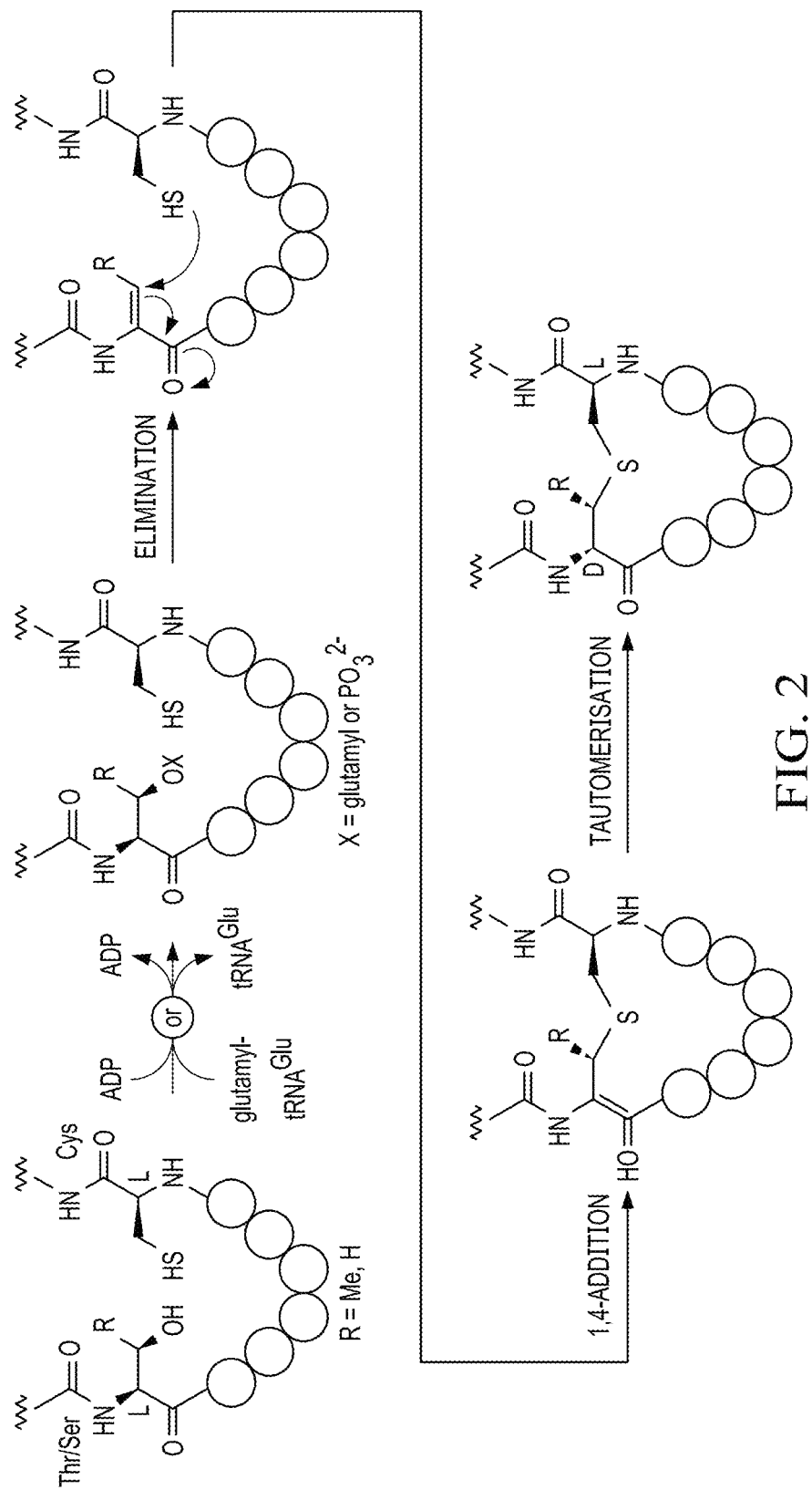
FIG. 2 is a schematic diagram of the chemical reaction in post-translational modification of a lantibiotic as disclosed herein.
Figure 3:
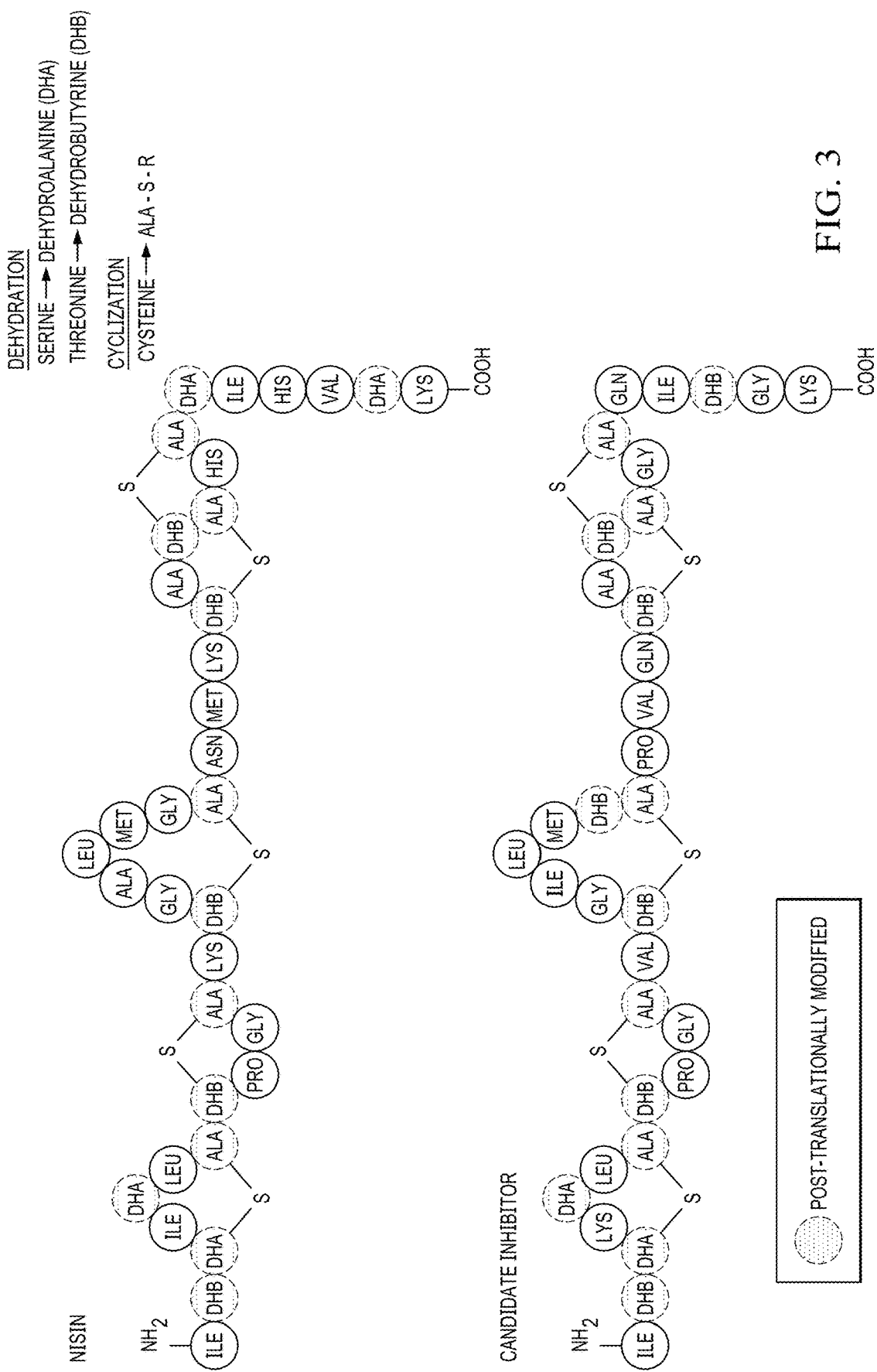
FIG. 3 is a schematic diagram of the amino acid sequence and thioester bonds formed by post-transcriptional modification of a lantibiotic as disclosed herein.

Lantibiotics as disclosed herein can contain thioether cross-links with the general formula $R^1$—S—$R^2$, formed by a serine that has been dehydrated to dehydroalanine (DHA) or threonine that has been dehydrated to dehydrobutyrine (DHB) and cysteine that has been cyclized to alanine with an S—R group, for example by the following reaction of FIG. 2. Lantibiotics as disclosed herein can contain at least one of, at least two of, at least three of, at least four of, or all five of the thioether cross-links depicted in FIG. 3. In particular, lantibiotics as disclosed herein can consist essentially of, consist of, or comprise a domain having the amino acid sequence: Ile Dhb Dha Ile Dha Leu Ala Dhb Pro Gly Ala Lys Dhb Gly Ala Leu Met Gly Ala Val Dhb Gly Ile Leu Met Dhb Ala Pro Val Gln Dhb Ala Dhb Ala Gly Ala Gln Ile Dhb Gly Lys (SEQ. ID. No. 3), also as shown in FIG. 3. The domain can have a thioether cross-link between at least one of, at least two of, at least three of, at least four of, or all five of DHA3 and ALA7, DHB8 and ALA11, DHB13 and ALA19, DHB23 and ALA26, DHB25 and ALA28.

The thioether cross-linked derivative of Dha is often referred to as meso-lanthionine, abbreviated as Lan. The thioether cross-linked derivative of Dhb is often referred to as threo-β-lanthionine, abbreviated as MeLan. Using these abbreviations, lantibiotics as disclosed herein can consist essentially of, consist of, or comprise a domain having the amino acid sequence: Ile Dhb Lan Lys Dha Leu Ala MeLan Pro Gly Ala Val MeLan Gly Ile Leu Met Dhb Ala Pro Val Gln MeLan Ala MeLan Ala Gly Ala Gln Ile Dhb Gly Lys (SEQ. ID. No: 4). The domain can have a thioether cross-link between Lan3 and ALA7, MeLan8 and ALA11, MeLan13 and ALA19, MeLan23 and ALA26, MeLan25 and/or ALA28.

Isolated or purified lantibiotics as described herein also contain or consist of domains produced when lantibiotic genes from the *B. producta* Caballero strain (also sometimes referred to as the MSKCC strain) are expressed in vivo, such as in a *B. producta, E coli* or other bacterial cells, including both naturally occurring and recombinant bacterial cells. The lantibiotic genes can include at least the protein-coding portions of the *B. producta* Caballero strain Lan A precursor peptide gene, the Lan B post-translational dehydration enzyme gene, and the Lan C post-translational cyclization gene. The lantibiotic genes can further include one or any combinations of, including all of the Lan F immunity gene, the Lan E immunity gene, the Lan G immunity gene, the Lan I immunity gene, the Lan K regulatory protein gene, or the Lan T transport protein gene. Sequences for these genes are presented in the Examples. Unless specified to be those particular sequences, the Lan genes include nucleic acids comprising, consisting essentially of, or consisting of those specific sequences; comprising, consisting essentially of, or consisting of variant sequences optimized for expression in a different organism; comprising, consisting essentially of, or consisting of a sequence that, when the nucleic expressed as a protein with the other Lan genes in a microorganism, results in production of a lantibiotic precursor including amino acids having SEQ. ID. No.: 1 or SEQ. ID. No.: 2, or a lantibiotic including amino acids having SEQ. ID. No.: 3 or SEQ. ID. No.: 4; and/or comprising, consisting of, or consisting essentially of a sequence that is at least 95%, at least 98%, or at least 99% homologous to the specific sequence.

In general, lantibiotics as described herein contain or consist of domains having hydrophobic amino acids at the positions relative to the thioether cross-links as indicated in FIG. 3. This results in a generally hydrophobic domain. Lantibiotics can also have cationic amino acids at the positions relative to the thioether cross-links as indicated in FIG. 3.

When lantibiotics as described herein contain rather than consist of the domains described above, any additional amino acids or peptides in the lantibiotics can be non-interfering with the anti-microbial activity exhibited by the domains described above. Additional amino acids or peptide can also enhance anti-microbial activity exhibited by the domains described above, for example by providing additional terminal cationic amino acids. Suitable additional amino acids or peptides include those known for use with lantibiotic domains, particularly a nisin domain.

Lantibiotics as described herein can be 100 amino acids in length or less, 75 amino acids in length or less, 50 amino acids in length or less, 35 amino acids in length or less, 33 amino acids in length or less, between 25 amino acids in length and 33, 35, 50, 75, or 100 amino acids in length, or between 33 amino acids in length and 35, 50, 75, or 100 amino acids in length.

In addition, lantibiotics as described herein can oligomerize, forming at least dimers, trimers, tetramers, and/or pentamers. These oligomers can form after monomers come into contact with a bacterial cell membrane. Further, higher degrees of oligomerization can deform and disrupt the bacterial cell membrane, and thus can exhibit increased anti-microbial effects, such as increased growth inhibition or killing of bacterial cells.

Lantibiotic oligomers as described herein can include only lantibiotics as described herein, or they can include other molecules. In particular, they can include other lantibiotics, such as nisin. They can also include non-peptide linkers between the lantibiotics, such as lipid II linkers.

Without limiting the invention to a particular mode of action, one or more cationic amino acids in lantibiotics as disclosed herein, whether in a domain as described above, or added, for example at a terminus of the domain, can interact with the cell membranes of target bacteria, which is anionic. This can bring the lantibiotic into proximity with the cell membrane or increase its residency time near the cell membrane.

Also without limiting the invention to a particular mode of action, when in proximity to the cell membrane of a target bacteria, a lantibiotic as disclosed herein can bind proteoglycan precursors, such as lipid II, thereby inhibiting cell wall synthesis by the bacteria. The lantibiotic affinity for lipid II can be on the order of $10^7$ $M^{-1}$. The lantibiotic affinity for anionic lipid membranes can be between 1500 $M^{-1}$ and 2000 $M^{-1}$. The portion of the lantibiotic responsive for lipid II binding can be Ile1 through Val12.

Some lantibiotics of the present disclosure can be resistant to heat denaturation; for example they can retain anti-microbial activity even after being subjected to a temperature of 100° C. for ten minutes. Some lantibiotics of the present disclosure can also be resistant to proteolytic degradation. For example, they can not exhibit degradation even after incubation with Proteinase K under conditions sufficient to cause degradation of bovine serum albumin (BSA), as detected via gel electrophoresis or other suitable methods.

Lantibiotic-Producing Bacteria

Therapeutic bacteria of the present disclosure include lantibiotic-producing bacteria, such as naturally occurring, isolated *B. producta* strains that produce a lantibiotic, particularly the Caballero strain, isolated or unisolated recombinant bacteria engineered to produce a lantibiotic, and also supplementary therapeutic bacteria, which are non-lantibiotic-producing, but nevertheless contribute to treatment of gram-positive bacteria, particularly VRE, colonization or infection in a patient. Supplementary therapeutic bacteria include naturally occurring, isolated bacteria as well as isolated or unisolated recombinant bacteria. Supplementary therapeutic bacteria are described in further detail below in the context of pharmaceutical compositions.

Lantibiotic-producing recombinant bacteria of the present disclosure can be produced by introducing an expression vector containing nucleic acids containing one or more lantibiotic genes from the *B. producta* Caballero strain into a bacteria that does not naturally contain the genes. The lantibiotic genes can include at least the protein-coding portions of the *B. producta* Caballero strain Lan A, precursor peptide gene, the Lan B, post-translational dehydration enzyme gene, and the Lan C, post-translational cyclization gene. Sequences for these genes are presented in the Examples. Suitable Lan genes for inclusion in lantibiotic-producing recombinant bacteria include nucleic acids comprising, consisting essentially of, or consisting of those specific sequences; comprising, consisting essentially of, or consisting of variant sequences optimized for expression in a different organism; comprising, consisting essentially of, or consisting of a sequence that, when the nucleic acid expressed as a protein with the other Lan genes in a microorganism, results in production of a lantibiotic precursor including amino acids having SEQ. ID. No.: 1 or SEQ. ID. No.: 2, or a lantibiotic including amino acids having SEQ. ID. No.: 3 or SEQ. ID. No.:4; and/or comprising, consisting of, or consisting essentially of a sequence that is at least 95%, at least 98%, or at least 99% homologous to the specific sequence.

The lantibiotic genes can further include one or any combinations of, including all of, the Lan F immunity gene, the Lan E immunity gene, the Lan G immunity gene, the Lan I immunity gene, the Lan R regulatory protein gene, the Lan K regulatory protein gene, and/or the Lan T transport protein gene. The genes can be in a cluster in a single expression vector, or introduced using multiple expression vectors. The genes can be under common control by one or similar regulatory sequences. The genes can be optimized for expression in the recombinant bacteria.

In addition, some lantibiotic-producing recombinant gram-positive bacteria in the same species, genus, family, or order as the *B. Producta* Caballero strain can already contain one or more, but not all twelve genes identical, at least 95%, but not 100% similar, at least 98%, but not 100% similar, or at least 99%, but not 100% similar or otherwise similar to one or more, but not all twelve of the Lan genes disclosed herein, such that a recombinant copy derived from the *B. Producta* Caballero strain need not be provided in order to obtain a lantibiotic as disclosed herein from the lantibiotic-producing recombinant bacteria.

The lantibiotic-producing recombinant bacteria can be resistant to inhibition by the lantibiotic, either naturally or due to expression of other proteins encoded by exogenous nucleic acids.

Suitable bacteria for use as lantibiotic-producing recombinant bacteria include a *B. producta* strain other than the Caballero strain or otherwise unable to produce a lantibiotic as disclosed herein, *C. scindens*, *B. sartorii*, *E. coli*, *P. distasonis*, *C. bolteae*, *B. hansenii*, *P. capillosus*, *C. hiranonis*, *C. hylemonae*, *C. perfringens*, *C. sordellii*, *P. sphenisci*, Lachnospiraceae 5_1_57E4A, Clostridiales VE202-05, Clostridiales VE202-26, *B. intestihominis*, *C. innocuum*, *A. muciniphila*, *Blautia* unclassified, *E. dolichum*, or bacteria belonging to the *Lactobacillus*, *Lactococcus* or *Bifidobacterium* genera, the Firmicutes phylum, or the Lachnospiraceae family. Other supplementary therapeutic bacteria, supplementary recombination bacteria, or auxiliary therapeutic bacteria as described herein can also be suitable for use as lantibiotic-producing recombinant bacteria. Lantibiotic-producing recombinant bacteria include any bacteria produced as described above. Vectors in lantibiotic-producing recombinant bacteria can encode additional amino acids that are present in the lantibiotic ultimately expressed in addition to the amino acids encoded by the *B. producta* Caballero strain.

In certain examples, the vector can be transferred to the lantibiotic-producing recombinant bacteria by such methods as electroporation, lipofection, calcium phosphate mediated transfection, or viral infection. In general, the method of transfer includes the transfer of a selectable marker to the lantibiotic-producing recombinant bacteria. The cells are then placed under selection to isolate those bacteria that have taken up and are expressing the transferred gene. Those lantibiotic-producing recombinant bacteria can then be delivered to a patient.

Expression of an antibiotic resistance gene by the lantibiotic-producing recombinant bacteria reduces the inhibition in growth or survival of the lantibiotic-producing recombinant bacteria caused by exposure to an antibiotic such as, but not limited to, an antibiotic selected from the group consisting of a beta-lactam antibiotic, clindamycin, a cephalosporin, a quinolone antibiotic, levofloxacin, fluoroquinolone, a macrolide antibiotic, trimethoprim, and a sulfonamide antibiotic, as described herein.

Expression of an antibiotic susceptibility gene by the lantibiotic-producing recombinant bacteria increases the inhibition in growth or survival of the lantibiotic-producing recombinant bacteria caused by exposure to an antibiotic. Such antibiotics can include, but are not limited to, an antibiotic selected from the group consisting of a beta-lactam antibiotic, clindamycin, a cephalosporin, a quinolone antibiotic, levofloxacin, fluoroquinolone, a macrolide antibiotic, trimethoprim, and a sulfonamide antibiotic, as described herein. The lantibiotic-producing recombinant bacteria can be susceptible to an antibiotic other than the foregoing antibiotics.

Expression of a protease or a glycosidase gene by the lantibiotic-producing recombinant bacteria, such as a mucinase gene, increases degradation of a protein or deglycosylation of a protein in a patient, thereby treating gram-positive bacterial, particularly VRE, colonization or infection in the patient directly or by facilitating survival, growth, or protein production by supplementary therapeutic bacteria.

Methods of Producing Lantibiotics

Lantibiotics of the present disclosure can be produced using naturally occurring lantibiotic-producing bacteria or recombinant lantibiotic-producing bacteria.

Lantibiotics of the present disclosure can be produced by culturing naturally occurring lantibiotic-producing *B. producta* (such as the Caballero strain), or by culturing a lantibiotic-producing recombinant bacteria as described above, then isolating and/or purifying the lantibiotic using known techniques, such as size separation, immunoaffinity chromatography, hydrophobic interaction chromatography followed by reverse phase HPLC, and other permutations of cation exchange chromatography, hydrophobic interaction chromatography, and/or reverse phase HPLC. Examples of purification methods are described in Suarez A M, Azcona J I, Rodriguez J M, Sanz B, Hernandez PE. One-step purification of nisin A by immunoaffinity chromatography. Appl Environ Microbiol 1997; 63(12):4990-4992; Mulders J W, Boerrigter I J, Rollema H S, Siezen R J, de Vos W M. Identification and characterization of the lantibiotic nisin Z, a natural nisin variant; Kluskens L D, Kuipers A, Rink R, de Boef E, Fekken S, Driessen A J et al. Post-translational modification of therapeutic peptides by NisB, the dehydratase of the lantibiotic nisin. Biochemistry 2005; 44(38): 12827-12834; Rink R, Wierenga J, Kuipers A, Kluskens L D, Driessen A J, Kuipers O P et al. Dissection and modulation of the four distinct activities of nisin by mutagenesis of rings A and B and by C-terminal truncation. Appl Environ Microbiol 2007; 73(18):5809-5816; Cheigh C I, Kook M C, Kim S B, Hong Y H, Pyun Y R. Simple one-step purification of nisin Z from unclarified culture broth of *Lactococcus lactis* subsp. *lactis* A164 using expanded bed ion exchange chromatography. Biotechnol Lett 2004; 26(17):1341-1345; Lubelski J, Kkhusainov R, Kuipers O P. Directionality and coordination of dehydration and ring formation during biosynthesis of the lantibiotic nisin. J Biol Chem 2009; 284 (38):25962-25972; Uteng M, Hauge H H, Brondz I, Nissen-Meyer J, Fimland G. Rapid two-step procedure for large-scale purification of pediocin-like bacteriocins and other cationic antimicrobial peptdies from complex culture medium. Appl Environ Microbiol 2002; 68(2):952-956. The small peptide purification methods of each of these references is incorporated by reference herein.

Lantibiotics can further be produced in other lantibiotic-producing recombinant cell types, such as recombinant yeast, recombinant plant cells, recombinant animal cells, including insect cells and other recombinant fungal cells, whether from single cellular or multi-cellular fungi. One or more of the Lan genes can be optimized for expression in such an organism. Lantibiotics thus produced can also be isolated and/or purified using the methods described above or other methods appropriate for the organism.

Lantibiotics can further be synthetically produced. Given their small size, they can be particularly amenable to synthetic production. In addition, although synthetic lantibiotics can be isolated or purified if need be, many synthetic methods of peptide production result in isolated or purified peptides, without the need for further isolation or purification steps.

Pharmaceutical Compositions and Devices

Lantibiotic pharmaceutical compositions of the present disclosure contain at least one isolated or purified lantibiotic as disclosed herein. In particular, lantibiotic pharmaceutical compositions, for use in treating a gram-positive bacteria colonization or infection, particularly a target set of or gram-positive bacteria colonization or infection, particularly a VRE colonization or infection, can contain a therapeutically effective amount of at least one isolated or purified lantibiotic as disclosed herein.

Lantibiotics or lantibiotic pharmaceutical compositions can also find use as anti-microbial agents for use other than in a patient, for example as a food additive. In such instances, the lantibiotic or lantibiotic pharmaceutical compositions can contain an amount effective to achieve a desired growth inhibition or death of gram-positive bacteria, particularly a target gram-positive bacteria, as assessed by accepted methods for similar food additives, such as nisin, or the type of food. Such growth inhibition or death can, for instance, be assayed by adding the lantibiotic pharmaceutical compositions and the target gram-positive bacteria to a food sample and incubating the sample in conditions conducive to gram-positive bacteria growth for a given period of time, then assaying for the number of target bacteria in the food sample.

Similarly, lantibiotics or lantibiotic pharmaceutical compositions can also find use as anti-microbial agents for additional uses other than in a patient, such as in cleaning products, including surgical or hand soap, food service and food preparation are cleaners, and hospital or medical disinfectants or cleaners. Lantibiotics or lantibiotic pharmaceutical compositions can particularly find use in anti-microbial coatings or device components, such as coatings on medical devices including surgical instruments, devices for implantation or use in or on patients, such as catheters, tracheotomy tubes, and colostomy bags, and dressings, such as wound dressings, drapes, and other removable or disposable coverings. Gram-positive growth inhibition or death in such contexts can be assayed using methods similar to those used for food.

The present disclosure also includes such devices containing lantibiotics or lantibiotic pharmaceutical compositions as disclosed herein. The lantibiotics or lantibiotic pharmaceutical compositions can be coated on or formed with or within a device.

Pharmaceutical compositions of the present disclosure can include additional therapeutically active agents, such as lantibiotics other than those disclosed herein, such as nisin, or an enzyme that can convert a primary bile acid to a secondary bile acid, for example, 20-alpha-hydroxysteroid dehydrogenase, 7-beta-dehydrogenase, 7-alpha-dehydroxylase, and/or steroid desmolase.

The present disclosure further provides bacterial pharmaceutical compositions, which contain at least one bacteria species in the form of bacterial cells, spores, and/or clusters. Bacterial pharmaceutical compositions can further contain non-bacterial therapeutic agents, such as lantibiotics as described herein, other lantibiotics, such as nisin, or an enzyme that can convert a primary bile acid to a secondary bile acid, for example, 7-α-hydroxysteroid dehydrogenase.

Bacterial pharmaceutical compositions of the present disclosure can comprise, consist essentially of, or consist of any isolated lantibiotic-producing B. producta, such as the Caballero strain, in a formulation suitable for administration to a patient. The lantibiotic-producing B. producta can comprise at least one expressible nucleic acid including a nucleic acid having the sequence of SEQ. ID. No.: 5, 6, 7, 8, 9, 10, 11, 12, 13 and/or 14 and operable to produce a lantibiotic having the sequence of SEQ. ID. No.: 3.

Bacterial pharmaceutical compositions of the present disclosure can comprise, consist essentially of, or consist of an isolated or unisolated lantibiotic-producing recombinant bacteria in a formulation suitable for administration to a patient. The lantibiotic-producing recombinant bacteria can comprise at least one expressible nucleic acid including a nucleic acid having the sequence of SEQ. ID. No.: 5, 6, 7, 8, 9, 10, 11, 12, 13 and/or 14 and operable to produce a lantibiotic having the sequence of SEQ. ID. No.: 3

The bacterial pharmaceutical compositions of the present disclosure can comprise, consist of, or consist essentially of an isolated lantibiotic-producing B. producta as disclosed above in combination with an isolated or unisolated lantibiotic-producing recombinant bacteria as disclosed above in a formulation suitable for administration to a patient.

The bacterial pharmaceutical compositions described herein comprise, consist essentially of, or consist of an isolated lantibiotic-producing B. producta and/or an isolated or unisolated lantibiotic-producing recombinant bacteria and at least one supplementary therapeutic bacteria. The supplementary therapeutic bacteria can be a naturally-occurring, isolated bacteria or a supplementary recombinant bacteria.

All bacteria in the bacterial pharmaceutical composition can be recombinant. All bacteria in the bacterial pharmaceutical composition can be non-recombinant. Other bacterial pharmaceutical compositions can include both recombinant and non-recombinant bacteria Certain supplementary therapeutic bacteria can reduce the risk and/or severity of gram-positive bacteria, particularly VRE, infection or colonization by increasing conversion of a primary bile salt or acid to a secondary bile salt or acid in a site harboring or at risk of harboring the gram-positive bacteria, particularly VRE, such as the gastrointestinal tract. The supplementary therapeutic bacteria produce one or more enzymes that wholly or partially covert a primary bile salt or acid to a secondary bile salt or acid, such as one or more enzymes involved in the 7-α/β-dehydroxylation pathway.

The supplementary therapeutic bacteria can increase the conversion of primary bile salts or acids to secondary bile salts or acids when present in a patient. One or more native proteins produced by one or more supplementary therapeutic bacteria, one or more recombinant proteins produced by one or more supplementary recombinant bacteria, or both can increase the conversion of primary bile salts or acids to secondary bile salts or acids when present in a patient. The one or more native proteins and one or more recombinant proteins can have duplicative and/or complementary functions in conversion of primary bile salts or acids to secondary bile salts or acids when present in a patient.

Enzymes that increase conversion of primary bile acids or salts to secondary bile acids or salts include 20-alpha-hydroxysteroid dehydrogenase, 7-beta-dehydrogenase, 7-alpha-dehydroxylase, and steroid desmolase.

Proteins produced by one or more supplementary therapeutic bacteria can also include beta-lactamase, or one or more additional proteins that confer at least one antibiotic resistance in bacteria, such as resistance to an antibiotic selected from the group consisting of a β-lactam antibiotic, clindamycin, a cephalosporin, a quinolone antibiotic, levofloxacin, fluoroquinolone, a macrolide antibiotic, trimethoprim, and a sulfonamide antibiotic.

Proteins produced by one or more supplementary therapeutic bacteria can also include proteases or glycosidases, such as a mucinase.

The supplementary therapeutic bacteria can comprise, consist of, or consist essentially of C. scindens. Alternate or additional supplementary therapeutic bacteria that can be used in place of C. scindens in the bacterial pharmaceutical compositions described herein include naturally occurring or supplementary recombinant bacteria that express a bai 7-α/β-dehydroxylation operon and produce the peptides resulting therefrom. Specific examples of such naturally occurring supplementary therapeutic bacteria other than C. scindens are C. hiranonis and C. hylemonae (Ridlon, J. Lipid Res. 53:66-76 (2012), Ridlon, J Lipid Res 47, 241-259 (2006)).

The supplementary therapeutic bacteria can comprise, consist of, or consist essentially of a non-lantibiotic producing B. producta bacteria, such as the Honda strain.

The supplementary therapeutic bacteria can comprise, consist of, or consist essentially of both C. scindens and a non-lantibiotic producing B. producta, such as the Honda strain.

Supplementary therapeutic bacteria can comprise, consist essentially of, or consist of C. scindens, a non-lantibiotic producing B. producta, such as the Honda strain, or both and one or more of B. hansenii, P. distasonis, B. sartorii, B. producta, C. innocuum, A. muciniphila, C. bolteae, Blautia unclassified, E. dolichum, members of the Bacteroidetes phylum, such as B. intestihominis (see, e.g., Buffie and Pamer, Nature Reviews Immunology 13:790-801), and/or the Firmicutes phylum or Lachnospiraceae family, such as B. hansenii (ATCC 27752), and/or P. capillosus and/or C. hiranonis, and/or C. hylemonae, and/or C. perfringens, and/or C. sordellii, and/or P. sphenisci, and/or Lachnospiraceae 5_1_57FAA, Clostridiales VE202-05 and/or Clostridiales VE202-26.

A supplementary therapeutic bacteria can be a supplementary recombinant bacteria that produces an enzyme that converts a primary bile salt or acid to a secondary bile salt or acid. Without being bound to any particular theory, a conjugated bile acid is referred to herein as a bile salt. The production of a secondary bile acid from a bile salt involves a two-step process: 1) removal of a conjugated taurine or glycine by a bile salt hydrolase (BSH) enzyme and 2) removal of a hydroxyl group from the steroid ring, for example by enzymes comprising an enzyme encoded by the bai-operon; or oxidation of a hydroxyl group on the steroid ring, for example by a hydroxysterol dehydrogenase enzyme.

The supplementary recombinant bacteria can include one or more exogenous nucleic acids encoding said enzyme, wherein the one or more exogenous nucleic acids are operably linked to a promoter. The promoter can be an inducible promoter or a constitutively active promoter. The promoter can be a bai operon promoter, or can be another promoter active in the supplementary recombinant bacteria.

The supplementary recombinant bacteria can express a bai 7-α/β-dehydroxylation operon, such as the bai operon in C. scindens and can include one or more exogenous nucleic acids encoding a bai 7-α/β-dehydroxylation operon, such as the bai operon in C. scindens, operably linked to a promoter. The "bai 7-α/β-dehydroxylation operon" refers to a cluster of genes encoding enzymes that help convert a primary bile acid to a secondary bile acid. Additional proteins not encoded by the cluster of genes can also play a role in the conversion. For example, the enzymes can convert a primary bile acid such as cholic acid (CA) and/or chenodeoxycholic acid (CDCA), into a secondary bile acid such as deoxycholic acid (DCA) and lithocholic acid (LCA). The enzymes can exhibit dehydroxylation activity. One such enzyme can be a 7-α-hydroxysteroid dehydrogenase, such as a 7α-hydroxysteroid dehydrogenase enzymes produced by C. scindens, C. hiranonis, C. hylemonae, C. perfringens, C. sordellii, P. sphenisci, Lachnospiraceae 5_1_57FAA, Clostridiales VE202-05 and Clostridiales VE202-26, as well as active fragments thereof, and recombinant forms thereof.

The 7-α-hydroxysteroid dehydrogenase can be a C. scindens enzyme having the following amino acid sequence: mrlkdkvilv tastrgigla iaqacakega kvymgarnle rakarademn aaggnvkyvy ndatkeetyv tmieeiieqe gridvlvnnf gssnpkkdlg iantdpevfi ktvninlksv fiasqtavky maengggsii nissvgglip disqiaygts kaainyltkl iavhearhni rcnavlpgmt atdavqdnit ddfrnflkh tpiqrmglpe eiaaavvyfa sddaayttgq iltvsggfgl atpifgdlse rsdarg (SEQ. ID. No.: 15) as set forth in GenBank Accession No. AAB61151, which can be encoded by a nucleic acid having the following sequence: ggccggaatg cagaagttgt ccctggcgtt tttatgaagg cgaccggcat gagatattga acgagacaga ccgggaacag gtatatgaag acctgttcca atggattgaa gatcagaaaa tgacgcagca aaattaggac gctatactta agaaaagtat ccggataatg attacatgaa tatgaaagat atctggaata ctaaaaataa atcatatgga gggattacac atgaggttaa aagacaaagt gattctggtt acagcatcca ccagaggcat tggcctggct atcgctcagg catgtgcgaa agaaggagcc aaagtctaca tgggcgccag gaatctggaa cgcgccaagg cacgggctga cgagatgaat gcggcaggcg gcaatgtaaa gtatgtttac aatgatgcga caaaagaaga gacatacgtg acgatgattg aggaaatcat cgagcaagaa gggcgcatag acgtgcttgt aaataatttc ggctcatcaa atcccaagaa agatcttgga attgccaata cagacccgga ggtattcatc aagacggtaa atatcaacct aaagagcgta tttatcgcaa gccagacggc tgttaagtat atggcggaaa atggaggtgg aagcatcatc aatatctcat ccgtaggagg cctgatacca gatatctctc agattgccta tggaaccagc aaagcggcaa tcaactatct gacgaaactg atagccgtac acgaggcaag gcataacatc agatgcaatg cggtacttcc aggaatgacg gcaacagatg cggtgcagga taatctgacg gatgacttcc gaaacttctt cttgaagcat acgccaattc agcgtatggg gctcccggaa gagatcgcgg cagccgtagt atacttcgca agcgatgatg ccgcatatac cacaggacag attcttaccg tatctggcgg tttcggactg gcaacgccga tatttggaga tctgtctgaa cgctcagatg cccgcgggta gaatttcatg ggttaactta atcaaaagca gaatcaggaa aagagacagc cgggagcggc tgtctcttt atctatagtg cgcctagccg cgcacgtttc taacttttata ggaaagttct cctttcggag aacttgggga ctaaaatagc ccgctcaaaa gcgggcatag tgaatcagac ggtttggatt aaaagatgta aaagccctct tcaccaaaat cgtcatcatc aaggttatca aattcatgta agaaataatc catatccaga agttc (SEQ ID No.:16) as set forth in GenBank Accession No. M58473.

The supplementary recombinant bacteria can contain and express an exogenous nucleic acid encoding SEQ ID No: 15 or an enzyme having one, two, or three conservative substitutions therein, operably linked to a constitutively or inducibly active promoter, as described herein. The supplementary recombinant bacteria can contain and express a nucleic acid comprising SEQ ID No: 16 or a nucleic acid having a sequence that is at least 90 percent, or at least 95 percent, at least 97%, or at least 99 percent homologous thereto (where homology can be determined using standard software such as BLAST or FASTA).

The supplementary recombinant bacteria can contain and express an exogenous nucleic acid encoding an enzyme having the amino acid sequence as set forth in GenBank Accession No. EIA17829 (7-α-hydroxysteroid dehydrogenase from C. perfringens), or an enzyme having one, two, or three conservative substitutions therein, operably linked to a constitutively or inducibly active promoter, as described herein.

The supplementary recombinant bacteria can contain and express an exogenous nucleic acid encoding an enzyme having the amino acid sequence as set forth in GenBank Accession No. AAA53556 (7-α-hydroxysteroid dehydrogenase from *C. sordellii*), or an enzyme having one, two, or three conservative substitutions therein, operably linked to a constitutively or inducibly active promoter, as described herein.

The supplementary recombinant bacteria can further comprises one or more exogenous nucleic acids encoding a bile salt hydrolase, antibiotic resistance gene, an antibiotic susceptibility gene, a protease gene, and/or a glycosidase gene in which the nucleic acids are operably linked to a constitutively or inducibly active promoter, as described herein.

The bile salt hydrolase can be encoded by a bshA and/or bshb gene of a *Lactobacillus acidophilus* (See, e.g., McAuliffe et al., Appl Environ Microbiol. 2005 August; 71(8): 4925-9). Other examples of bile salt hydrolases are described in Begley et al. (Appl Environ Microbiol. 2006 March; 72(3):1729-38).

Expression of an antibiotic resistance gene by the supplementary recombinant bacteria can reduce the inhibition in growth or survival of the supplementary recombinant bacteria caused by exposure to an antibiotic such as, but not limited to, an antibiotic selected from the group consisting of a beta-lactam antibiotic, clindamycin, a cephalosporin, a quinolone antibiotic, levofloxacin, fluoroquinolone, a macrolide antibiotic, trimethoprim, and a sulfonamide antibiotic, as described herein.

Expression of an antibiotic susceptibility gene by the supplementary recombinant bacteria can increases the inhibition in growth or survival of the supplementary recombinant bacteria caused by exposure to an antibiotic. Such antibiotics can include, but are not limited to, an antibiotic selected from the group consisting of a beta-lactam antibiotic, clindamycin, a cephalosporin, a quinolone antibiotic, levofloxacin, fluoroquinolone, a macrolide antibiotic, trimethoprim, and a sulfonamide antibiotic, as described herein. The supplementary recombinant bacteria can be susceptible to an antibiotic other than the foregoing antibiotics.

Expression of a protease or a glycosidase gene by the supplementary recombinant bacteria, such as a mucinase gene, can increases degradation of a protein or deglycosylation of a protein in a patient, thereby treating gram-positive bacteria or VRE colonization or infection in the patient directly or by facilitating survival, growth, or protein production by another therapeutic bacteria.

Bacteria suitable for modification to produce a supplementary recombinant bacteria include *C. scindens, Lactobacillus, Lactococcus*, such as *Lactococcus lactis, Bacillus*, such as *Bacillus subtilis, Bifidobacterium*, such as *Bificobacterium bifidum*, or a non-pathogenic *Listeria*, e.g. an attenuated and non-*monocytogenes Listeria*, such as *Listeria innocua*.

One or more therapeutic bacteria in the bacterial pharmaceutical composition, which can be referred to as auxiliary therapeutic bacteria, can instead facilitate the survival, growth, and/or protein production of a lantibiotic-producing bacteria, a supplementary therapeutic bacteria, a lantibiotic, one or more enzymes that wholly or partially covert a primary bile salt or acid to a secondary bile salt or acid, such as one or more enzymes involved in the 7-α/β-dehydroxylation pathway, or another protein that treats gram-positive bacteria, particularly VRE, colonization or infection, increases resistance to gram positive bacteria, particularly VRE colonization or infection, and/or decreases the severity of gram-positive bacteria, particularly VRE, colonization infection in a patient. For example, an auxiliary therapeutic bacteria can produce beta-lactamase, allowing a lantibiotic-producing bacteria a supplementary therapeutic bacteria, or another auxiliary therapeutic bacteria to survive, grow, and/or produce proteins in the presence of an antibiotic. As an example, *C. bolteae* can facilitate the survival, growth, and/or protein production of *B. producta.*

The bacterial pharmaceutical composition can further comprise one or more probiotic bacteria or probiotic yeast. "Probiotic bacteria" as used herein include any bacteria that have a beneficial effect to a patient when located in the patient's gastrointestinal system, such as a *Lactobacillus* or a *Bifidobacterium*. "Probiotic yeast" as used herein include any yeast that can have a beneficial effect to a patient when located in the patient's gastrointestinal system, such as a *Saccharomyces.*

The supplementary therapeutic bacteria, auxiliary therapeutic bacteria, probiotic bacteria, and/or probiotic yeast can be resistant to inhibition by the lantibiotic, either naturally or due to expression of other proteins encoded by exogenous nucleic acids.

One or more of the bacteria in the bacterial pharmaceutical composition can be in the vegetative state or as spores, or a mixture thereof.

All bacteria described herein, whether recombinant or non recombinant, isolated or in a mixture, can be cultured using techniques known in the art, including techniques to produce bacteria or spores thereof or bacterial clusters suitable for administration to a patient.

Bacterial pharmaceutical compositions as described herein can include a lantibiotic as described herein. The lantibiotic can be added to the composition and can not be the product of a bacteria in the bacterial pharmaceutical composition. Such compositions can lack a lantibiotic-producing bacteria.

Bacterial pharmaceutical compositions as described herein can include a lantibiotic other than as described herein, such as nisin. The lantibiotic can be added to the composition and can not be the product of a bacteria in the bacterial pharmaceutical composition. Such compositions can lack a lantibiotic-producing bacteria.

Bacterial pharmaceutical compositions as described herein can further include an enzyme that can convert a primary bile acid to a secondary bile acid, for example, 7-α-hydroxysteroid dehydrogenase. The enzyme that can convert a primary bile acid to a secondary bile acid, for example, 7-α-hydroxysteroid dehydrogenase. can be added to the composition and can not be the product of bacteria in the bacterial pharmaceutical composition. Such compositions can lack a lantibiotic-producing bacteria.

Pharmaceutical compositions of the present disclosure can further include at least one other agent, such as a stabilizing compound or additional therapeutic agent, and can be administered in any sterile, biocompatible pharmaceutical carrier, including, but not limited to, saline, buffered saline, dextrose, and water. The pharmaceutical compositions can also further include an excipient. The pharmaceutical composition can be in a liquid or lyophilized form and includes a diluent (Tris, citrate, acetate or phosphate buffers) having various pH values and ionic strengths, solubilizer such as Tween® or polysorbate, carriers such as human serum albumin or gelatin, preservatives such as thimerosal, parabens, benzylalconium chloride or benzyl alcohol, antioxidants such as ascorbic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in *Remington's Pharmaceutical Sciences,* 18th ed. A. R. Gennaro, ed. Mack, Easton, PA (1980).

The pharmaceutical compositions of the present disclosure can be formulated using pharmaceutically acceptable carriers well known in the art in dosages suitable for oral, nasogastric, rectal, or topical administration. Such carriers enable the pharmaceutical compositions to be formulated as tablets, pills, capsules, liquids, gels, syrups, slurries, suspensions, enema formulations, and the like. Formulations can include, for example, polyethylene glycol, cocoa butter, glycerol and the like.

Pharmaceutical compositions suitable for use in the present disclosure include compositions where the lantibiotics and/or lantibiotic-producing bacteria are contained in an effective amount to achieve the intended purpose. The effective amount can vary from one individual to another and will depend upon a number of factors, including the overall physical condition of the patient and/or whether the composition is being administered prophylactically.

The pharmaceutical compositions can be administered for prophylactic and/or therapeutic treatments. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Single or multiple administrations of formulations can be given depending on the dosage and frequency as required and tolerated by the patient. The formulations can provide a sufficient quantity of active agent to effectively treat gram-positive bacteria infection, or symptoms or complications thereof as described herein, or to exhibit anti-microbial activity towards gram-positive bacteria.

Pharmaceutical compositions for administration other than to a human can be formulated to be suitable for their intended administration. For example, pharmaceutical compositions intended for administration to a food product can be flavorless or nearly flavorless and/or odorless or nearly odorless, so as to not interfere with enjoyment or consumption of the food product. Pharmaceutical compositions intended for administration as a coating can be formulated to be compatible with coating methods, such as spraying. In some such applications, additives to avoid peptide clumping or degradation can be provided.

In addition, the lantibiotics themselves can contain amino acids that improve their suitability for certain uses.

All pharmaceutical compostions described herein even when not expressly identified as being so composed, can comprise, consist of, or consist essentially of their components.

Methods of Treatment and Use

The present disclosure provides a method of treating a gram-positive bacteria infection, particularly a VRE, *S. aureus, E. faecalis, E. faecium,* and/or *L. monocytogenes* bacteria infection, by administering, to a patient in need of such treatment, an effective amount of a pharmaceutical composition described herein.

The present disclosure further provides a method of reducing and/or inhibiting colonization, for example but not limited to intestinal colonization, of a patient by an undesirable gram-positive bacteria, particularly a VRE, *S. aureus, E. faecalis, E. faecium,* and/or *L. monocytogenes* bacteria, by administering, to a patient in need of such treatment, an effective amount of a pharmaceutical composition described herein.

The present disclosure further includes the use of a pharmaceutical composition described herein to treat a gram-positive bacteria infection, particularly a VRE, *S. aureus, E. faecalis, E. faecium,* and/or *L. monocytogenes* bacteria infection, including at least to prevent infection with the gram-positive bacteria and/or to inhibit growth of the gram-positive bacteria, particularly in patients at risk for gram-positive bacteria infection.

Patients at risk for gram-positive bacteria, particularly VRE, infection or gram-positive bacteria, particularly VRE colonization include individuals who are or have been treated with an antibiotic; individuals who are very young (juvenile) or who are old (geriatric, e.g. humans aged 65 years or older); individuals suffering from an inflammatory bowel disease or condition (including human inflammatory bowel disease IBD, ulcerative colitis or Crohn's Disease); individuals who are hospitalized or in a long-term care facility or who have been, in the past 2, 3, 4, 5, or 6 weeks, hospitalized or in a long-term care facility; individuals with cancer including those undergoing anti-cancer treatment and/or stem cell or bone marrow transplant recipients; individuals who have previously suffered VRE infection or VRE colonization, individuals undergoing immunosuppressive therapy or with an otherwise compromised immune system (e.g. patients infected with an immunodeficiency causing retrovirus such as HIV, FIV, FLV, etc.) and individuals undergoing solid organ transplantation such as liver transplant.

In the case of bacterial pharmaceutical formulations an effective amount of each lantibiotic-producing bacteria or supplementary therapeutic bacteria or an effective amount of total lantibiotic-producing bacteria and supplementary therapeutic bacteria is at least $10^5$ bacteria, or at least $10^6$ bacteria, or at least $10^7$ bacteria, or at least $10^8$ bacteria, or at least $10^9$ bacteria, or between $10^5$ bacteria, $10^6$ bacteria, $10^7$ bacteria, $10^8$ bacteria, or $10^9$ bacteria and $10^{10}$ or $10^{15}$ bacterial.

A patient treated according to the methods and uses herein can be concurrently or sequentially be treated with one or more agent that reduces the risk of and/or ameliorates gram-positive bacteria infection, for example, but not limited to, one or more antibiotic for example, but not limited to, metronidazole, and/or fidaxomicin; an immunotherapeutic agent such as an anti-toxin antibody; an herbal remedy such as Puerariae radix, Scutellariae radix, Rhizoma coptidis, garlic, or one or more extract thereof; and/or a probiotic bacteria or probiotic yeast including for example, but not limited to, *Lactobacillus acidophilus, Lactobacillus casei, Bifidobacteria, Streptococcus thermophilus,* and/or *Saccharomyces boulardii*. The treatment can not further include administration of cholestyramine. The treatment can not further include administration of vancomycin.

The present disclosure further includes a method of reducing gram-positive bacteria in a product other than a product for a patient, such as in a food product and/or the use of a pharmaceutical composition described herein in a product other than a product for a patient, such as a food product by administering, to the food product, an amount of a pharmaceutical composition described herein effective to inhibit growth of gram-positive bacteria. Such a pharmaceutical composition can comprise, consist essentially of, or consist of an isolated or purified lantibiotic as described herein, optionally in a formulation suitable for administration to a patient or to the food or other product.

EXAMPLES

The presently disclosed subject matter will be better understood by reference to the following Examples, which are provided as exemplary of the subject matter, and not by way of limitation. Reference to a particular bacterial strain or strains a "VRE" in these examples and the related figures is made in the context of the experiments described only, and does not imply that only those strains are "VRE" as discussed elsewhere in this specification and claims.

In certain examples, VRE CFU per unit weight of feces or other material is used as a measure of colonization of the patient and hence infection by VRE. Although this is not a direct measure of colonization, it is a well-accepted corollary for colonization.

Example 1: Co-Culture with *B. producta* Inhibits VRE Growth $10^7$ CFU/mL *B. Producta, C. bolteae, P. distasonis*, or *B. sartorii* and $10^3$ CFU/mL VRE were cultured in BHIS liquid medium (Brain Heart Infusion (BHI)+5 g/L yeast extract+1 g/L L-cysteine) for 6, 24, 48, or 72 hours anaerobically at 37° C. VRE colony forming units (CFU) were quantitated and results are presented in FIG. 4 and FIG. 5.

Figure 4:
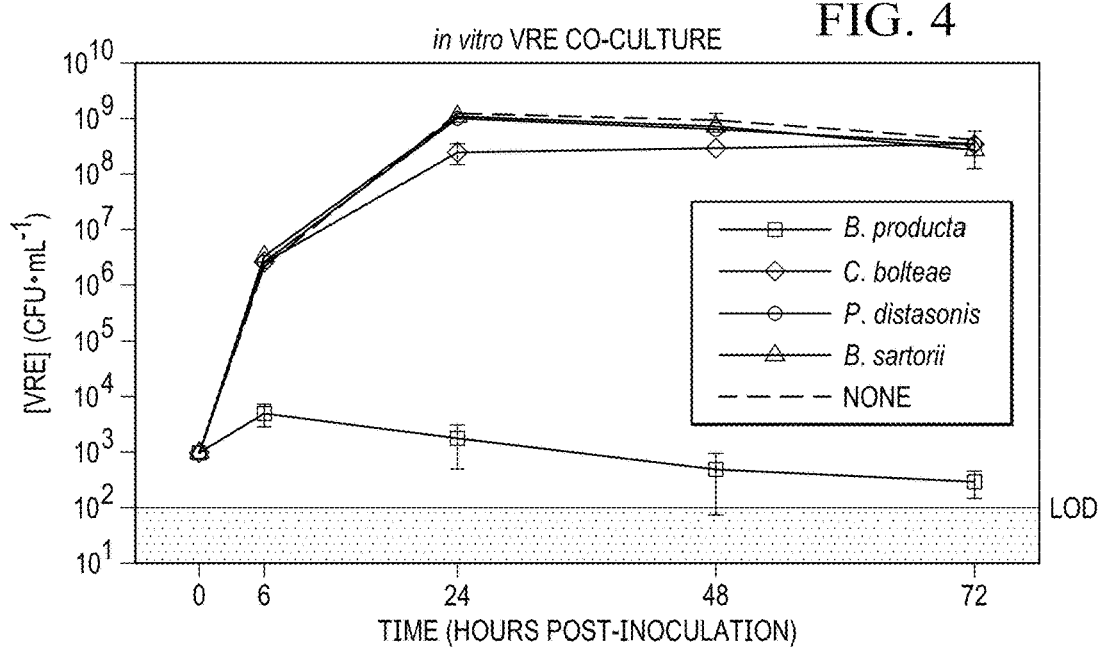
FIG. 4 is a graph of the effects of co-culture with various bacteria including *B. producta* on VRE.
Figure 5:
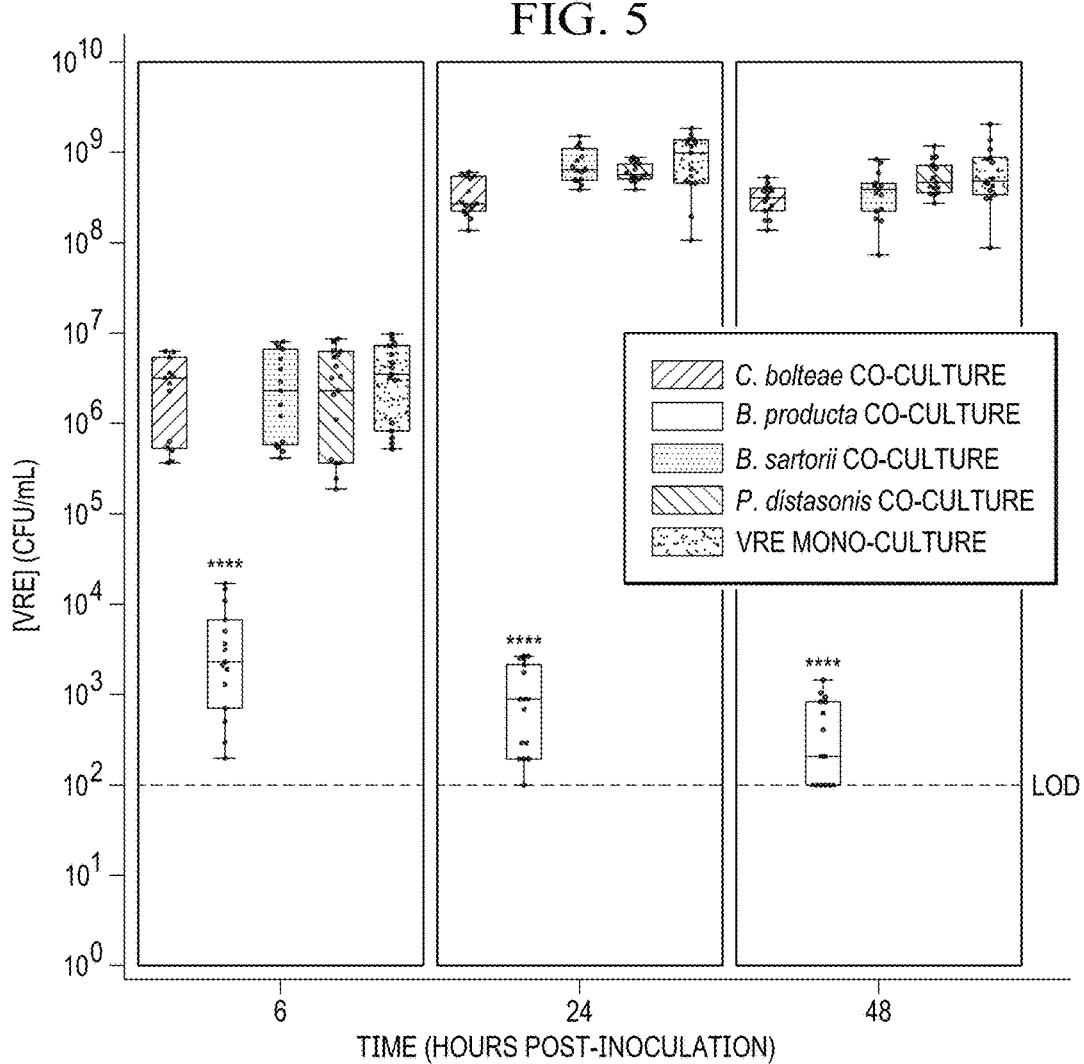
FIG. 5 is a set of graphs of the effects of co-culture with various bacteria including *B. producta* on VRE.

Based upon the data in both FIG. 4 and FIG. 5, *B. producta* inhibited VRE, while the other three bacterial strains tested did not. In addition, *B. producta* was is necessary and sufficient to inhibit VRE growth in vitro.

Figure 6:
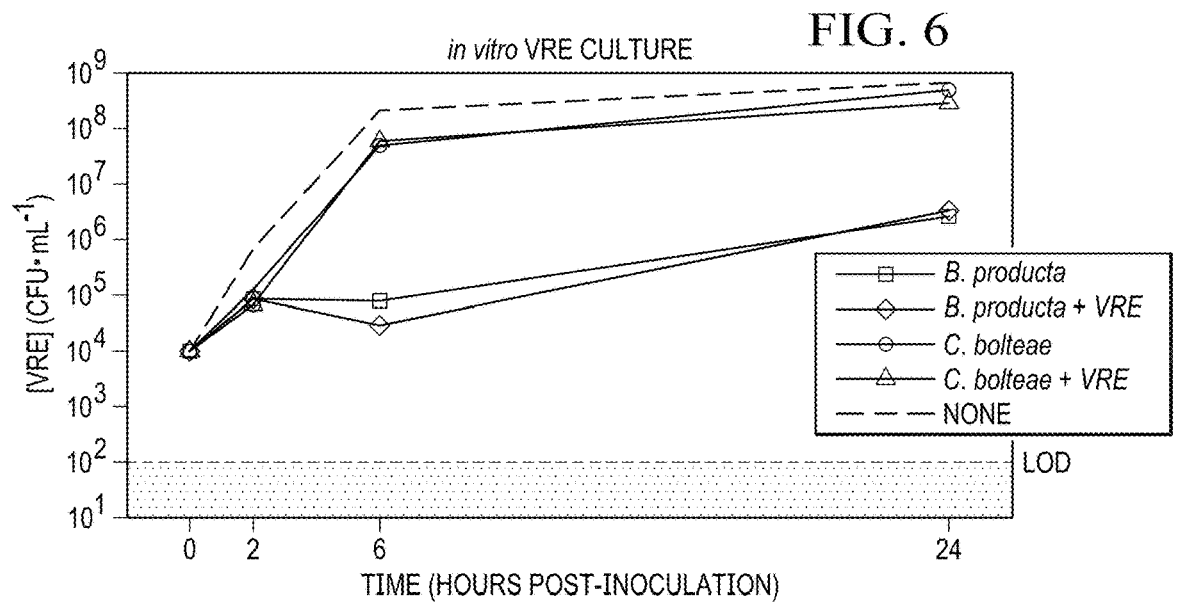
FIG. 6 is a graph of the effects on VRE of supernatant from mono or VRE co-cultures of *B. producta* and *C. bolteae*.
Figure 7:
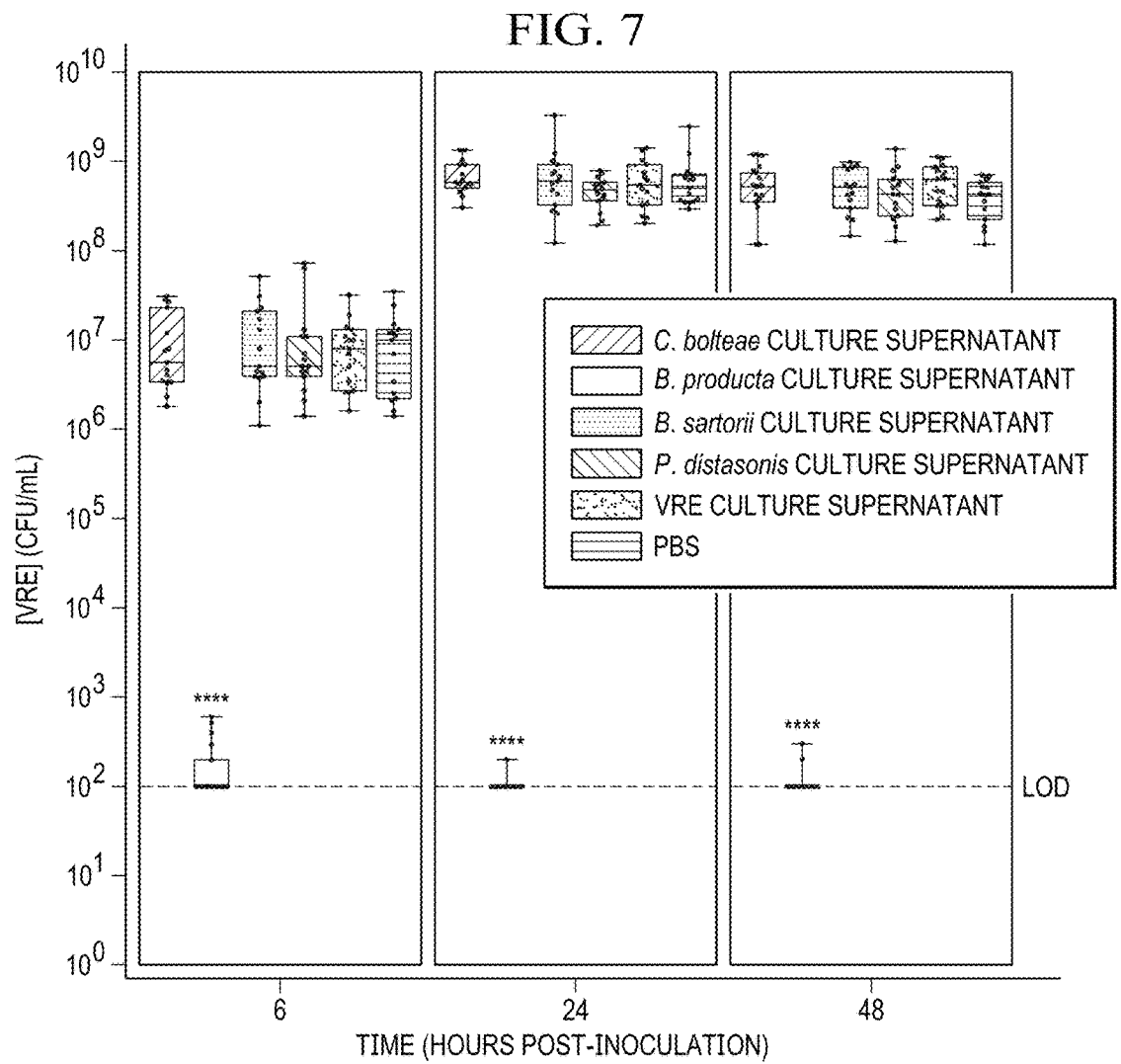
FIG. 7 is a set of graphs of the effects on VRE of supernatant from cultures of *B. producta* and other bacteria.

Example 2: Cell-Free Supernatant from *B. producta* Cultures Inhibit VRE Growth $10^7$ CFU/mL *B. producta* or *C. bolteae*±$10^3$ CFU/mL VRE were cultured in BHIS for 6 hours anaerobically at 37° C. The culture supernatants were filtered through a 0.22 µm filter. $10^3$ CFU/mL VRE were cultured in the filtered culture supernatants for 2, 6, or 24 hours anaerobically at 37° C. VRE CFU were quantitated and results are presented in FIG. 6. *B. producta* supernatant inhibited VRE, whether originally cultured with or without VRE, while *C. bolteae* supernatant did not. This indicates that a factor secreted by *B. producta* inhibits VRE. $10^7$ CFU/mL *B. producta, C. bolteae, P. distasonis*, or *B. sartorii* were cultured in BHI overnight (at least 8 hours) anaerobically at 37° C. The culture supernatants were filtered through a 0.22 µm filter and diluted 1:2 in fresh BHIS. $10^3$ CFU/mL VRE were cultured in the filtered culture supernatants for 2, 6, or 24 hours anaerobically at 37° C. VRE CFU were quantitated and results are presented in FIG. 7.

This indicates that a factor secreted by *B. producta* inhibits VRE and further that production of the factor is not dependent on the presence of VRE.

Figure 8:
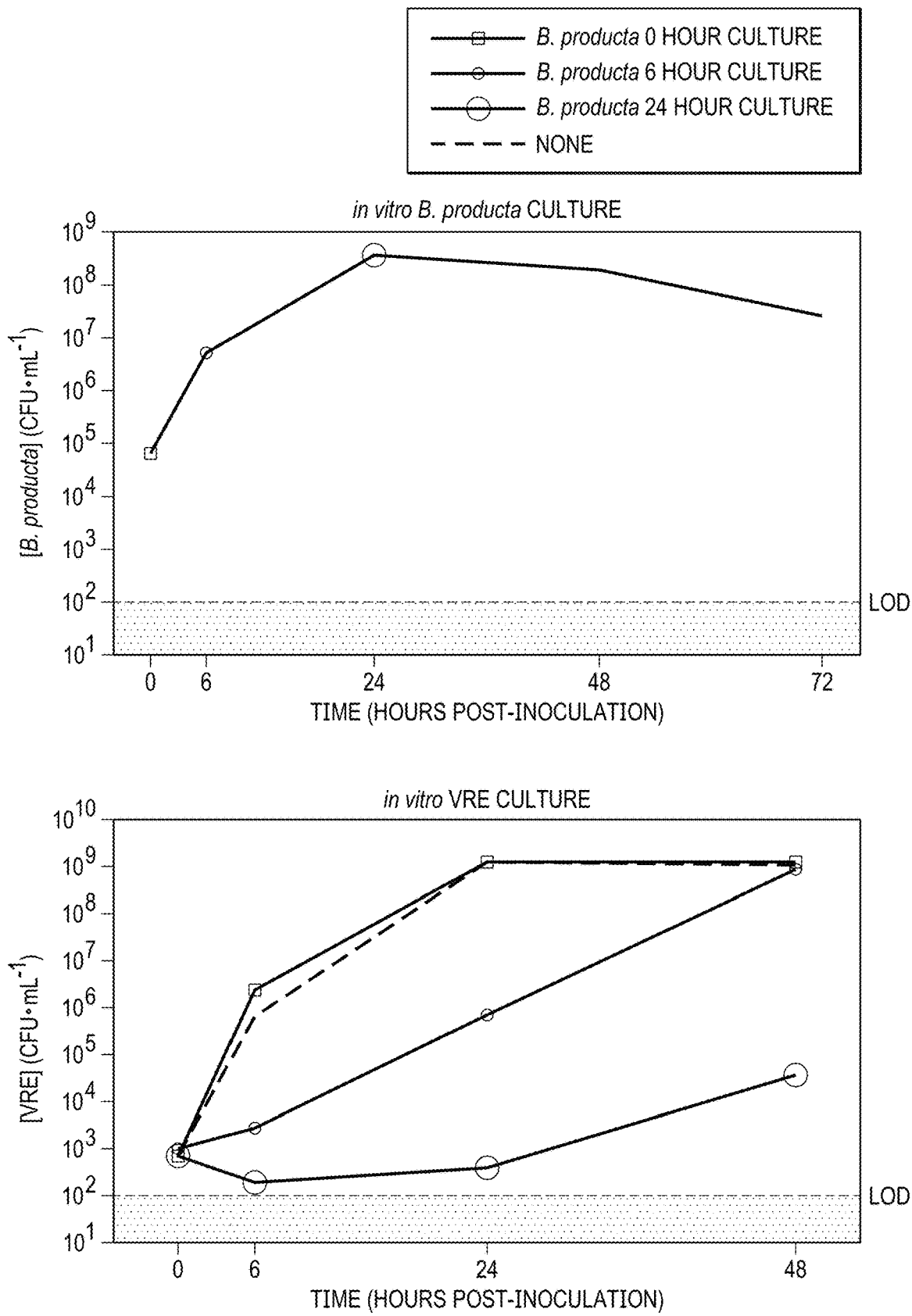
FIG. 8 is a set of graphs of the growth of *B. producta* in a culture (left panel) and the effects of a *B. producta* factor (which is a lantibiotic according to this disclosure) from the culture on VRE (right panel)

Example 3: *B. producta* Produces a Factor to Inhibit VRE Growth Rather than Depleting a Factor $10^7$ CFU/mL *B. producta* was cultured for 0, 6, 24 hours in BHIS anaerobically at 37° C. Culture growth was verified by quantitating *B. producta* CFU at 6, 24, 48, and 72 hours. Results are presented in FIG. 8, left panel and show that *B. producta* growth peaked at 24 hours. The culture supernatant at 0, 6, and 24 hours was filtered through a 0.22 µm filter, then concentrated by ultrafiltration with a molecular weight cut off greater than 100 kDa. The concentrated culture supernatant was then diluted to the original volume with fresh BHIS culture medium. Concentrated/diluted medium was inoculated with $10^3$ CFU/mL VRE and cultured anaerobically at 37° C. for 6, 24, 48 hours. VRE CFU were quantitated and results are presented in FIG. 8, right panel.

VRE was not inhibited by culture supernatant prior to culture of *B. producta*, but it was inhibited by culture supernatant after both 6 hours and 24 hours of *B. producta* culture, with greater inhibition at 24 hours, indicating that the inhibitory factor is produced by *B. producta* during both early and later stages of growth. In addition, because the *B. producta* culture supernatant inhibited VRE growth, even when concentrated and added to fresh medium, *B. producta*'s effect was not a result of depletion of a medium factor, such as a nutrient, as such a factor would have been resupplied by the fresh medium.

Figure 9:
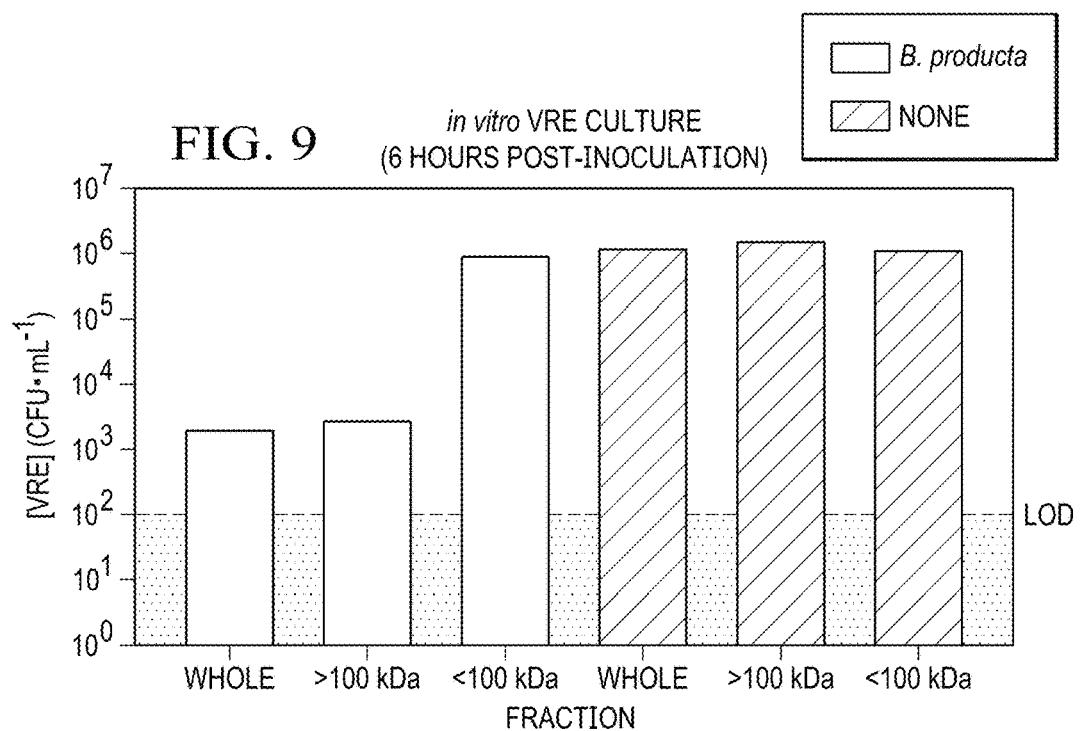
FIG. 9 is a graph of the effects of size-separated *B. producta* culture products on VRE.

Example 4: *B. producta* Produces a Soluble Molecule that Inhibits VRE Growth $10^7$ CFU/mL *B. producta* were cultured for 24 hours anaerobically at 37° C. in BHIS. The culture supernatant was filtered through a 0.22 µm filter, then concentrated by ultrafiltration with a molecular weight cut off greater than 100 kDa. The greater than 100 kDa concentrated culture supernatant fraction was diluted to its volume with fresh culture medium. It was then further diluted 1:1 with additional fresh culture medium. The less than 100 kDA culture supernatant fraction was also diluted 1:1 with fresh culture medium. Samples were inoculated with $10^3$ CFU/mL VRE and cultured for 6 hours anaerobically at 37° C. VRE CFU were quantitated and results are presented in FIG. 9.

Both whole culture supernatant and the culture supernatant fraction with a molecular weight cut off greater than 100 kDa inhibited VRE growth, whereas the less than 100 kDa culture supernatant fraction did not, indicating that the VRE-inhibiting factor had a size of greater than 100 kDa and is soluble (i.e. not bound to the bacteria).

Figure 11:
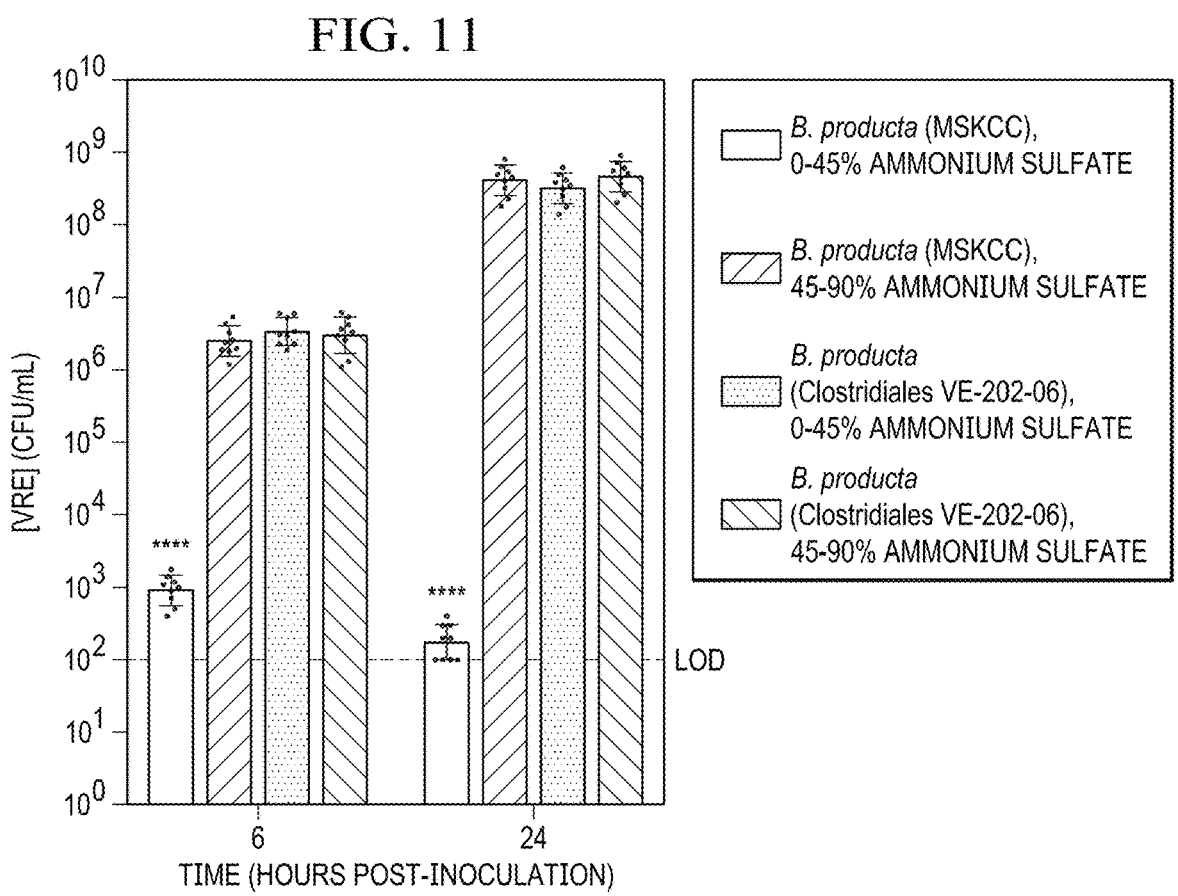
FIG. 11 is graph of the effects of various ammonium sulfate precipitates from *B. producta* cultures on VRE.
Figure 10:
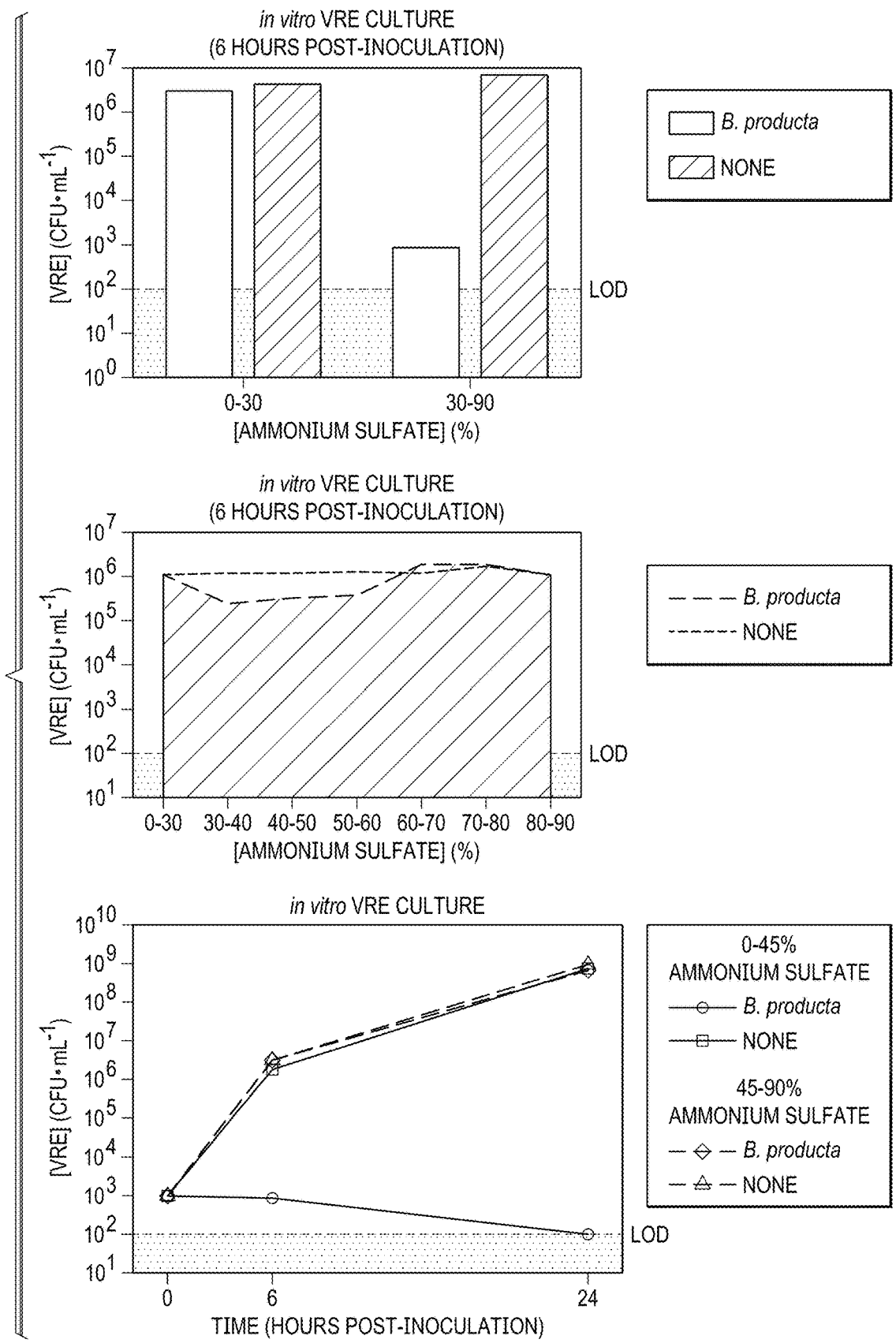
FIG. 10 is a set of graphs of the effects of various ammonium sulfate precipitates from a *B. producta* culture on VRE.

Example 5: VRE Inhibition is Preserved by Ammonium Sulfate Protein Precipitation of *B. producta* Cultures $10^7$ CFU/mL *B. producta* was cultured for 24 hours anaerobically at 37° C. in BHIS. The culture supernatant was filtered through a 0.22 µm filter. Ammonium sulfate was added to the filtered culture supernatant at varying concentrations to precipitate proteins. Precipitated proteins were resolubilized in phosphate buffered saline (PBS) (2 mg/mL) and dialyzed. The dialyzed protein was returned to the original culture volume with fresh culture medium and samples were innoculated with $10^3$ CFU/mL VRE and cultured for 6 or 24 hours anaerobically at 37° C. VRE CFU were quantitated and results are presented in FIG. 10. The results indicate that a factor generally precipitated at higher ammonium sulfate concentrations, such as 45-90%, particularly at least 60%, is responsible for VRE-inhibition. $10^7$ CFU/mL *B. producta* was cultured for 24 hours anaerobically at 37° C. in BHIS. The culture supernatant was filtered through a 0.22 µm filter. Ammonium sulfate was added to the filtered culture supernatant at varying concentrations to precipitate proteins. Precipitated proteins were resolubilized in phosphate buffered saline (PBS) (2 mg/mL) and dialyzed (the dialyzed protein was returned to the original culture volume with PBS) and samples were innoculated with $10^3$ CFU/mL VRE and cultured for 6 or 24 hours anaerobically at 37° C. VRE CFU were quantitated and results are presented in FIG. 11.

The B. producta factor isolated with 0-45% ammonium sulfate inhibited VRE.

Figure 12:
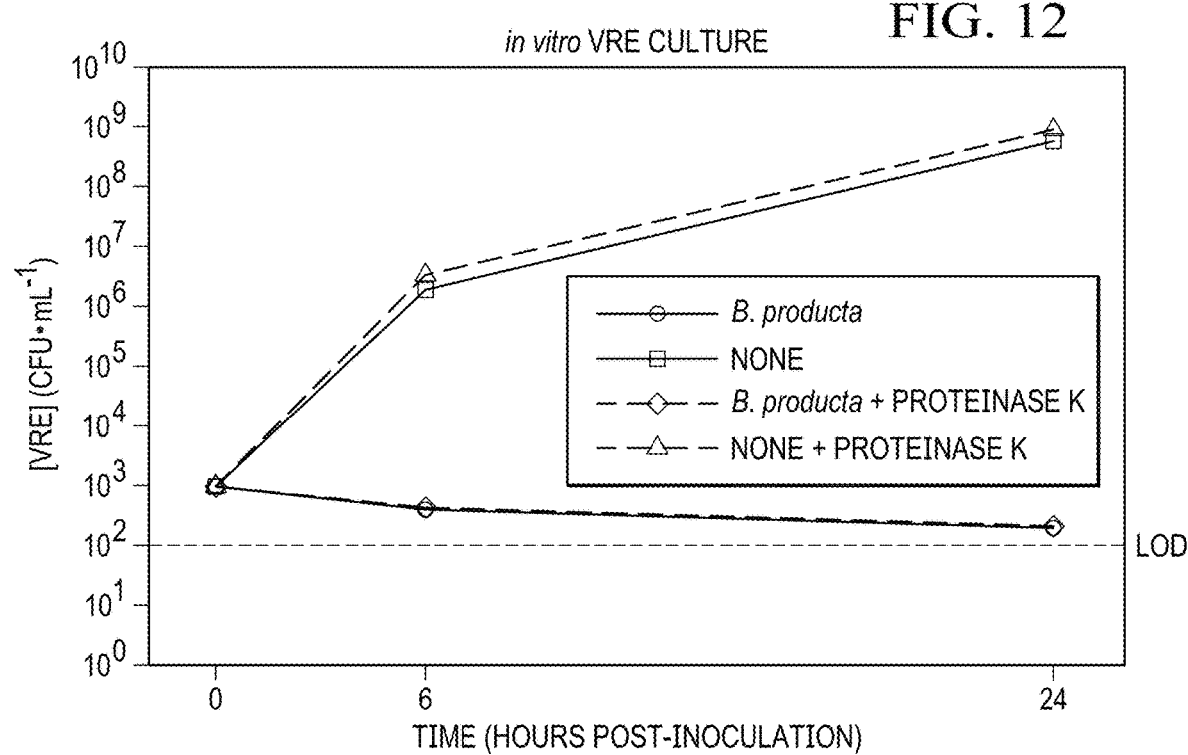
FIG. 12 is a graph of the effects of Proteinase K on the *B. producta* factor's (which is a lantibiotic according to this disclosure) effects on VRE.

Example 6: VRE Inhibition is Preserved after Proteinase K Digestion of B. producta Culture $10^7$ CFU/mL B. producta was cultured for 24 hours anaerobically at 37° C. in BHIS. The culture supernatant was filtered through a 0.22 μm filter. 45% ammonium sulfate was added to the filtered culture supernatant to precipitate proteins. The precipitate was resolubilized in PBS (2 mg/mL), then dialyzed. The dialyzed protein was incubated with Proteinase K (1 mg/mL) for 1 hour at 37° C. These conditions are sufficient to completely digest BSA at a concentration of 100 μg/m, as evidenced by the formation of continuous bands in gel electrophoresis. The dialyzed protein/proteinase K solution was returned to its original volume in fresh culture medium and inoculated with $10^3$ CFU/mL VRE the cultured for 6 or 24 hours anaerobically at 37° C. VRE CFU were quantitated and results are presented in FIG. 12.

The B. producta factor was able to inhibit VRE even after exposure to Proteinase K.

Figure 13:
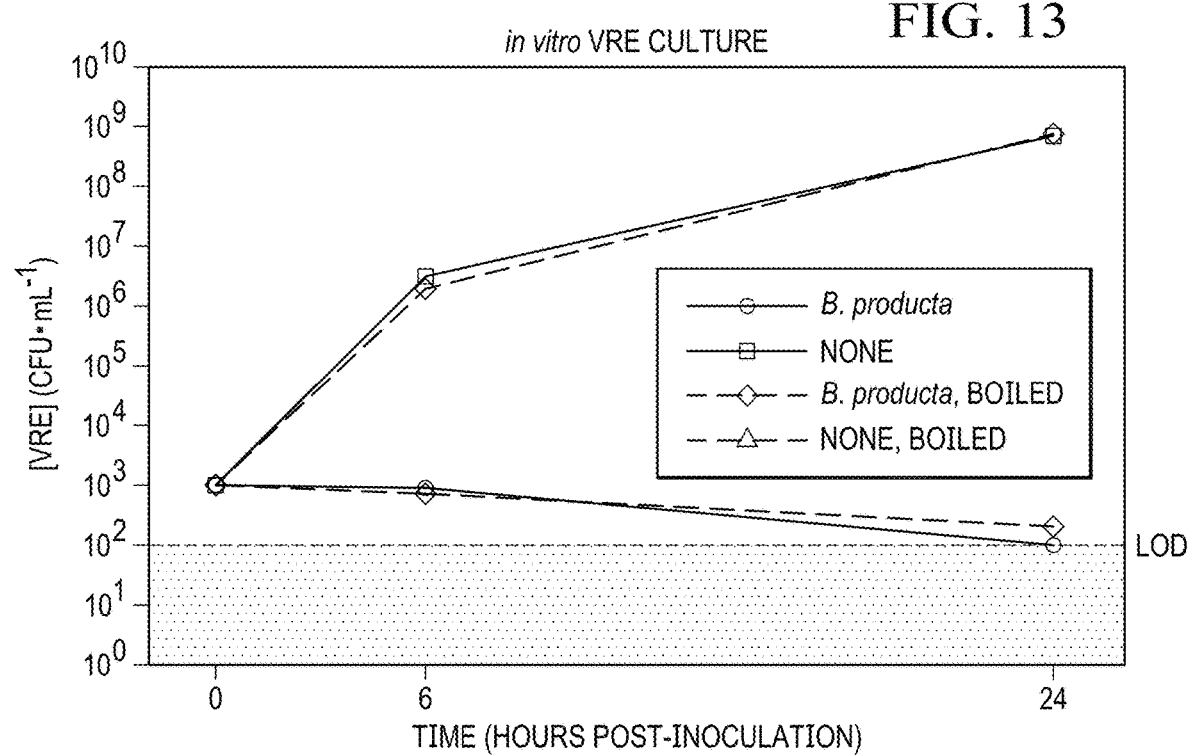
FIG. 13 is a graph of the effects of a temperature of 100° C. on the *B. producta* factor's (which is a lantibiotic according to this disclosure) effects on VRE.

Example 7: VRE Inhibition is Preserved after Boiling B. producta Culture $10^7$ CFU/mL B. producta was cultured for 24 hours anaerobically at 37° C. in BHIS. The culture supernatant was filtered through a 0.22 μm filter. 45% ammonium sulfate was added to the filtered culture supernatant to precipitate proteins. The precipitate was resolubilized in PBS (2 mg/mL), then dialyzed. The dialyzed protein was incubated at 100° C. for ten minutes. The heated, dialyzed protein solution was returned to its original volume in fresh culture medium and inoculated with $10^3$ CFU/mL VRE the cultured for 6 or 24 hours anaerobically at 37° C. VRE CFU were quantitated and results are presented in FIG. 13.

The B. producta factor was able to inhibit VRE even after exposure to boiling temperatures.

Figure 14:
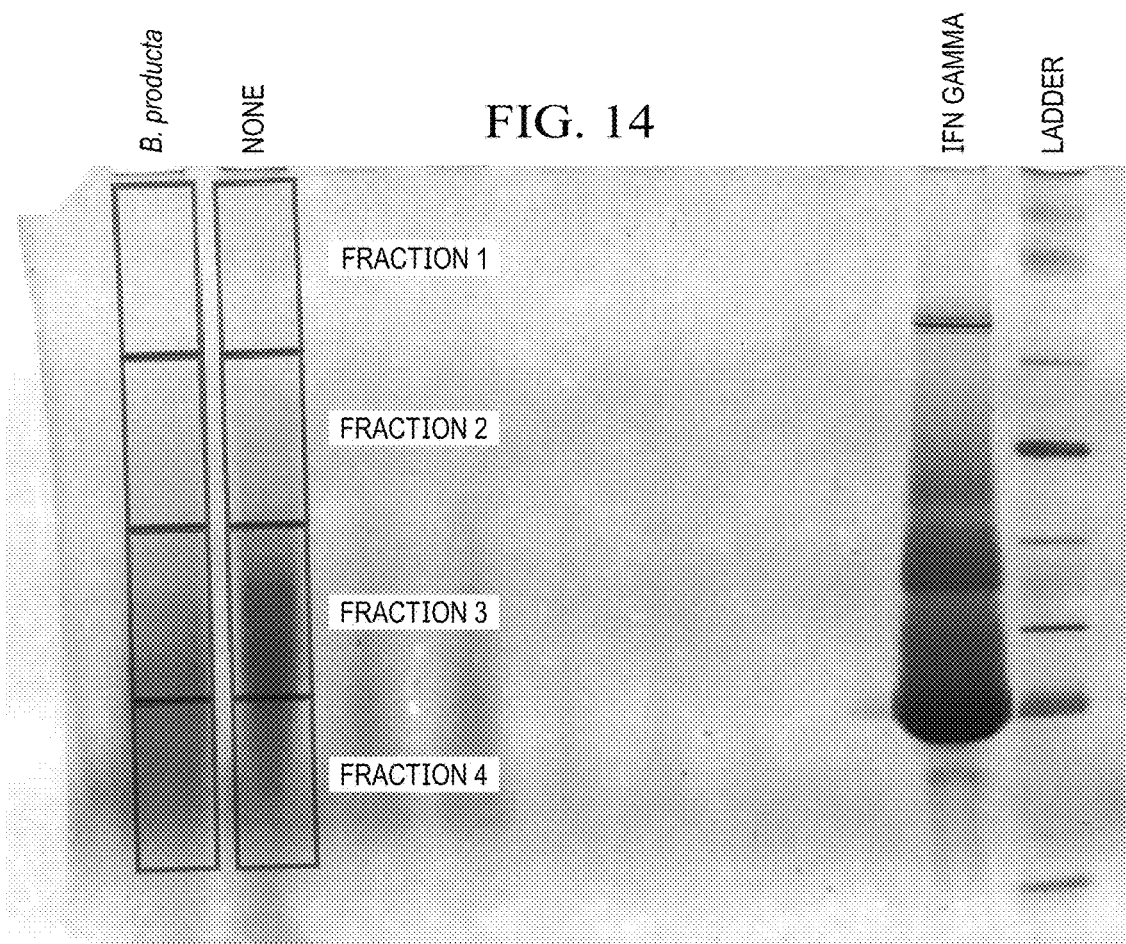
FIG. 14 is a photograph of a Coomassie blue stained gel with electrophoretically separated *B. producta* culture products.
Figure 15:
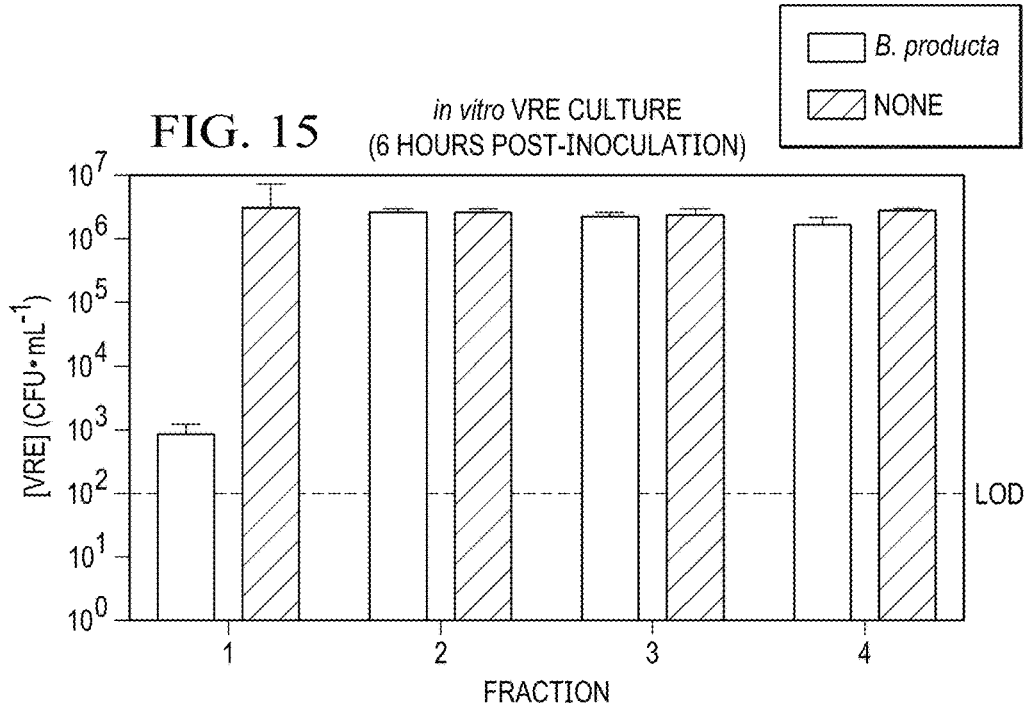
FIG. 15 is a graph of the effects on VRE of various fractions of the gel of FIG. 14.

Example 8: VRE Inhibition is Preserved by NATIVE PAGE Gel Extraction from B. producta Cultures $10^7$ CFU/mL B. producta was cultured for 24 hours anaerobically at 37° C. in BHIS. The culture supernatant was filtered through a 0.22 μm filter. 45% ammonium sulfate was added to the filtered culture supernatant to precipitate proteins. The precipitate was resolubilized in PBS (2 mg/mL), then dialyzed. The dialyzed protein was subjected to non-denaturing polyacrylamide gel electrophoresis (NATIVE PAGE). The resulting gel was stained with Coomassie blue and each lane was divided into four fractions as indicated in FIG. 14. Each fraction was extracted and the extracts were concentrated. The concentrated gel extracts were diluted 1:5 with fresh culture medium and inoculated with $10^3$ CFU/mL VRE the cultured for 6 or 24 hours anaerobically at 37° C. VRE CFU were quantitated and results are presented in FIG. 15.

The VRE-inhibitory factor was present in the first fraction of the gel, in which the smallest size proteins and peptides were present.

Figure 16:
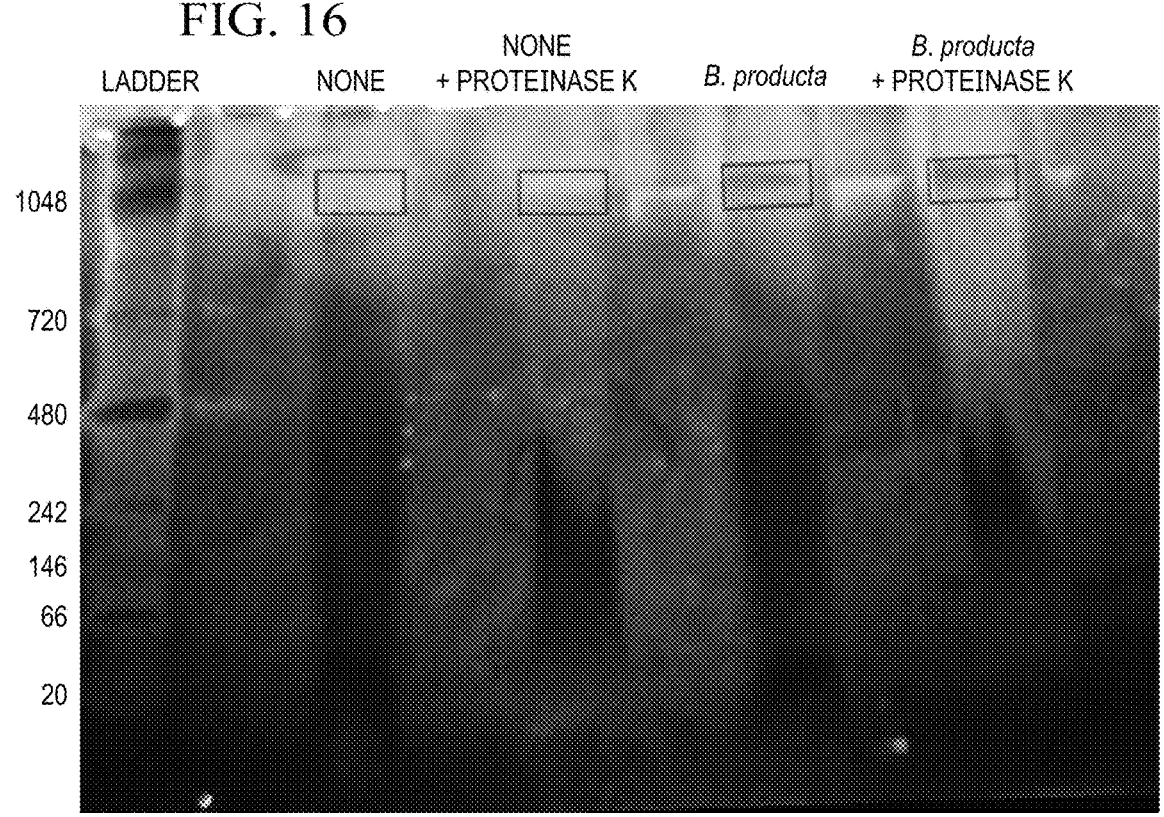
FIG. 16 is a photograph of a silver stained gel with electrophoretically separated *B. producta* culture products treated or untreated with Proteinase K.
Figure 17:
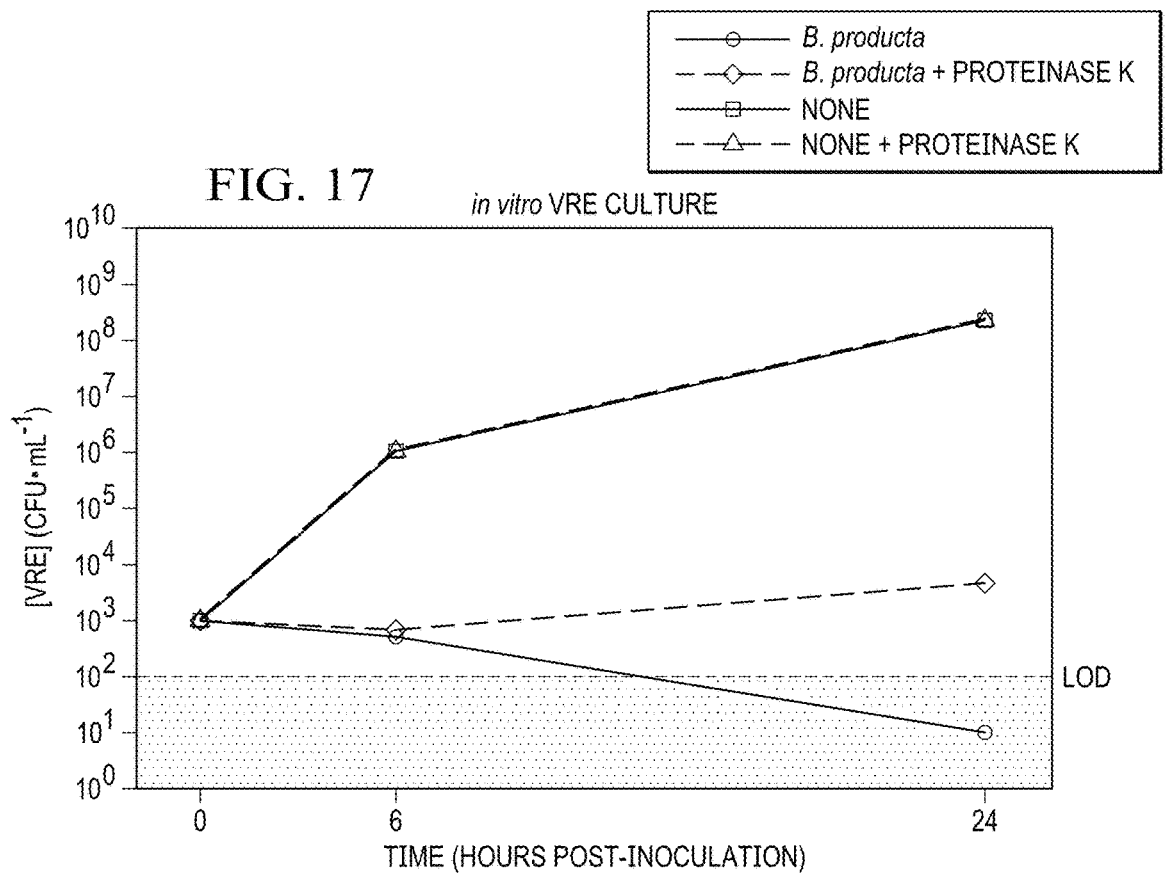
FIG. 17 is a graph of the effects on VRE of various bands corresponding to bands in the gel of FIG. 16.

Example 9: VRE Inhibition is Preserved by NATIVE PAGE Gel Extraction from B. producta Cultures Subjected to Proteinase K $10^7$ CFU/mL B. producta was cultured for 24 hours anaerobically at 37° C. in BHIS. The culture supernatant was filtered through a 0.22 μm filter. 45% ammonium sulfate was added to the filtered culture supernatant to precipitate proteins. The precipitate was resolubilized in PBS (2 mg/mL), then dialyzed. The dialyzed protein was subjected to Proteinase K digestion as described in Example 6, followed by non-denaturing polyacrylamide gel electrophoresis (NATIVE PAGE) on two gels. One resulting gel was stained with silver and a band of interest was identified. (FIG. 16.) Corresponding regions of the unstained gel were extracted and the extracts were concentrated. The concentrated gel extracts were diluted 1:5 with fresh culture medium and inoculated with $10^3$ CFU/mL VRE the cultured for 6 or 24 hours anaerobically at 37° C. VRE CFU were quantitated and results are presented in FIG. 17.

The VRE-inhibitory factor was present in the first fraction of the gel, in which the smallest size proteins and peptides were present.

Figure 18:
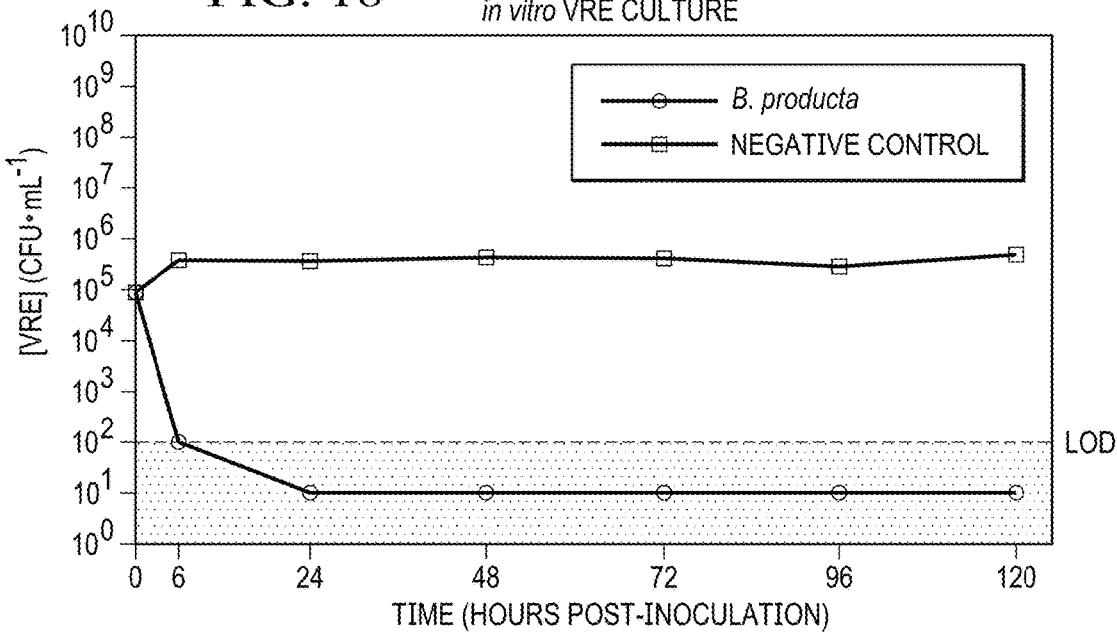
FIG. 18 is a graph of the effects on VRE of the *B. producta* factor when cultured in PBS (which is a lantibiotic according to this disclosure)

Example 10: VRE Clearance In Vitro and In Vivo Suggests the Inhibitor is Bactericidal $10^7$ CFU/mL B. producta was cultured for 24 hours anaerobically at 37° C. in BHIS. The culture supernatant was filtered through a 0.22 μm filter. Ammonium sulfate was added to the filtered culture supernatant at varying concentrations to precipitate proteins. Precipitated proteins were resolubilized in phosphate buffered saline (PBS) (2 mg/mL) and dialyzed. The dialyzed protein was returned to the original culture volume with supplemented PBS (the dialyzed protein was returned to the original culture volume with PBS) and samples were innoculated with $10^5$ CFU/mL VRE and cultured for 6, 24, 48, 72, 96, or 120 hours anaerobically at 37° C. VRE CFU were quantitated and results are presented in FIG. 18. A permanent decline in the number of VRE was observed, indicating that not only does the B. producta factor inhibit VRE growth, it also kills VRE. 6-8 week old, C57BL/6 mice were administered ampicillin (0.5 g/L) in the drinking water for 5 days, and subsequently orally gavaged with VRE ($10^4$ CFU). Bacterial consortia for oral gavage were prepared by individually culturing the B. producta Caballero strain or the B. producta, Honda strain, on Columbia base medium (agar, peptones, cornstarch) plus 5% sheep blood agar plates, anaerobically at 37° C. overnight. Each isolate was subsequently harvested and resuspended in reduced phosphate buffered saline (PBS) to a final concentration of $10^8$ CFU/mL. Three days after VRE administration, a bacterial consortia transplant was orally gavaged ($10^7$ CFU per bacterial isolate). Fecal pellets were collected 0, 5, 10 days after bacterial consortia transplant, and VRE was quantitated.

Figure 19:
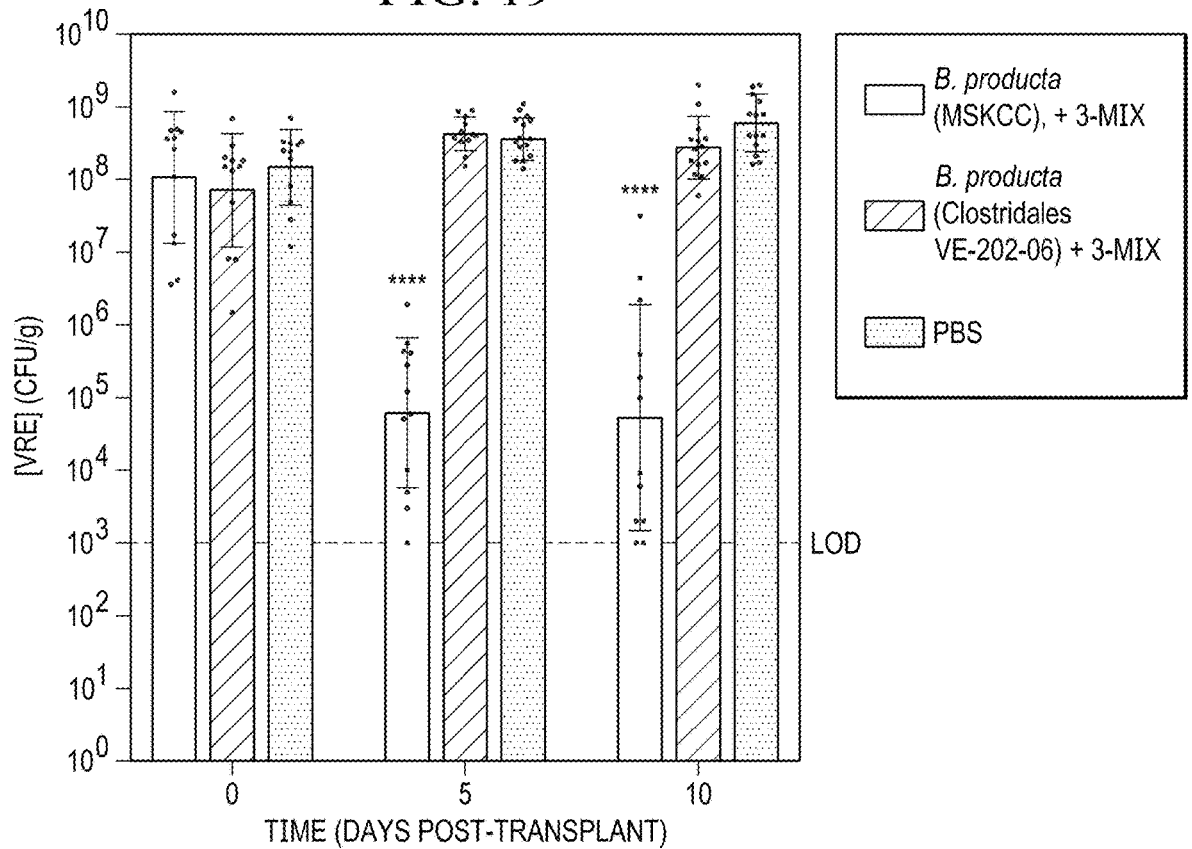
FIG. 19 is a graph showing the effects of different *B. producta* stains on VRE growth in vivo.

Results, presented in FIG. 19, show that B. producta (Caballero strain), but not the Honda strain inhibited VRE in vivo.

6-8 week old, C57BL/6 mice were administered ampicillin (0.5 g/L) in the drinking water for 5 days, and subsequently orally gavaged with a bacterial consortia ($10^7$ CFU per bacterial isolate). Bacterial consortia for oral gavage were prepared by individually culturing the *B. producta* Caballero strain, or the *B. producta* Honda strain, on Columbia base medium (agar, peptones, cornstarch) plus 5% sheep blood agar plates, anaerobically at 37° C. overnight. Each isolate was subsequently harvested and resuspended in reduced phosphate buffered saline (PBS) to a final concentration of $10^8$ CFU/mL. 7 days post-transplant, cecal content was harvested and resuspended in PBS to a final concentration of 100 mg/mL. Cecal supernatant was collected by filtration through a 0.22 μm filter. VRE inoculated at $10^3$ CFU/mL in the cecal supernatant and incubated at 37° C. aerobically. VRE was cultured for 6 hours and quantitated.

Figure 20:
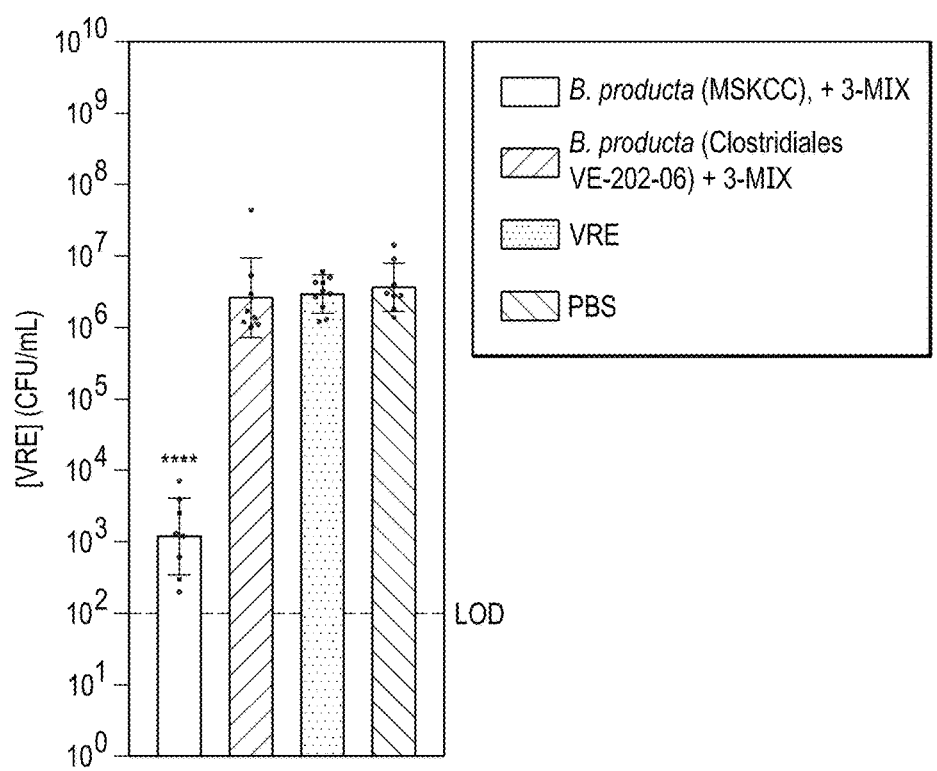
FIG. 20 is a graph showing the effects of the supernatant from the cecum of mice colonized with different *B. producta* strains on VRE growth in culture.

Results in FIG. 20 show that the *B. producta* factor produced in vivo inhibits VRE.

Example 11: Microscopy Shows VRE Lysis, Compromised Viability, and Compromised Cell Walls $10^7$ CFU/mL *B. producta* was cultured for 24 hours anaerobically at 37° C. in BHIS. The culture supernatant was filtered through a 0.22 μm filter. Ammonium sulfate was added to the filtered culture supernatant at varying concentrations to precipitate proteins. Precipitated proteins were resolubilized in phosphate buffered saline (PBS) (2 mg/mL) and dialyzed. The dialyzed protein was returned to the original culture volume with supplemented PBS (the dialyzed protein was returned to the original culture volume with PBS) and samples were innoculated with $10^8$ CFU/mL VRE and cultured for 24 hours anaerobically at 37° C. Bacteria were fixed onto slides for microscopy.

Figure 21:
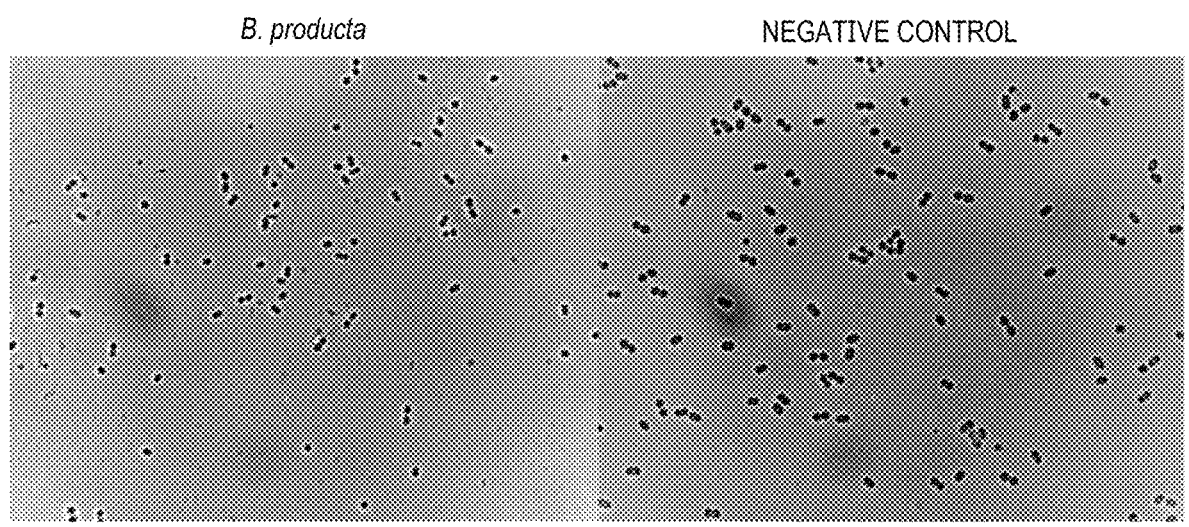
FIG. 21 is a micrograph of VRE grown in the presence or absence of the *B. producta* factor (which is a lantibiotic according to this disclosure)

FIG. 21 shows phase contrast microscopy results for VRE subjected to the *B. producta* factor (left panel), as compared to the control (right panel). The VRE subjected to the *B. producta* factor were smaller, less numerous, more frequently in a single coccus arrangement and surrounded by more cellular debris as compared to the control.

Figure 22:
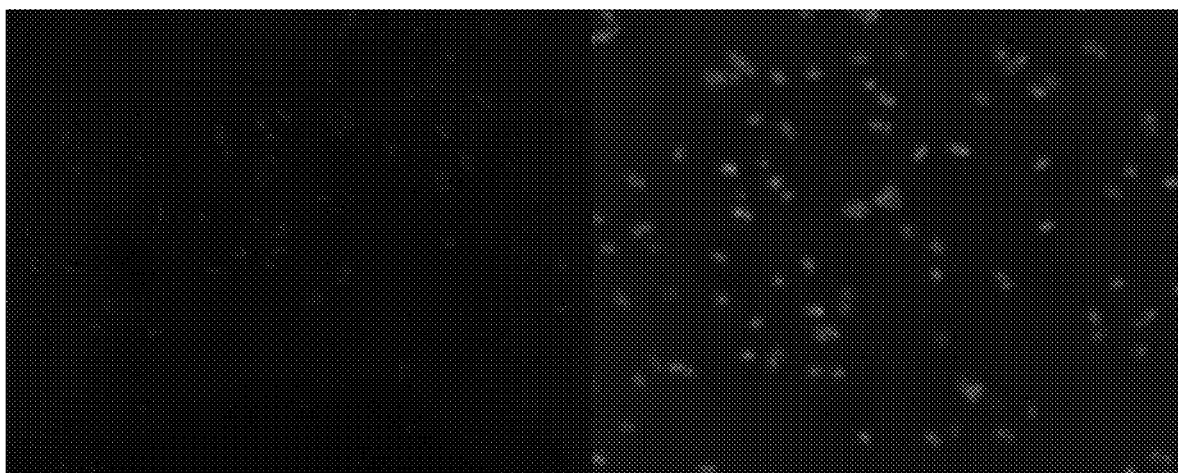
FIG. 22 is another micrograph of VRE grown in the presence or absence of the *B. producta* factor (which is a lantibiotic according to this disclosure)

FIG. 22 shows fluorescence microscopy results for VRE subjected to the *B. producta* factor (left panel), as compared to the control (right panel). Cells were stained with SYTO9, which stains all DNA green, and propidium iodide, which stains DNA in cells with compromised membranes red. Overall, VRE appeared to be less viable in the presence of the *B. producta* factor.

Figure 23:
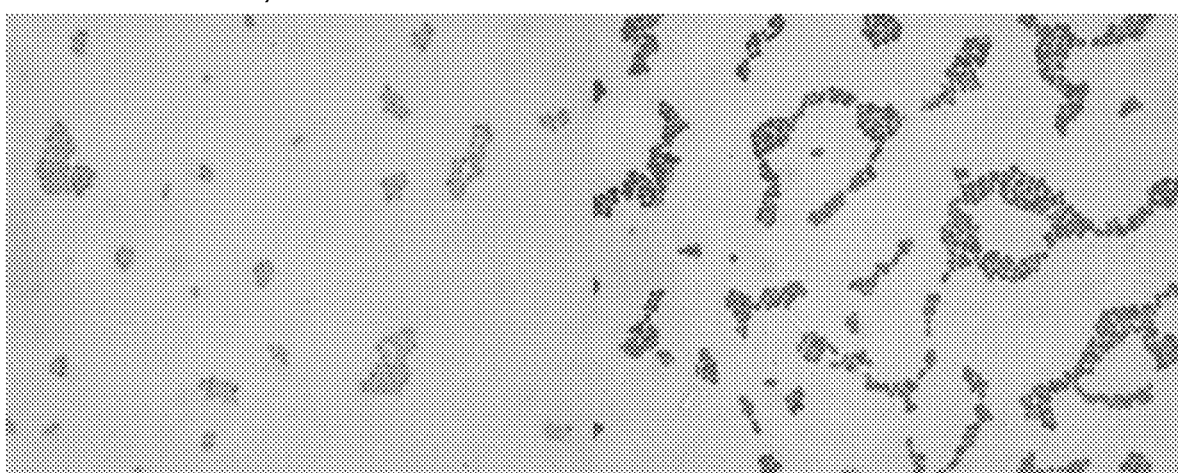
FIG. 23 is a micrograph of Gram stained VRE grown in the presence or absence of the *B. producta* factor (which is a lantibiotic according to this disclosure)

FIG. 23 shows light microscopy results for VRE subjected to the *B. producta* factor (left panel), as compared to the control (right panel). Cells were stained with Gram stain, which stains thick peptidoglycan in the cell wall purple. The VRE subjected to the *B. producta* factor generally lacked purple staining, indicating that their cell walls were compromised.

Figure 24:
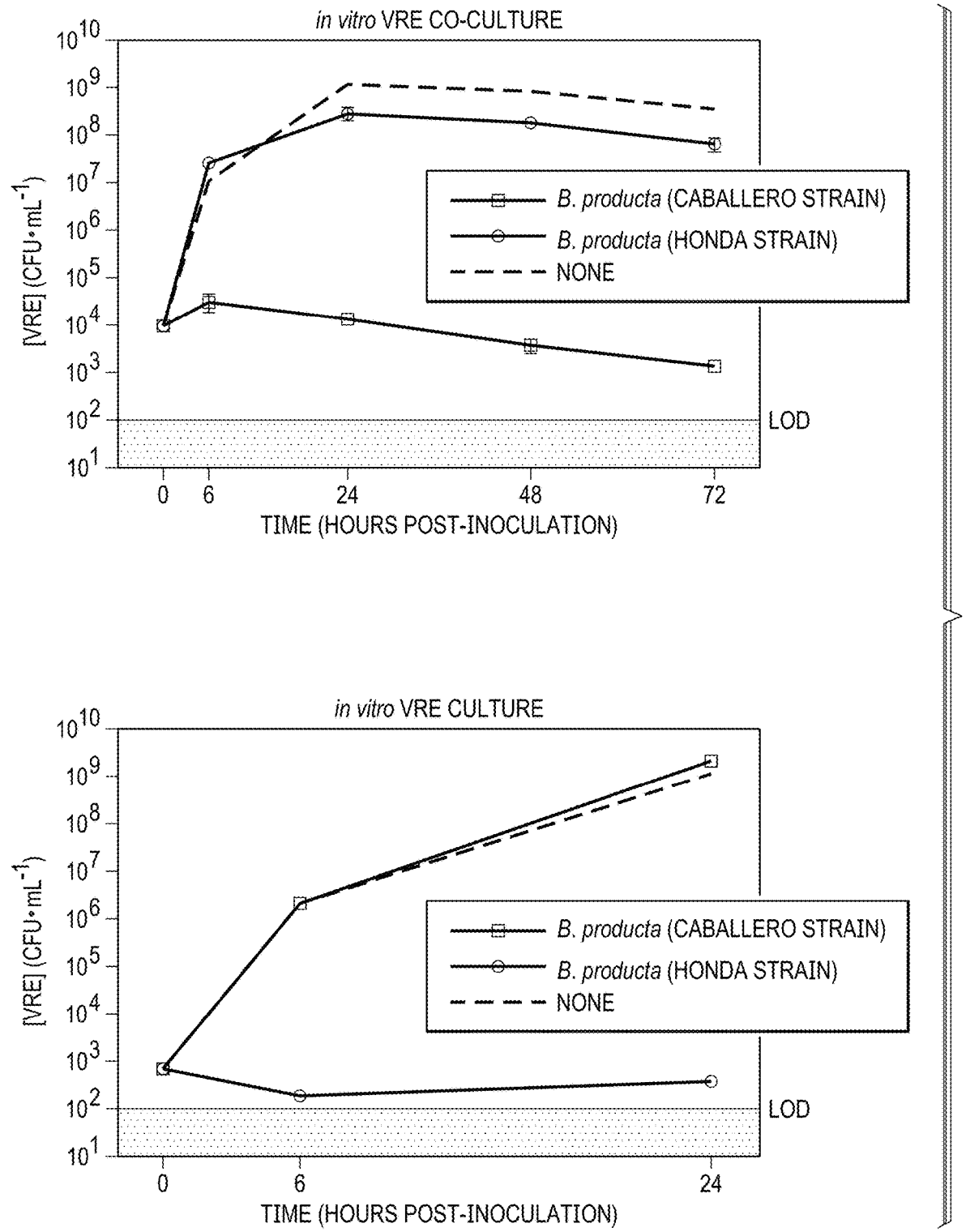
FIG. 24 is a set of graphs of the effects of two different *B. producta* strains on VRE when co-cultured (left panel), or when the supernatant is applied to VRE cultures (right panel)

Example 12: VRE Inhibition is not Mediated by all *B. producta* Strains $10^7$ CFU/mL *B. producta* Caballero strain or *B. producta* Honda strain (Honda strain Genbank assembly accession: GCA_000508925.1/BioSample ID: SAMD00012241/Organism name on NCBI: Clostridiales bacterium VE202-06) were cultured with $10^4$ CFU/mL VRE for 6, 24, 48, 72 hours anaerobically at 37° C. in BHIS. VRE CFU were quantitated and results are presented in FIG. 24, left panel. The Caballero strain, but not the Honda strain inhibited VRE. $10^7$ CFU/mL *B. producta* Caballero strain or *B. producta* Honda strain were cultured with $10^4$ CFU/mL VRE for 0, 6, or 24 hours anaerobically at 37° C. in BHIS. The culture supernatant at 0, 6, and 24 hours was filtered through a 0.22 μm filter, then concentrated by ultrafiltration with a molecular weight cut off greater than 100 kDa. The concentrated culture supernatant was then diluted to the original volume with fresh BHIS culture medium. The samples were inoculated with $10^3$ CFU/mL VRE the cultured for 6 or 24 hours anaerobically at 37° C. VRE CFU were quantitated and results are presented in FIG. 24, right panel.

The Caballero strain, but not the Honda strain inhibited VRE.

Figure 25:
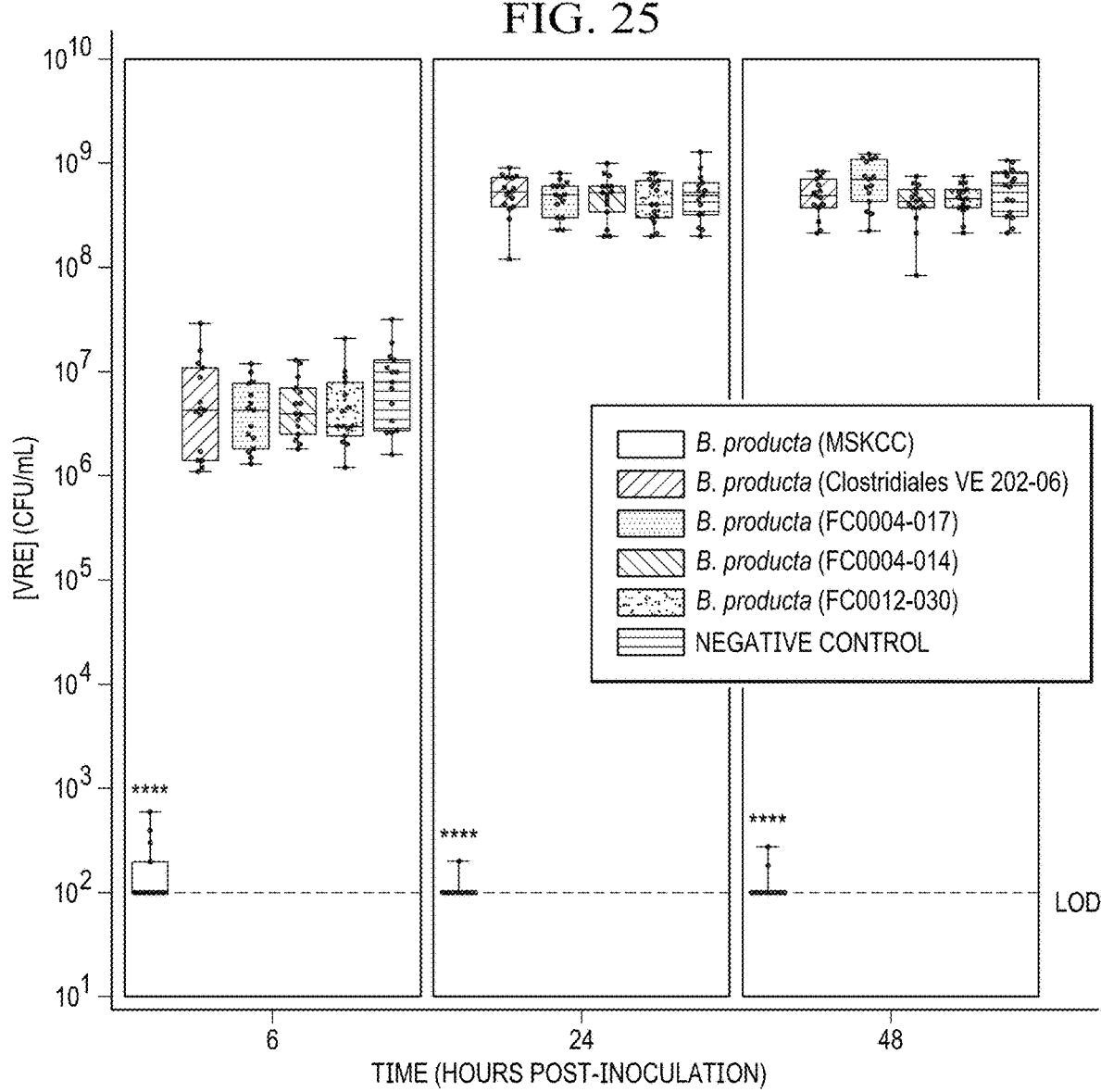
FIG. 25 is a set of graphs of the effects of different *B. producta* strains when the supernatant is applied to VRE cultures.

*B. Producta* strains, Caballero, FC0004-017, FC0004-014, or FC0012-030, or Honda, were cultured overnight (at least 8 hours) anaerobically at 37° C. in BHIS. The culture supernatant was filtered through a 0.22 μm filter and diluted 1:2 in fresh BHIS. $10^3$ CFU/mL VRE in inoculated in the diluted culture supernatant and cultured for 6 or 24 hours anaerobically at 37° C. VRE CFU were quantitated and results are presented in FIG. 25.

The Caballero strain, but not the Honda strain inhibited VRE.

Figure 26:
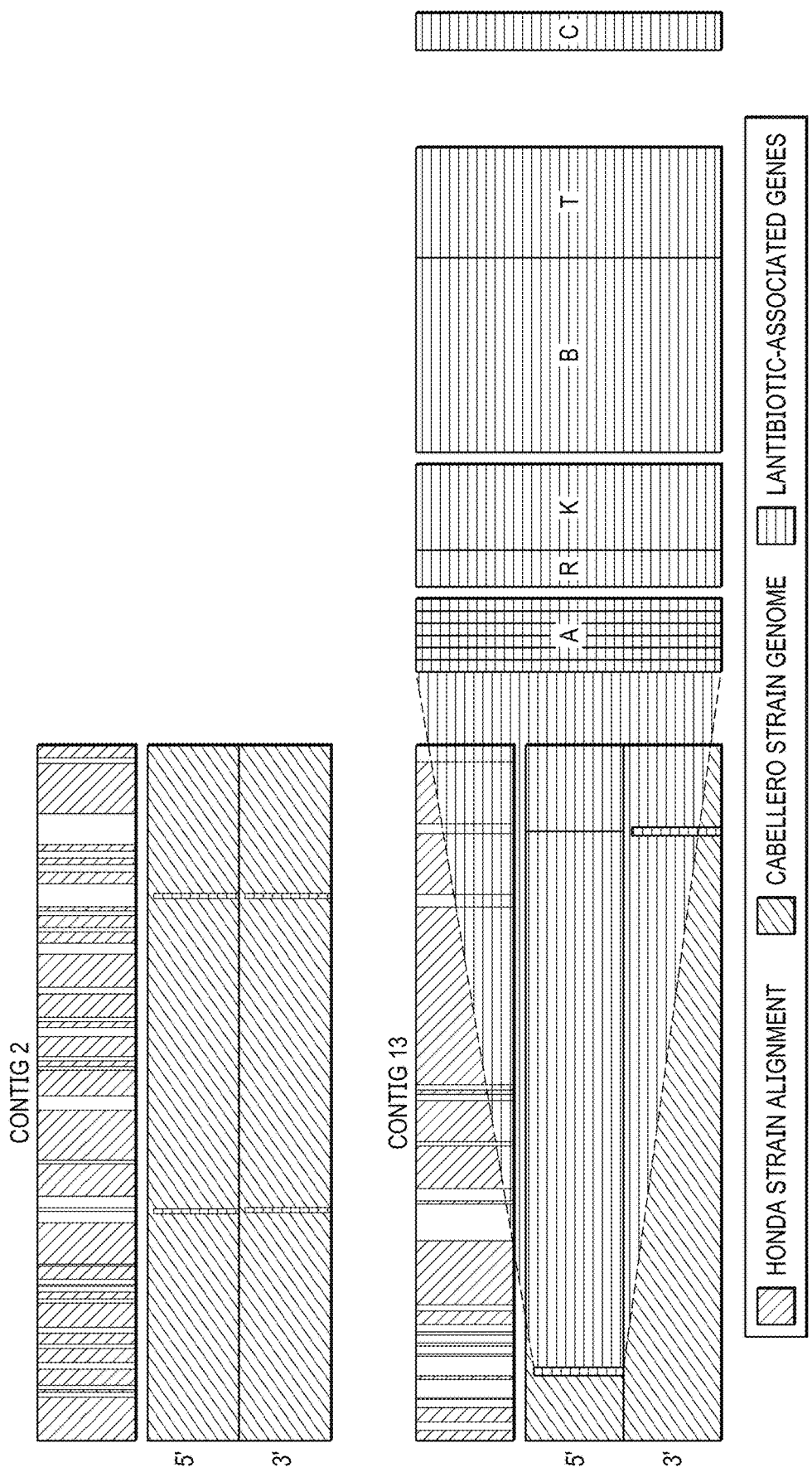
FIG. 26 is a comparative genetic map of the two *B. producta* strains of FIG. 24.

Example 13: Lantibiotic Genes are Only Present in the *B. producta* Caballero Strain anti-SMASH (Antibiotics & Secondary Metabolite Analysis SHell) and BAGEL3 (Automated bacteriocin mining) both detected "lantipeptide" gene clusters in *B. producta* (Caballero strain) genome but not in *B. producta* (Honda strain) genome. FIG. 26. Criteria for a lantibiotic gene cluster were a precursor peptide: (Lan A), regulatory proteins (Lan R, Lan K), post-translational modifying enzymes (Lan B:dehydration and Lan C:cyclization), and transport proteins (Lan T). One of the identified gene clusters contained all of the necessary genes for lantibiotic production, organized in an operon-like fashion: Lan A (precursor peptide), Lan R (regulatory protein), Lan K (regulatory protein), Lan B (post-translational modifying enzyme—dehydration), Lan T (transport protein), Lan C (post-translational modifying enzyme—cyclization). The candidate inhibitor produced by this gene cluster had a sequence similar to that of nisin.

Figure 27:
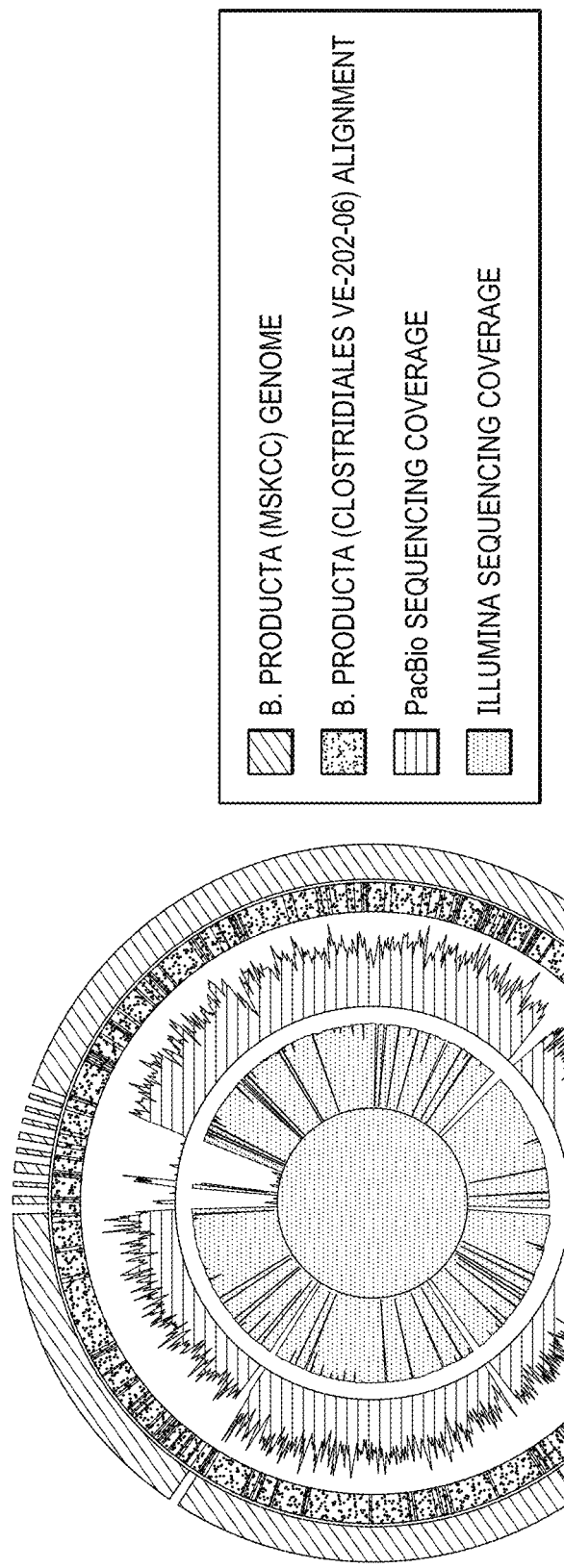
FIG. 27 is a graph showing the location or absence of a lantibiotic operon in two *B. producta* strain genomes as confirmed by sequencing.
Figure 27:
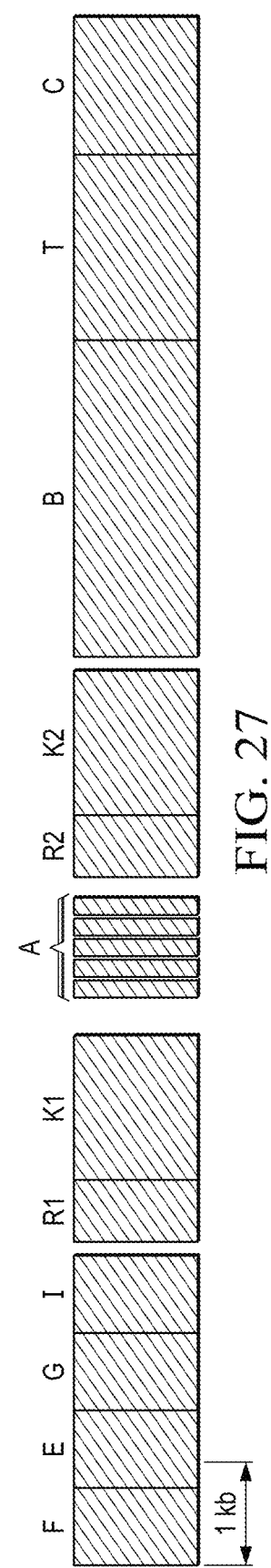

FIG. 27 presents genetic analysis of the genome of the *B. producta* Caballero strain, which shows it contains the lantibiotic operon. The Honda strain, in contrast, lacks the lantibiotic operon.

Figure 28:
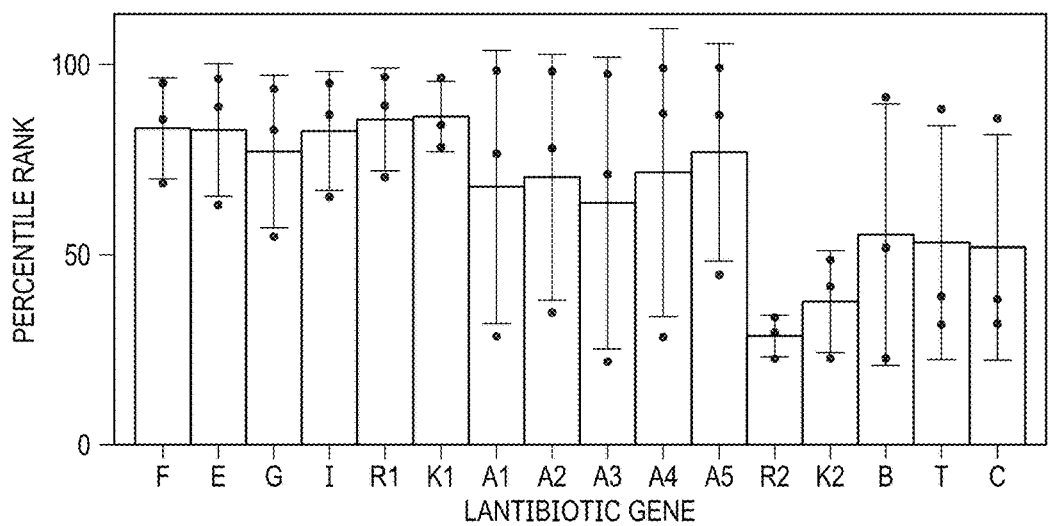
FIG. 28 is a graph of in vivo expression levels by a *B. producta* strain of genes in the lantibiotic operon.

6-8 week old, C57BL/6 mice were administered ampicillin (0.5 g/L) in the drinking water for 5 days, and subsequently orally gavaged with a bacterial consortia ($10^7$ CFU per bacterial isolate). Bacterial consortia for oral gavage were prepared by individually culturing the *B. producta* strain on Columbia base medium (agar, peptones, cornstarch) plus 5% sheep blood agar plates, anaerobically at 37° C. overnight. Each isolate was subsequently harvested and resuspended in reduced phosphate buffered saline (PBS) to a final concentration of $10^8$ CFU/mL. 14 days post-transplant, cecal content was harvested and RNASeq analysis was performed. Results, shown in FIG. 28, show that *B. producta* (Caballero strain) expressed antibiotic genes in vivo.

Example 14: *B. producta* Caballero Strain Lan Genes

LanA (SEQ. ID. No.: 5)

ATGGCAAAATTTGATGATTTCGATCTGGATGTAAC

AAAGACAGCAGCAGGGGAAGGCGGAGTAGAACCGC

GAATCACAAGTAAGTCCCTGTGTACACCGGGTTGT

GTGACGGGAATCCTGATGACCTGCCCGGTTCAGAC

AGCAACCTGCGGATGCCAGATTACTGGTAAATAA

LanR (SEQ. ID. No.: 6)

ATGTCAAAATACTTGTTATTGATGATGATAAAAA

AATACTGGAATTAGTATATGAGGTATTGATGCGAG

AAGGGTACGATGTAGAAACAAAGAGTATATTGAA

AATATAAATATAGCGGAATTTGAAAAATTCGATCT

CATTTTACTTGATATTATGATGCCAGTATTTGATG

GATTTGAAATCCTAAAAAAAATAAAGTGTATTATT

TCGTGCCCAGTAATTTTTCTTTCCGCAAAATCTAG

CGAAGATGCAAAGGTAAAAGGATTGATGGAAGGCG

CGGATGATTATATAACAAAGCCATTTAGCATAAAA

GAATTGGTGGCTAGAATAAAAGTTGCGCTAAGAAG

AAATACGAATATTAAGAAGATAAAGTAGAAGTTG

ATGGATTAGTATTTGATTTAAATACAAATTCTATT

GCACTAGATAATAAAACTATTATCTTGACTAAGAA

TGAATTTAGAATATGTAAAATTCTTGTACAAAATC

AAGGGCAAACTTTTTCAAAGGATATGTTATATGAT

TTTTTATATGATTTGGATACGGATACTCAATTAAG

AACAATCACGAATACATTTATTCAATACGGAAGA

AATTCAAACGTTTTGAAAAAGATCCAATAAAAACT

GTATGGGGATTGGTTATAGATGGTGCATAGATTA

A

LanK (SEQ. ID. No.: 7)

ATGGTGCATAGATTAATACCTATGAAGAAACAGTT

AATGTTCTATATATTACAGTTAGTATTAGGATTGG

TAATAGTAGGTATGGGATGGCTATTTATCACAAAT

ATATTGATATGTGCCAAGATAGTTATTCCTGCAAA

TTATAGTGAAAATATATTAAAAGAAAATAGTGCTA

AATTATCAACTTTGGATAAAGTTACATCAGATTTT

TTGCCAATCGGATGCGAATTTGCTGTATTTGATTT

TAATAATAATAAAAAATATGGAAATATGAGTTCGA

TTAATGAACAACATGCTTTGAACGTTATTCTTGGA

AACGAGAATAATATCCAAGGAAATAAGATTTATTC

AGTGATATTTAGGGAAAAAGAAATTTGTGTAGTTA

AATATAATATGCGACCTTATTTCAATTTGACGAAA

AGAAATTTGCAACTTCCCAATTACGATATTATTTC

CTATGCAGTTATGCTAATAGTGTATGTTATATATG

TTTATATTTCTACATTCAGGCTAGTAAAAAATTGG

GGAAAGGAGTTTGAAAAAATCAAAAAAAATAACTTT

AGAGATTGAAAATGGGAATTTAGATTTTGAATATT

GTTCTAGTAAAGTAAAAGAGTTTTCTAACGCTATA

GATTCCTTAATAAGAATGAGAGATGCTTTAAAAGA

TACATTATATTCGAATTGGAAAATGGAATATGAAA

AAAATGAAGAGATAGGTGCCTTGGCACATGATATT

AAAATTCCATTAACTATTATTAAGGGAAATACGGA

ATTAGTATTAGATTACAATTCTGATTCATACAATT

TTTTACATTTGAGAAATGTGCTAGAGGCGGCTGAA

AAAAATAGAAAATATCTTGTAGTGCTTCTTCAATA

TGTCAAAGCTAAAAAAATAGAAAATAATAAAAGGG

AACGAATTGATTGCGATACGTTTTCCGAAAGGATT

TGTCTTGAAGTGAAAAAGTACACAGCTAATTTACA

TACAAAATTTGAATTTTCAGTTGACCATGTTAGCG

GCATGATTTATATAGATTACTTTTCTATAGAAAGG

GCCATATTTAATATCATAGATAATGCGATTGAGTA

TAAAGTCGAAGATGATAAGATTTTATGTCATACGA

TGCTAGAGGATGGAATGTATACTATTTCTGTATCA

AATAGTTGTGGACAATTTGACAAGGAAGTTTTAGC

GAATGCTACTAAATTATTTTATACATCAGATAAAA

ATAGAAATACATTACACTACGGAATTGGATTGGCA

TATGTACAAAGAGTCGTTGAAACGAACAATGGATA

TATGAGTATATTTAATTCAGATAAATTGGGTGCGA

CAGTAAAAATTCAGTTACCGATAATATCAAAAGAA

AATAGTTGA

LanB (SEQ. ID. No.: 8)

ATGAAAAAATTATTTTATGACATTGGAGAATTTAT

GTATCGCAGACCGACTGAGTATAAGTCTCAAATTG

ACTTTTCCGAACATGAGGTTAAGTTAATATGTAGC

AATCCTGCATTTAGGGAAAAGTAAATATTGCAAG

TCCTTCATTGGTGGAAATGATGGATATATATATGA

AAAATCCTAAACAATTATCAGAAAAGAAATCAAAT

GGATTAAATATTTCTTTATTGAAATATTTAATCCG

GAGTAAAGAAAGGACTACTCCGTTTGGCTTGTTTA

CAGGTGTTGGAACTGGCTGCTTTAGCAAAAGTGAA

AAATTCCCCATATTGATGACGAAGACAGAAAAAAA

```
AGTTAATGTTGATTCTGAATGGTTATTTGGACTAG
TAAATATTGTAGAAAAAAATTATGCTGAGAAATTG
GAATTTAAGTTTAATGACGCATGTTATATAAAAGG
CAATAGAGTTATATTAGTATACTCAACTGAAAAG
ATGCAGAAGAAATCAGTATTCGATTTACAAAGTT
TTTAAGGTACTTTTTGATAAAATTAAGGATTACGA
AAGATATGAAAAATTCATTGAAATACTTAGTTCTG
AATATCCGAGTACTTCAATGAAGAAAATCAAATTG
TATATAAATGAACTGATTTCTAAAGGTTTTTTGAT
TTCTAATTTGAGACCATCGTTTAGCAATGCAGATC
CGCTAATGTACTTTATCAAGCAGTGTGAGCGAATG
GAAATTACAGATATATGTGAAAAGGCTAATGAAAT
ATATAAAATGTGTGAGGATTATAGCAAAACAGATA
TTGGTAATGGGATAATTAAGTATAATGCGATAAAA
ACAAAAATGCAGACATTATATAAATGCTCATCATA
TTTACAAGTGGATACTGTTATAGGTGGAGGCGACT
TTCAACTTAATCAAGACATTTCCAAGGCAATATGT
GAAGTGGCAAGTCTATTTGTGTATCTTAGTAATAG
TCCTAAGAAACAACATGGTTATTTAGAACATTATA
GAAATAAATTTATTGAAAAATATGGAATAGATCGG
GAAGTACCTTTATTGGAAATGATTGATTCTAGTAA
TGGTATTGGAGCTCCAACACCATACTTAAAGCCAC
AAAATGATTTTTACGATGAGTACAATACAAAAGAC
AATTATAAATATGAACTAAAAAATTATTTTTTGGT
GGAGTATGAAAAAGCTTTGGCTAATAATTCATACA
TTGATATTAATATGGAGACTCTTCAAAAAATAACA
GATTGTACCGTGCAAGAAGAAGAAATCCCTATTTC
TTTAGAATTATATTTTATTTTGAAAGTAGAAGATG
GAAAAGTGAGTCTTAATCTAAGTCCTAATTGTGGC
TCATTTGTGGCAGGTAAAACTTTTGGTAGGTTCTC
CGTACAGTCTGACAATTTTGCAAATGTTTTAAAGA
AATGTAACAAGAAGAAAGAAAAATTCGTAGTCCG
CATAGTGAAATTTGTGAAATAAGTTTTTTGCCTTC
TCCAACGAGAAATGGAAATATTGTAAGAACATTAT
CGTTTAGAGAGAAAGAAACTGCCGTTTTTACCTGT
GGCAGCAAGGATAAAAAGACATTGTTAGTCTTAA
TGATATTTATATAGGAATATTTAACGAAAAGTTTT
ATGCAAGGGATAAAAAGACTGGGAAACTGATTATT
TTCGAATCAAACAATATGTATAATCCGATGCTTAA
TCCCAATGTTTTTAGGTTTTTGCAGGATATTTCTT

ATGAAGGAAAAAGGGAGTGGTCTGAGTTCCCATGG
AGTTATATCTATGCAGATTTGAGACATATTCCAAC
AATAAAGTATAAAGGAATTGTACTCCAAAATGAAA
AATGGAAAGTTAATATACAAGAACTTGAATTACTC
AAAAAGGATTTTGAAAGTTTTAAAGAAAAATTTTT
AGCATTGATTATTGGCCGCAACATGCCTTTGAATA
TTTATATTGTTGATGCAGATAACCGTATTAGACTT
AATCTGGCAACAGATTTATCGATGCGGATTGTTTA
TGACGAATTTAAGAAGCATAAGGATAGTGATTTGG
TTTTTGAAAAAGTAGAAAATGGTTCAGATATTATT
TATGATGATGGGAAAACGTATGCAACGGAAATAGT
TGTTCCGCTTTTCAGGAAAAATAAAGAAGAACTAT
CATTAATTCCATTATCCCAAAAGACGTATACCAGA
GAGCAGCATATGATTTTGCCATTTAATAACTGGCT
TTATTTAAAATTGTATTGTAATGAGAATCGAGAGG
AGGAATTAATTGCATTTTATATTATGGATTTTTAT
GAATCATTAAAGGAAAAATATGGTATTTCATATTT
TTATATGCGTTATGCTGATCCGAAGCCACATATAA
GATTGCGATTACATGCAACAAGAGAATTGCTATTG
CAAGTCTATCCACAAATCTTGAAATGGTACTCAGA
ATTGTTCTCAGATCAGATAGTAGGGGATATGACTA
TTTCTGTATATGATCGAGAAATTGAAAGATATGGA
GGGGCATTGTTGATGGATACTGCGGAAAAGGTATT
TTTTGAAGATAGTTATATTGTTGAAAACATACTGC
GTTTAAAACGTTTGGGGAAAATATCTTTAAATTTG
GATGATGTTGCTGTTGTTTCCATCATAATGTATGT
TTCGCAGTTCTATAATAAATATGAAGAGCAATTGC
AGTTTTTGTCAATCAATTATCATTCTTCCGATTTT
ATAAGCGAATTCAAGAAGAAAAAGATAATCTATT
AAGAATTTGCGATATTGAAAATGAATGGAATAATC
TAAATAGCATGAAAGACGGTAAAGTTGTTTATGAA
CTTATGTGGCGAAGATGTAAAGTAATTAGCGAGTA
TAGTGAAAAAATTAGGAAGATTAATCCAGATCCGA
TGTTTAAAAATAGTATTGTTGCAAGTGTTATTCAT
TTACATTGCAATAGATTGATTGGTACAAATCGTGA
ATTAGAAAGGAAGCTGATGGCATTTGCAGAAAGTG
TGTTATATGCAAAAAAATATGTAATGAGAAGGATT
GAAGTCAATGGAAAGAAATAG
LanT                            (SEQ. ID. No.: 9)
ATGGAAAGAAATAGAATTGGAATCAAAGATATACT
AATAGCTTTAAAACAATTACCTAAAACGGTTTCTA
```

-continued

```
TTATTATGCATGTAAGTAAGGGATTGTTTTTTCTT
ATTATATTATTTAGTGTGGTTGCTGGAGTTTTTCC
GGTAATTACACTGATTCTTTCCCAAGAATTGATTA
ATTGTCTTGTGCAAGGGAAAAACTTTTTTGATGGT
ACATTTATAATGTTTGTATTATATTTGCTTGCATC
ATTTGCCGGAGAACTAATTATTGAAGCAAAAGGAT
TTATAGAGGGAAAATTTCAATATTTGTTACAGTAT
CGCTTGAATTATCTGGTTATGGAAAAATGTACGGA
TCTATCTTTGGAAGATTTTGAAAACTCTGAAATGT
ATGACAGAATCGAAAAAATAACAGGGGAAATTGCA
TATAGACCATTTCAGATTTTTCTGGCGATTATTAA
TCTTTTGACATCTGCGATTACTATGATATCGTCCG
CTATTTTGCTTTTTAGCTGGAATCCTTATATATCA
ATTGTTTATTGGTTGTTCCTATTGTTTCAGTACT
ATATTTTTGAAAATAGGTCAGCAGGAGTTTGATA
TTATATGGAATCGTGCAAAAGACGAAAGAAAGACT
TGGTATTTAAGCTATTTATTGACACATGATTTTTC
TTACAAGGAAATATCTTTATTAAATATAAAAGACT
ATCTTTTAGGAAATTTCATAAAAATAAGTAATCGT
TTTATTGAACAAAATATCAAAATCTTAAAAAAGAA
AACAGTATTTAACATTATCTATGAGATGATCATGC
AAGTAGTAAGTGGCTTGATTATTGGTGAGGCAATT
ATATCGGCATACGCAGGGGATATTCTTGTTGGAAA
CGTTATGAGCTATATACGGAGCGTGGGATTAGTTC
AGAGCAATTCACAGGCTATTATGGCAAATATCTAT
ACCATATATAATAGCTCATTATATATGGATATGTT
ATTTGAGTTTTTGAAATATTGTGGAAAAGGTAAGA
TTACTGGGAATATGAAAAAAATTGAAGGTGAGATT
ACAACGATAGATATAAAAAATCTCTCTTTCTCTTA
TAAAAATAAAAAAGAGACGTTGAAAGATATTAGCA
TCAGTTTTCAAAAAGGGGAGAAAATTGCATTAGTA
GGTCCTAATGGCTCTGGGAAAGTACATTAATTAA
AATTTTAAGTGGATTATATGAGATTAAGTATGGCG
AAATTTTGATTAATGGCATACCTCTAAAGAAAATT
GATATTGAAGATTATCATACGAAAATGTCAGTACT
ATTTCAGGACTTTGTAAAATATGAACTCACATTGA
AGGAAAATATAGGATTGGAGATATAAAGGAATTT
AATTCAACTGATAGAATGAAAGAAATTCTTGATAA
ACTTCAAACAAAGTTTCTAAAAAAGATGGTGAAT
ATGATTTCGATATGCAGCTTGGAAATTGGTTTGAT
```

-continued

```
GATGGACAGCAGTTATCACAAGGACAATGGCAAAA
AGTGGCACTTGCGCGAGCATATTTTAAGAACGCAT
CAATTTATATCTTGGATGAGCCGAATGCTGCGCTT
GATACAGTTTCTGAACGGGAAATTTTTGATGATTT
TTTTGAAATATCAAAAGGAAAAATAGGAATTTTTA
TATCACATCGACTTAATGCGGCAAAAAAGGCAGAC
AAAATAATTGTTATGGATGATGGAAGAGTTGTTGG
AATGGGTAAACATGAAGACTTACTAAAAAATTGTC
TTGTATATCAAACTTTATATCAGGCTGAGACATAC
GAGAATGAGGAGGATATGTAA
```

LanC (SEQ. ID. No.: 10)

```
ATGGATAACAGCATAATTTCTATTGTAAAAGAGAT
TGCTAGAAACTTAGGCGACTATGATAATGTAAAGA
GGATTGTAGCGGATAAAGACAATATACGAGTGATG
GGAGAATTTAATTTTCAGGGATGGGAACCACTTAC
ATTAAGTCATGGAATACCAGGAATCTGTTTGCTAT
ATGGGAAATTAATGGAATGCTTTCCTGATGAGGAG
ATTTGGGCTGAATTAGCACATCAGTATCTTGGTTA
TTTGGTGCAGGAAATAAATAAAGAGGGGTTTCAAA
CCTTGTCAATGTTTTCAGGAACTTCTGGTATTGGG
TTGGCTGTTGCAAGTGTTTCAAATAATTTTTGTAA
CTATAATAAACTGTTAAATACGATAAATTCGTATA
TAATTAATTGGTTTGATGAGTTTATTGATAGTATT
GATTTAAAAAAAGGGACTAGAAGTATCTGTTATGA
TGTAATAGAAGGCTTGAGTGGTATTTTGAGTTATT
GTTCAATATACTATGAACAGGAATCCTTTTCTCCG
ATATTACTTAAAGGCTTGAAAAAATTAGTTGAACT
TACATATGATATTGAAGTAAAAGGATACCATGTGC
CTGGATGGTATATTCCATCGGATAATCAGTTTAGT
ACTGTAGAAAAGAGTTATATCCATATGGTAATTT
TAATACAAGTTTTTCTCATGGAATTGCAGGTCCAT
TAACACTACTTTCAGAAATGAAAAGTAAAGGATTT
ATGATTGAAGGACAAGAAGAGGCAATTGAAAAGAT
TGTAAAATTTCTATTTGATTTTAGATCTAACGATC
AAAAACGAGATTTTTGGAAAGGCCAAATTGACTTC
CATGAATATATAACCGGAAAAGTGTCAGAAAAAAA
TATAATTCGTCGAGATGCTTGGTGTTATGGAAATC
CGGGAGTGTGTTATTCACTTATTATGGCTGGCAAT
GCAATGAAAAACCAAAGTTGGATAGATTATGGAAT
ACATAATATGAAAAAGACATTGAGCGATGTAAAAG
GTATATTTTCACCTACATTTTGTCATGGTTTTTCT
```

```
GGATTGTATCAAGTTGTTAATTCTATAGAATTTAC

TATTGGAAAGGACATTTTTATAGTGAGAAAAAG

AATTGCTTAATAAAATTATGAGTTTTTATGACTCT

AACTATATTTTTGGATTTAGAAATATGGAGGTAGG

TGATGAGAATGGAAATATAAGAGCTTTTGAACATT

TAGGTTTATTAGATGGTACAATTGGAGTATGTCTG

GCTCTTTTAGAAGGAGAGCATAAGACAAAGAACAT

TTGGAAAAGAGCTTTTTTGTTAGCATAG
```

Lan F
(SEQ. ID. No.: 11)
```
ATGAATATGATTTTAAAAACAACAAATCTCTGCAA

ATCATTCAGCGGGCAGACAGCCGTAAATAACATAT

CGCTGAACATTGAAAAAAATTCCGTCTATGGATTG

TTAGGACCAAACGGAGCCGGAAAATCCACAACACT

CAAAATGATAACAGGCATTTTGAAGCCCACATCTG

GGAGCATTGAGTTTGACGGCCACGCATGGAAGCGG

AGCGACTTAAACCATATTGGAGCATTGATTGAAAT

GCCGCCGCTTTATGAGAATTTAACCGCCTATGAAA

ATCTGAAAGTTAGGTCAACCCTTTTAGGGCTGACA

GACAATAGGATTGAGGAAGTGCTTCAAATCGTCCG

GCTGACAGAAACAGGCAGAAAAAGAGCCGGACAGT

TTTCTCTTGGAATGAAGCAGCGGCTTGGAATTGCA

ATTGCATTATTAAATAGTCCGAAGCTGCTTATTCT

TGACGAGCCTACAAACGGTCTTGACCCGGTGGGA

TTGAAGAACTTAGGGAGCTTATCCGTTCATTTCCG

GAAAAGGGAATTACCGTTATTTTATCCAGTCATAT

TCTTTCCGAGGTACAACAGACCGCCGATCATATCG

GCATTATTGCGGGCGGTGTCTTAGGCTATGAGGGG

AGACTTAATGCGAATGAAAATTTGGAACGGCTTTT

TATGGACGTTGTGAAAAGCAATCACAGGGAGGGCT

AA
```

Lan E
(SEQ. ID. No.: 12)
```
ATGAATTACTTAAAATCAGAGCATTTGAAATTCAA

AAGGACAATATCAAACAAGCTGCTTTTCATCATTC

CGCTAATCACAGCTATTTTTGCATGGATAGTGGGA

GGTTTTATCGGGTTTCAATATACAACGCTTTACTG

GTGGTATGCGTTCCTGCTTCCGGGAGCAATCGCAA

TCTTATGTTCCTTATCACACCGGAAAGAAGAAAGT

GCGGGGAAATATTATTCTGTATTTTCTATGCCCTT

GAACCTTTCAAAATTTGAAATGGCAAAGGAATGA

TTTTGATTGAAAAGCTGCTTGTGGCAGGAGTATTT
```

```
TTAGCATTGCTTATCTCAATCAGCAATATCATTTC

CCCGGCAACAGCGGTATATTCTGTTCCGCAGAGTA

TGGCAGGCAGTATAGCGATTGTGATAGCGTCCGTC

TGGCAAATCCCATTGTGCCTGTACCTTGCGCGTAA

AATAGGACTTTTTGTACCGATAATGCTAAATACTG

TACTTGGGATATTCTTCCTATCCTGTTAGGAAAC

ACAGCCGTTTGGTGGCTCATGCCGTATTGTTGGGC

GGCGAAGCTGGCGGAGCCGCTTATGGGGATTGAAT

TAAACGGAACTTTTGCGGGAAATTCCGGTTTTTCT

TGTACCATTTTTATCTCTGTCGCACTATCAATATT

CTTATTCATTGTCTTATCTTTTGTAGACGCGAAGG

ACTTTGCAAAAGGAGGTAGATAA
```

Lan G
(SEQ. ID. No.: 13)
```
ATGGGCTTTCTTGGGGCGGTTCGTTCCGAACTAAT

AAAAGTAAAGCATACGTCCTTTGGGGTAATTCATT

TATGCGTACCTGTTCTTGGGGCGTTACTGTTTATT

GTTTACTATGTCCTATATGGAAACACAGCGGATTA

CAAAAAACTAAAAATGATATTAGAGCTTACGGCGA

CTATTTTCCCTTTGCTGATAAGTGTTGTTGTGAGC

TTGAATGTCTTATTGGAAGAAAAGGCTTCACACTT

TCAAATATTGCTCGGAGTGCCTAACCGGTATAAAG

TTGTACTGACAAAATTAGCCGTTTTATATGGAGCA

GGAATAACCGCGCTGTTTTGTCTATTCCTTGTCTT

TCTGCTCGGCGTTCATTTTTTGAGAATAGATGATA

CCGTACAACTTAGTATGTTAGTCAAAGCAGCCGCA

GGAATGGCATTTTGTAATTTAATTATTTATGCGCT

GCACTTATTCCTTAGCTTTCGATTTGGACTGGGTA

TCTCATTGTTTTGGGGAGTATTTGAAAGTCTGCAA

TGTATTCTATACAGTAATATCGAATTAAAAGGTGT

AGGGCGATATATCCCCTTTGCATGGTCTATGAACT

GGGTGCATGATGTTATGAACAACGTGCTGTCCACT

CATGGGACAGAATGGATAGGAATTGCTGTATTGAC

AATGGGCGGTGTATTATTAACTTTACTATGGTTTT

CTCATTGGGAGGGACGAAAAAAATTATGAATAA
```

Lan I
(SEQ. ID. No.: 14)
```
ATGAATAAAAACAAAAAAATAGTTATATTTCTGCT

GTTTACCTTTATCGTTTGTGTGGCTCTTGCAGGCT

GTTCTTTACAGGACAGAATCGAAGAATATTCCAGT

GACAAAGAACAATGCTATTTGAATACGGAAAGCGT

AACACGTTTTTCCTATAAGGGTAACGATTACACCA

TTTTGGCAGATACCGTATCAAATGGTGGGCTTGGA
```

-continued

```
GAATGGATTGGATATATCCGGCAGCTTGCCGCCAT

AGATGAGAACGGAAAAATATTGCTGCAAGAAAATG

TTGAAACGGCGACTTTTCAATCCTTAGCGGATTTG

GCAGAGAAAGCACCAGAAGCCTCTTACATTATTCC

GTTTCTCAATGTATATGCAGCACCTAACGCAGACG

ATTATCTGATTGTAGATGTAAACGGAGGGTATCAT

AAAGCTGTTATCAGCGAGAATATCAAGGATAGCGA

TACTGTTTTTGATTTTAAGGAAACAGAAAAATCTA

TAAACGGCAGCTTTGAAATCAATCCAGAAAATGCG

ACACAGCTTCTTTGTGGCGGGACGGTTTATCAAGT

AACGTCTGAAATGGTATCTGATGATAAATTAGGCA

GCTACATTGATATTCTTGCAGAAAGTGTTACATTT

GACACAGAAACGAAAATCCCTTTGTCAAAGGAAGA

TTTAAGCAATGTTGACTGGTACGGGGAGAATACCG

GACAGGGGCGGGAGTATTGGTTTTACACAGATGTC

TATGAGATTTACGGAACCGATAAAGCGGAAGCGGT

TGCGGTCAAGATAAATAATAACTACTATATTGCAA

AGCGGCAATGA
```

Figure 29:
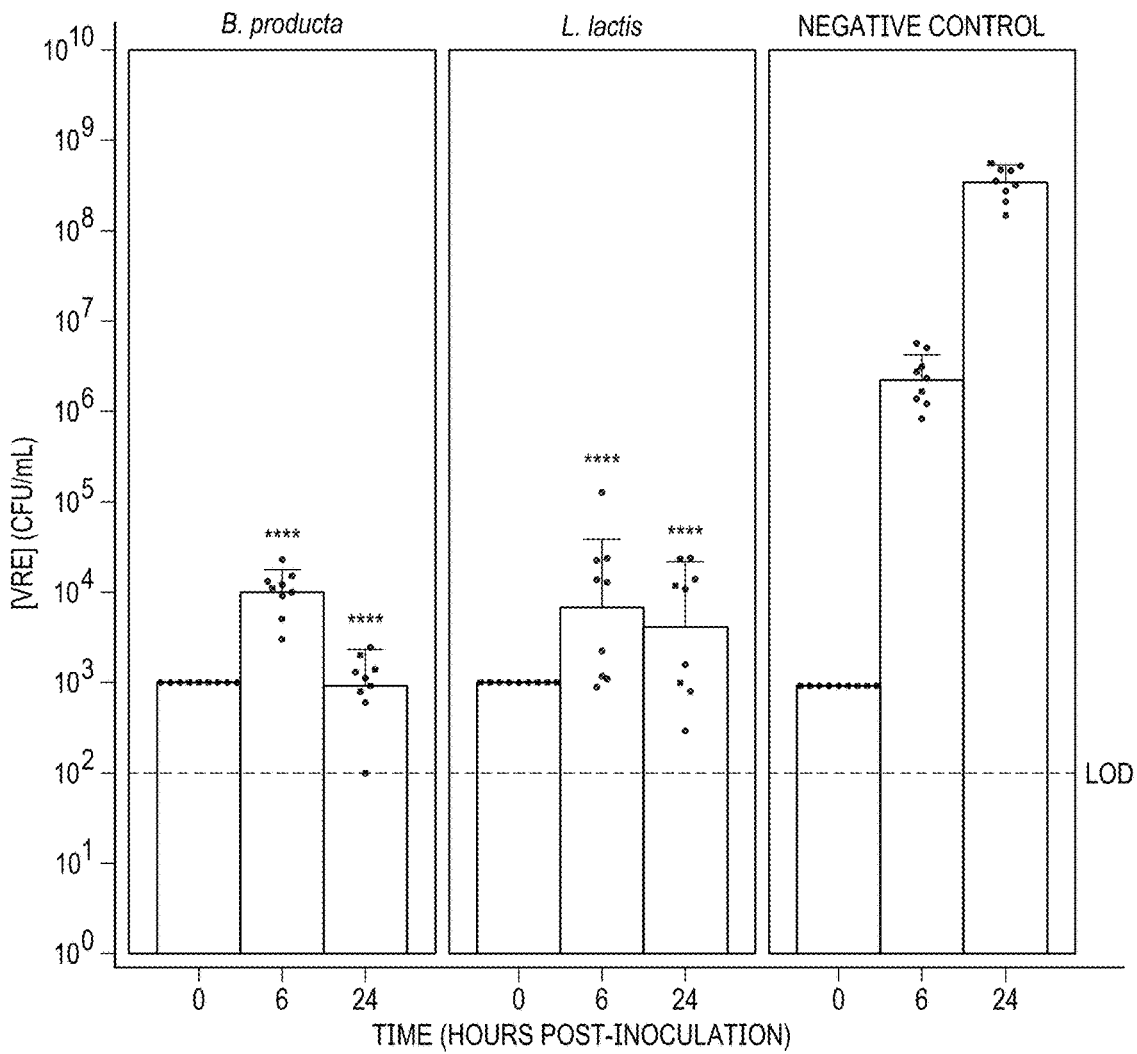
FIG. 29 is a graph of the effects of lantibiotic-producing *B. producta* and *L. lactis* strains on VRE.

Example 15: *B. producta* and *L. lactis* have Similar Effects on VRE Growth In Vitro and in Vivo $10^7$ CFU/mL *B. producta* Caballero strain or *L. lactis* ATCC 11454 strain were cultured with $10^3$ CFU/mL VRE for 0, 6, or 24 hours anaerobically at 37° C. in BHIS. VRE CFU were quantitated and results are presented in FIG. 29. Similar VRE inhibition was seen with *B. producta*, which produces a lantibiotic as described herein, and *L. lactis*, which produces nisin. 6-8 week old, C57BL/6 mice were administered ampicillin (0.5 g/L) in the drinking water for 5 days, and subsequently orally gavaged with VRE ($10^4$ CFU). Bacterial consortia for oral gavage were prepared by individually culturing the *B. producta* Caballero strain, *B. producta*, Honda strain, or the *L. lactis* ATCC 11454 strain on Columbia base medium (agar, peptones, cornstarch) plus 5% sheep blood agar plates, anaerobically at 37° C. overnight. Each isolate was subsequently harvested and resuspended in reduced phosphate buffered saline (PBS) to a final concentration of $10^8$ CFU/mL. Three days after VRE administration, a bacterial consortia transplant was orally gavaged (107 CFU per bacterial isolate). Fecal pellets were collected 0, 5, 10 days after bacterial consortia transplant, and VRE was quantitated.

Figure 30:
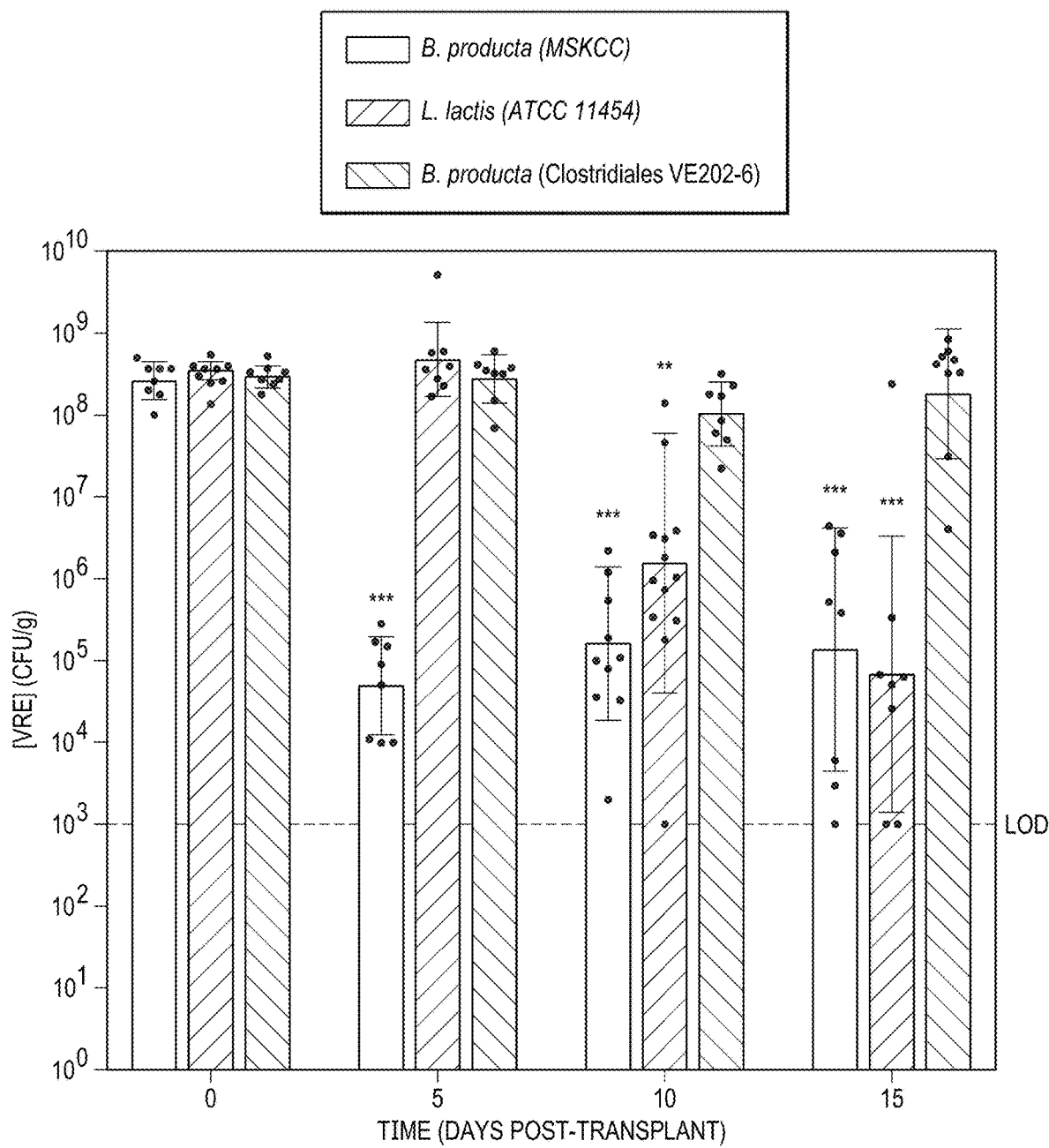
FIG. 30 (34) is a graph showing the effects of lantibiotic-producing *B. producta* and *L. lactis* strain on VRE in vivo.

Results, presented in FIG. 30, show that *B. producta* Caballero strain inhibited VRE in vivo in a manner similar to *L. lactis*.

Figure 31:
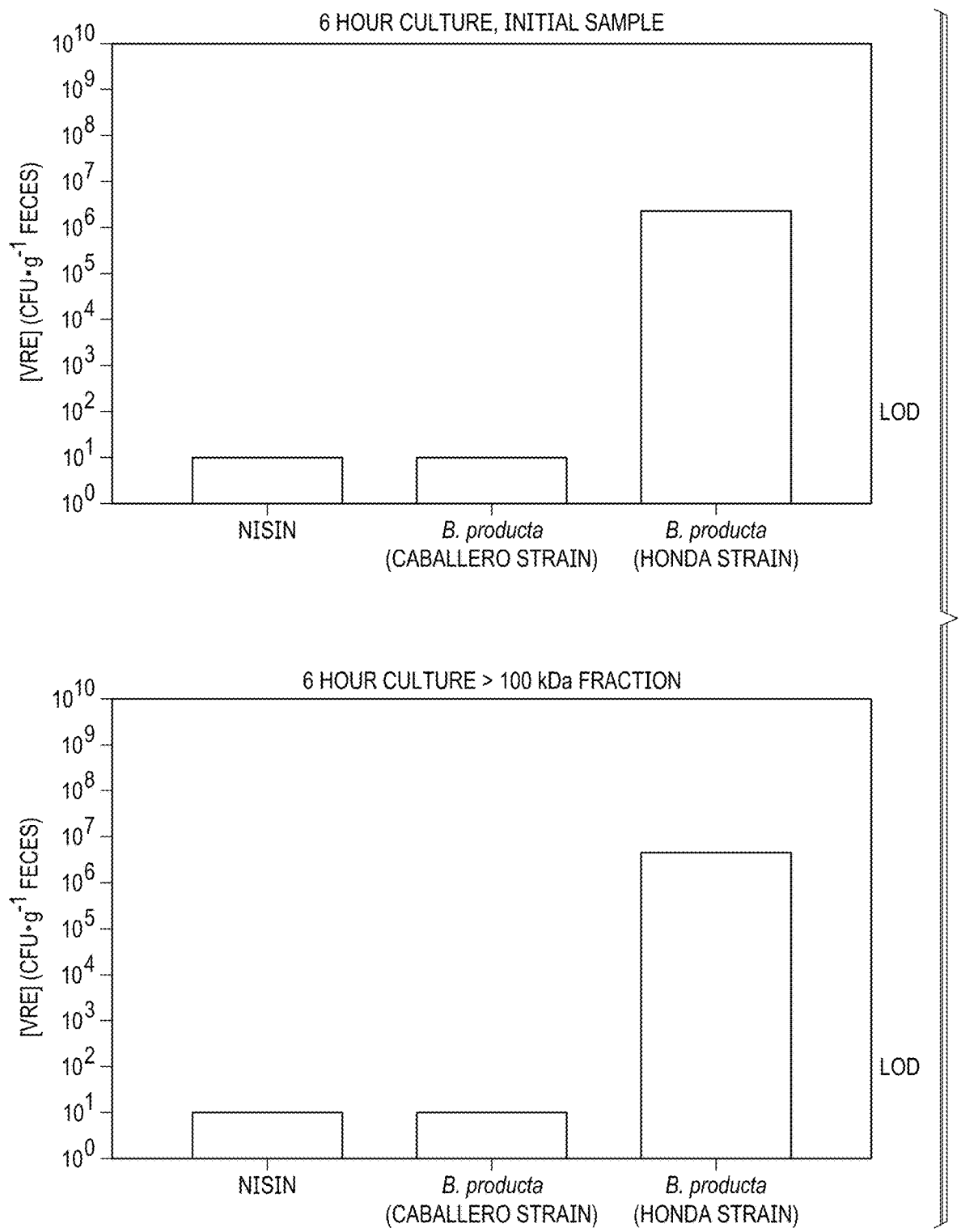
FIG. 31 is a set of graphs comparing the effects of the two *B. producta* strains of FIG. 24 and nisin on VRE (left panel), and the effects of size-selected culture medium fractions (right panel)

Example 16: Nisin and *B. producta*'s Inhibitor have Similar Inhibiting Fractions $10^7$ CFU/mL *B. producta* Caballero strain or Honda strain were cultured with $10^4$ CFU/mL VRE for 0, 6, or 24 hours anaerobically at 37° C. in BHIS. The culture supernatant at 0, 6, and 24 hours was filtered through a 0.22 μm filter. 1 mg of nisin extract powder per 1 mL of culture medium was also prepared. The samples were inoculated with $10^3$ CFU/mL VRE the cultured for 6 hours anaerobically at 37° C. VRE CFU were quantitated and results are presented in FIG. 31, left panel. The *B. producta* Caballero strain, but not the Honda strain inhibited VRE. The Caballero strain inhibited VRE with an efficacy similar to that of nisin. Both types of samples were concentrated by ultrafiltration with a molecular weight cut off greater than 100 kDa, then diluted with fresh culture medium to their original volumes. The samples were inoculated with $10^3$ CFU/mL VRE the cultured for 6 hours anaerobically at 37° C. VRE CFU were quantitated and results are presented in FIG. 31, right panel.

The *B. producta* Caballero strain, but not the Honda strain inhibited VRE. The Caballero strain inhibited VRE with an efficacy similar to that of nisin.

Example 17: Nisin and *B. producta*'s Inhibitor Share Similar Cation Exchange Chromatography Elution Profiles

Figure 32:
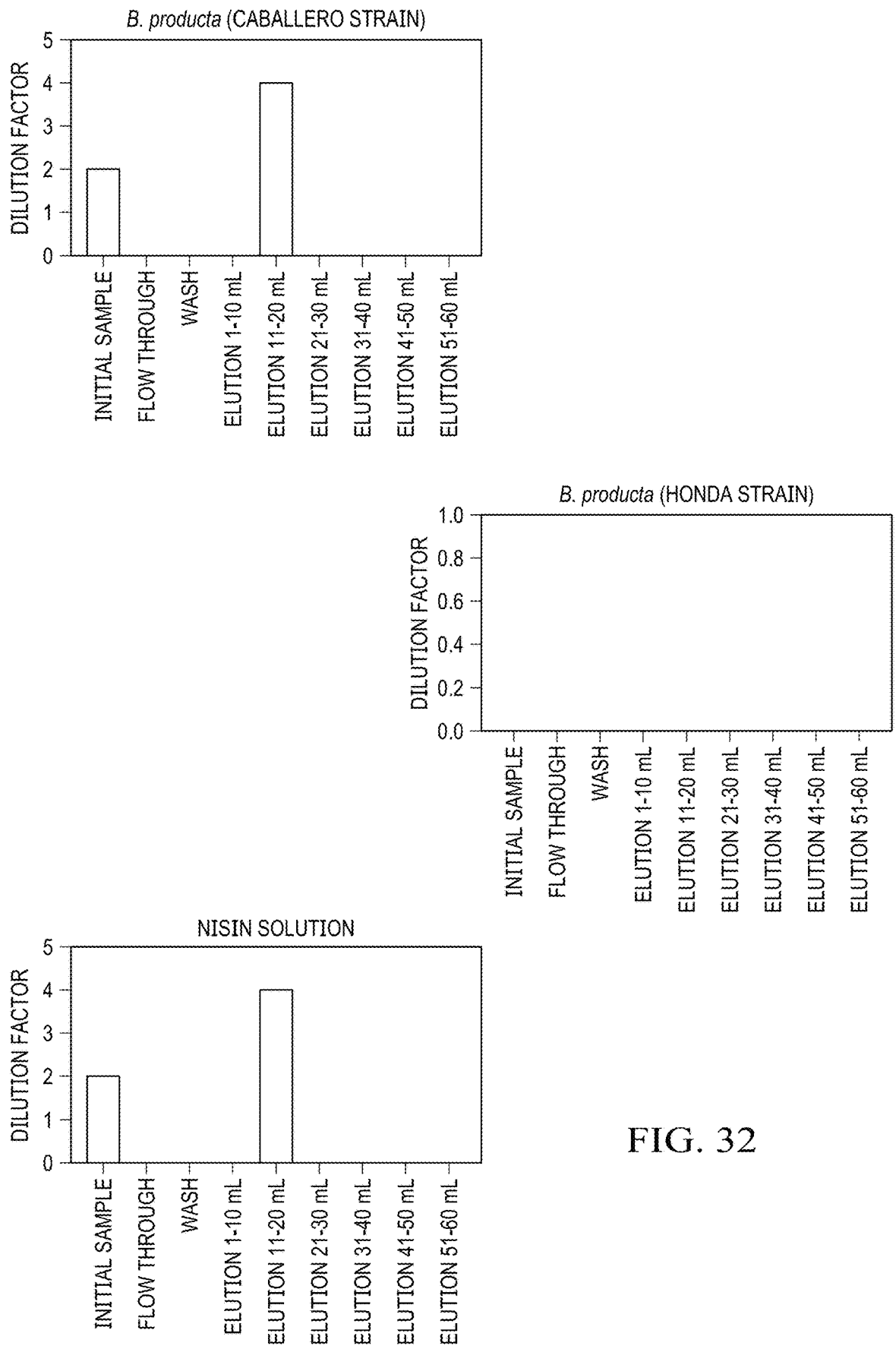
FIG. 32 is a set of graphs showing the effects on VRE of fractions from cationic exchange chromatography of the two *B. producta* culture supernatants of FIG. 24 (top panels) and nisin fractions (bottom panel)

*B. producta* protein extracts were prepared by culturing $10^7$ CFU/mL *B. producta* Caballero strain or Honda strain for 24 hours anaerobically at 37° C. in BHIS. The culture supernatant was filtered through a 0.22 μm filter. Varying concentrations of ammonium sulfate were added to the filtered culture supernatant to precipitate proteins. The precipitates were resolubilized in PBS (2 mg/mL), then dialyzed. The dialyzed solutions were restored to 10% of their original volumes with 20 mM MES solution. The pH was adjusted to 6 and the solutions were stirred to ensure all proteins were fully dissolved. A nisin solution was prepared by dissolving 1 mg of nisin extract powder in 1 mL of 20 mM MES solution. Cationic exchange chromatography was performed using Sepharose beads in a column with sample flow rate of 0.6 mL/min. The columns were washed with of 20 mM MES, pH=6, then proteins were eluted with 20 mM MES+1 M NaCl, pH=6, into 10 mL fractions. Elution fractions were dialyzed against PBS then added to VRE culture ($10^3$ CFU/mL VRE) at several different dilutions (serial 1:2 dilutions in BHIS until a dilution of 1:4096 was achieved) for 6 hours. VRE growth was monitored by incubating each sample under anaerobic conditions at 37° C. for 24 hours. The highest dilution from each fraction where there was no visible VRE growth (no pellet or turbidity) is reported in FIG. 32.

The Caballero strain sample showed a profile similar to that of nisin, while the Honda strain did not.

Example 18: Heterologous Expression of Lantibiotic Genes Still Results in VRE Inhibition

Figure 33:
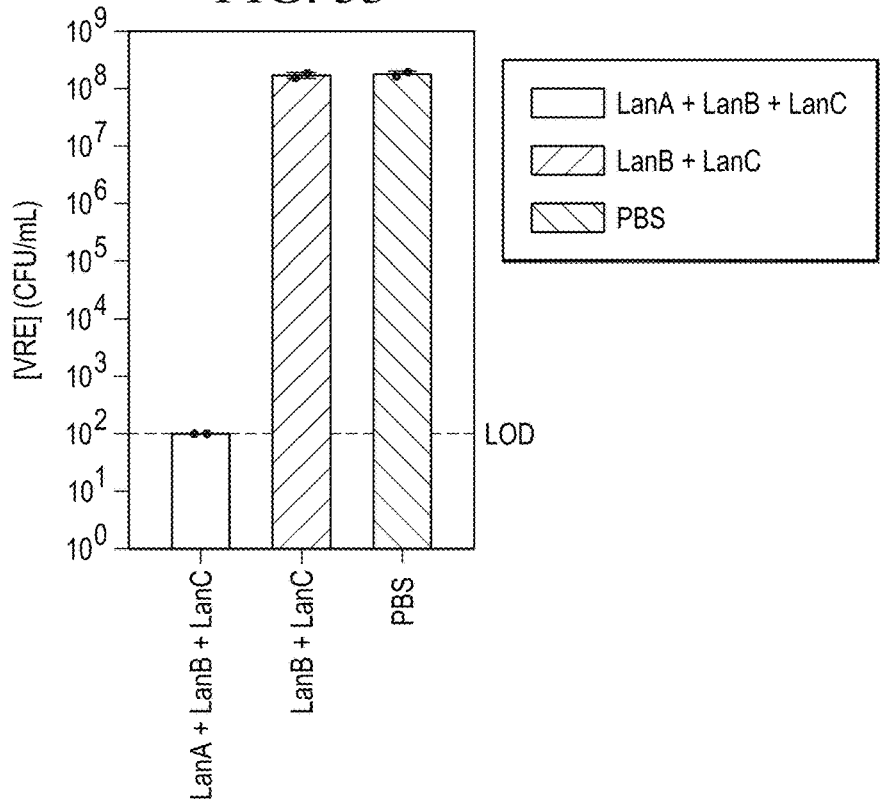
FIG. 33 is a graph of the effects of expression of various lantibiotic operon genes in *Escherichia coli* (*E coli*) and the subsequent purification of the lantibiotic on VRE cultures.

*E. coli* BL21(DE3) were transformed with vector constructs containing His-tagged-Lan A, Lan B (pRSFDuet-1 backbone) and Lan C (pCDFDuet-1 backbone) genes. The transformed *E. coli* was inoculated in terrific broth and grown to an OD=0.3-0.4 at 37° C. The culture was subsequently induced with Isopropyl β-D-1-thiogalactopyranoside (IPTG) (1 mM) and incubated for an additional 16 hours at 18° C. Cells were then harvested and resuspended in lysis buffer and lysed with an ultrasonic homogenizer. The supernatant was collected and passed through a Nickle-Nitrilotriacetic acid (Ni-NTA) column. The eluted fraction was treated with 21 uM trypsin for 3 hours at 37° C., and subsequently washed and concentrated in PBS by ultrafiltration with a molecular weight cutoff of 3 kD. The concentrate was diluted 1:2 with fresh medium and the samples were inoculated with $10^3$ CFU/mL VRE then cultured for 24 hours anaerobically at 37° C. VRE CFU were quantitated and results are presented in FIG. 33.

*E. coli* transformed with LanA, LanB, and LanC inhibited VRE, while those transformed with only LanB and LanC did not, thus establishing that heterologous expression of *B. producta* lantibiotic genes in other bacterial species also results in a factor (the lantibiotic) that inhibits VRE.

Figure 34:
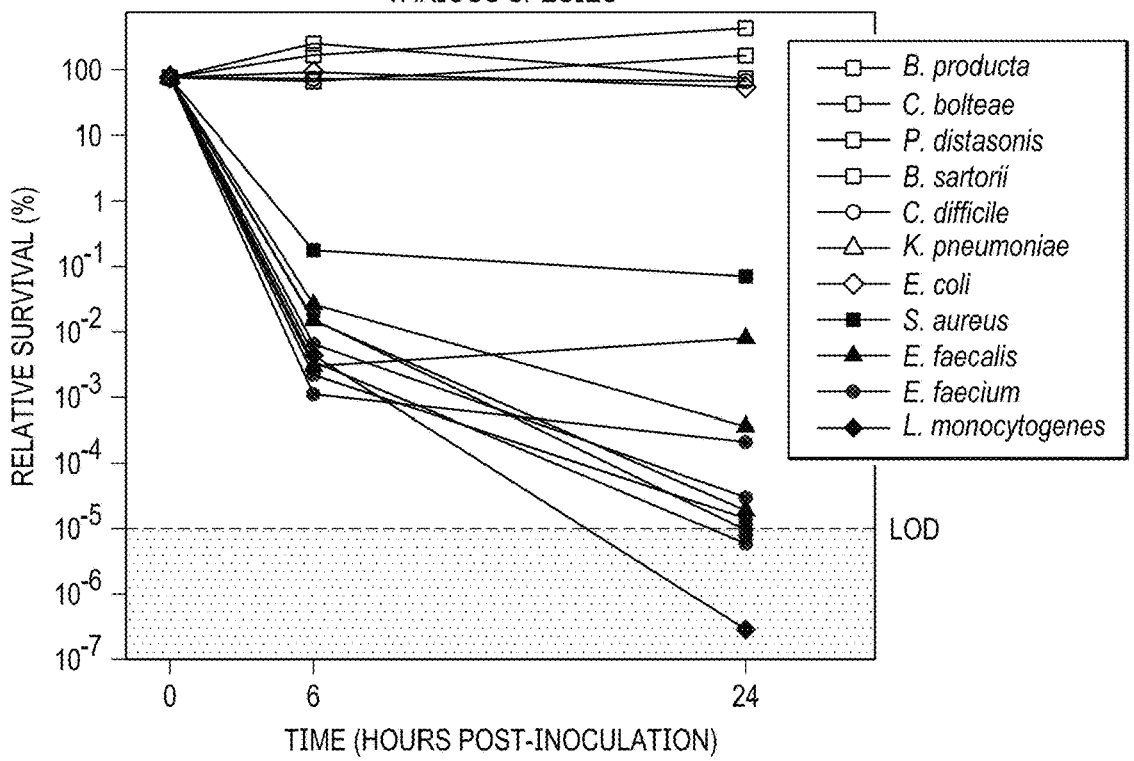
FIG. 34 is a graph of the effects on various gram-positive bacteria of the *B. producta* factor (which is a lantibiotic according to this disclosure)

Example 19: The Inhibitor has Broad-Spectrum Activity Against Exogenous, Gram Positive Bacteria $10^7$ CFU/mL *B. producta* was cultured for 0, 6, 24 hours in BHIS anaerobically at 37° C. The culture supernatant at 0, 6, and 24 hours was filtered through a 0.22 μm filter, then concentrated by ultrafiltration with a molecular weight cut off greater than 100 kDa. The concentrated culture supernatant was then diluted to the original volume with fresh BHIS culture medium. $10^3$ CFU/mL VRE, *B. producta, C. bolteae, P. distasonis, B. sartorii, C. difficile, K pneumoniae, E. coli, S. aureus, E. faecalis, E. faecium,* or *L monocytogenes* were cultured for 6, 24, or 48 hours anaerobically at 37° C. Bacteria CFU were quantitated and results are presented in FIG. 34.

Results show bacterial survival with the addition of *B. producta* culture extract to the culture medium relative to bacterial survival with the addition of a negative control (only medium with no *B. producta*) extract to the culture medium. The results indicate that the *B. producta* factor inhibited *S. aureus, E. faecalis, E. faecium,* and *L. monocytogenes,* but not *B. producta, C. bolteae, P. distasonis, B. sartorii, C. difficile, K. pneumoniae,* or *E. coli*. Thus, gram-positive bacteria were susceptible to the lantibiotic, while gram negative bacteria were not. *B. producta* was not susceptible, typical of gram-positive bacteria and lantibiotics they produce; it does little good for the bacteria to inhibit its own growth. *C. bolteae* and *C. difficile*, while gram-positive, belong to the Clostridiales order, as does *B. producta*, and are likely to also have resistance to lantibiotics produced by *B. producta* due to the presence of the same or similar resistance genes.

Figure 35:
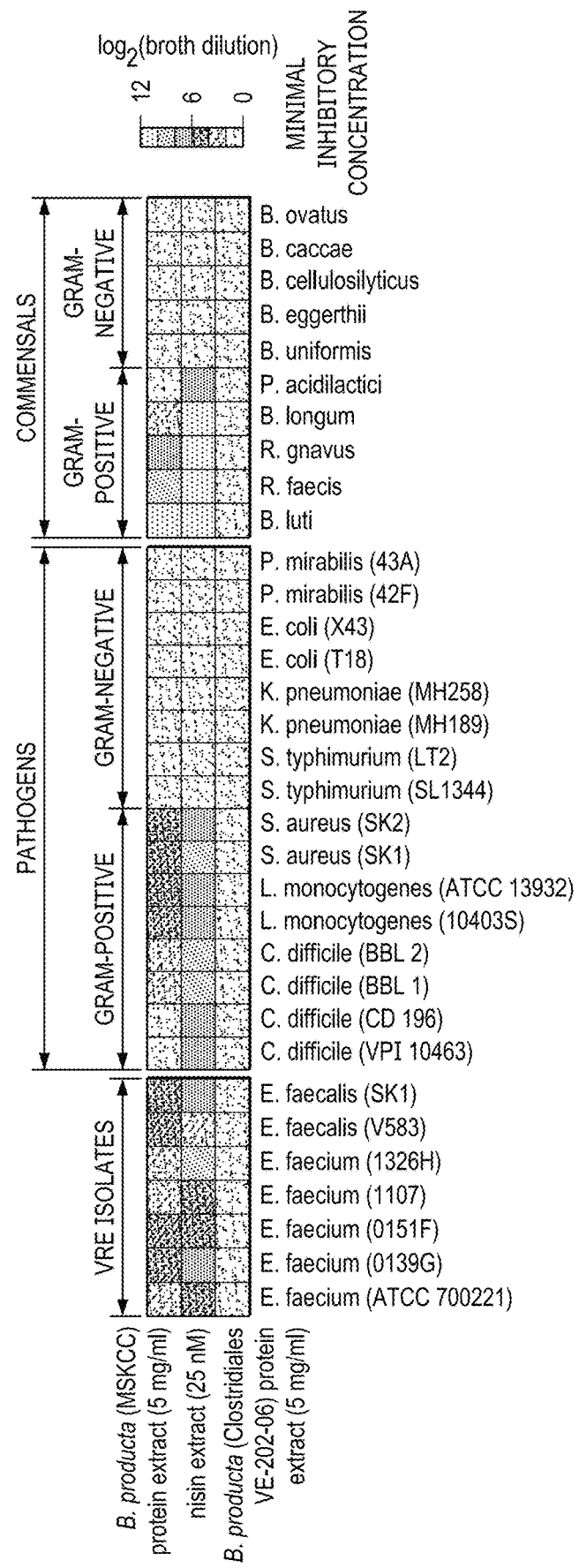
FIG. 35 is a graphs showing the effects of the *B. producta* factor (which is a lantibiotic according to this disclosure) strains on various gram-positive bacteria, including various VRE strains, other pathogenic bacteria, and commensal bacteria.

$10^7$ CFU/mL *B. producta* Caballero strain or Honda strain was cultured for 24 hours in BHIS anaerobically at 37° C. The culture supernatant was filtered through a 0.22 μm filter. Ammonium sulfate was added to the filtered culture supernatant at varying concentrations to precipitate proteins. Precipitated proteins were resolubilized in water (5 mg/mL) and dialyzed. The dialyzed protein or nisin (1:2) were serially diluted with fresh BHIS across a row of wells in a 96 well plate per gram-positive bacteria strain. $10^5$ CFU/mL of various gram-positive bacterial strains indicated in FIG. 35 were cultured for 24 hours anaerobically at 37° C. The minimum inhibitory concentration (highest dilution at which gram-positive bacteria growth was inhibited) was thus identified.

The results also indicate that the *B. producta* Caballero strain lantibiotic broadly inhibits gram-positive bacteria.

Example 20: A Mixture of Seven Bacteria Restores Colonization Resistance Against VRE in the Presence of Antibiotics A mixture of seven bacteria, *P. distasonis, B. producta* (non-lantibiotic-producing strain), *B. sartorii, C. innocuum, C. bolteae, A. muciniphila,* and an unclassified *Blautia*, were tested for their ability to restore colonization resistance in mice to vancomycin-resistant *E. faecium*. These bacteria were chosen for the intrinsic tendency of certain bacteria in the group to be resistant to ampicillin and the intrinsic ability of other bacteria in the group to synthesize secondary bile acids, or other factors.

Experiments were carried out using 6-8 week-old C57BL/6 female mice purchased from The Jackson Laboratory (Bar Harbor, ME) and housed in sterile cages with irradiated food and acidified water. 0.5 g/L ampicillin (Fisher Scientific, Hampton, NH) was administered to animals in the drinking water and changed every 4 days. Starting 24 hours after antibiotic administration, mice were treated with 3 doses (administered daily) of either PBS or a suspension of 7 bacteria (*P. distasonis, B. producta* (non-lantibiotic-producing strain), *B. sartorii, C. innocuum, C. bolteae, A. muciniphila* and an unclassified *Blautia*). grown under anaerobic conditions (7-mix). On the next day following the last 7-mix or PBS dose, mice were dosed with about $5 \times 10^4$ colony forming units (CFU) of vancomycin-resistant *E. faecium* (VRE). Mice were single-housed at the time of dosing with VRE and treated with ampicillin for the duration of the experiment. Fecal samples were collected on days 1 and 3 post dosing to monitor VRE colonization. VRE CFU in mice feces were measured.

Figure 36:
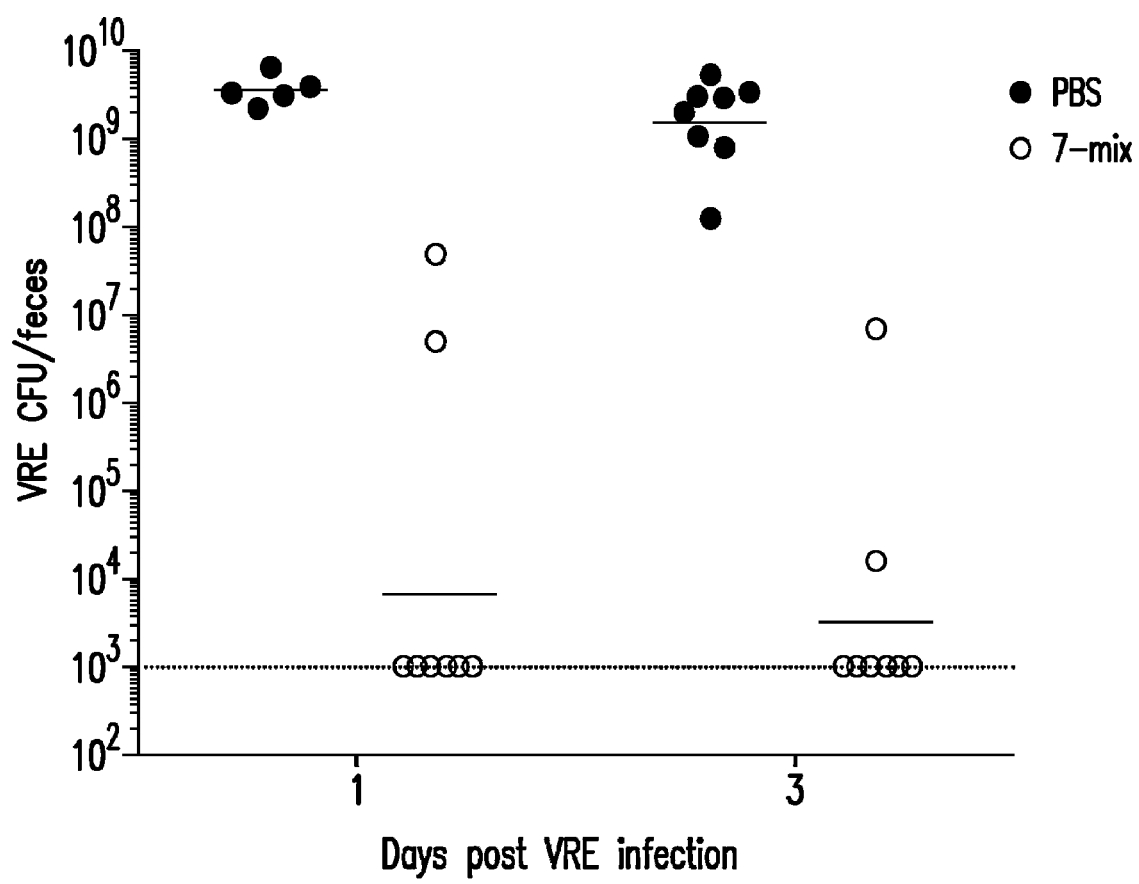
FIG. 36 is a graph of VRE colony forming units (CFU) in mice feces versus days post infection in the presence of antibiotics for mice treated with a bacterial suspension of *P. distasonis, B. sartorii* (also known as *Bacteroides chinchillae*), *B. producta* (non-lantibiotic-producing strain), *C. innocuum, A. muciniphila, C. bolteae*, and *Blautia* unclassified (7-mix) or with phosphate buffered saline (PBS).

As shown in FIG. 36 and Table 1, mice treated with the 7-mix bacterial suspension prior to VRE dosing exhibited less VRE growth (as demonstrated by fewer CFU) at both 1 and 3 days after dosing with VRE compared to control mice treated with only PBS prior to dosing with VRE. This demonstrates that the 7-mix bacterial suspension provided colonization resistance against VRE colonization in the presence of antibiotics.

Additional improvements of these results are expected if a lantibiotic or a lantibiotic-producing bacteria were included in the mixture.

TABLE 1

Effect of 7-mix bacterial suspension on VRE colonization 1 and 3 days after dosing with VRE.

| Treatment | CFUs 1 Day Post-Dosing | CFUs 1 Day Post-Dosing |
|---|---|---|
| PBS | 2.22E+09 | 2.76E+09 |
| PBS | 3.31E+09 | 4.98E+09 |
| PBS | 6.22E+09 | 3.11E+09 |
| PBS | 3.86E+09 | 2.82E+09 |
| PBS | 3.11E+09 | 1.89E+09 |
| PBS | 8.00E+05 | 1.20E+08 |
| PBS | 8.00E+05 | 7.60E+08 |
| PBS | 2.00E+06 | 1.00E+09 |
| 7-mix | 0.00E+00 | 0.00E+00 |
| 7-mix | 4.78E+07 | 1.97E+06 |
| 7-mix | 0.00E+00 | 0.00E+00 |
| 7-mix | 5.04E+06 | 1.75E+04 |
| 7-mix | 0.00E+00 | 0.00E+00 |
| 7-mix | 0.00E+00 | 0.00E+00 |
| 7-mix | 0.00E+00 | 0.00E+00 |
| 7-mix | 0.00E+00 | 0.00E+00 |
| 7-mix | 0.00E+00 | 0.00E+00 |
| 7-mix | 0.00E+00 | 0.00E+00 |

Example 21: *C. scindens* and *B. hansenii* Reduce VRE Colonization in Mice Intestines In Vitro The present example describes the effect of treating VRE growth with *C. scindens* and *B. hansenii*, two additional secondary bile acid-producing bacteria, in vivo in mice.

C57/B6 mice were treated for 1 week with 0.5 g/L ampicillin in drinking water. On day 7 they were dosed with 5×10$^8$ CFU *E. faecium* ATCC700221 (VRE) by oral gavage. Mice were withdrawn from ampicillin on day 7 and left for 3 additional days to allow the ampicillin to wash out. Mice were then individually housed (Day 0 Post-Reconstitution) and were reconstituted with 3 consecutive daily treatments (Days 0, 1 and 2 post-reconstitution) of PBS (No Treatment), 200 uL of a suspension of a naïve C57/B6 fecal pellet in PBS at a concentration of 10 mg/mL (FMT), 10$^8$ CFU of *C. scindens* ATCC35704 (*C. scindens*), 10$^8$ CFU of *B. hansenii* ATCC27752 (*B. hansenii*), or a 1:1 mix of 10$^8$ CFU *C. scindens* and *B. hansenii* (C.s.+B.h.). 3-4 mice were used per group (Fecal Microbiota Transplant (FMT) (n=3), *C. scindens* (n=4), *B. hansenii* (n=4), or a mixture of *C. scindens* and *B. hansenii* (C.s.+B.h) (n=4). Control mice (No treatment) (n=4) were untreated). VRE burden was determined from fecal pellets on days 0, 7, 15, 24 and 30 post-reconstitution by plating on Enterococcosel medium containing 8 ug/mL vancomycin and 100 ug/mL streptomycin.

A frozen aliquot (~100 mg) of each sample was suspended, while frozen, in a solution containing 500 µl of extraction buffer (200 mM Tris, pH 8.0/200 mM NaCl/20 mM EDTA), 200 µl of 20% SDS, 500 µl of phenol:chloroform:isoamyl alcohol (24:24:1), and 500 µl of 0.1 mm diameter zirconia/silica beads (BioSpec Products). Microbial cells were lysed by mechanical disruption with a bead beater (BioSpec Products) for 2 minutes, after which two rounds of phenol:chloroform:isoamyl alcohol extraction were performed. DNA was precipitated with ethanol and re-suspended in 50 µl of Tris/EDTA (TE) buffer with 100 µg/ml RNase. The isolated DNA was subjected to additional purification with QIAamp Mini Spin Columns (Qiagen).

Amplicons of the V4-V5 16S rRNA region were amplified and sequenced using an Illumina MiSeq platform for samples in the in vivo and ex vivo adoptive transfer experiments. For each sample, duplicate 50-µl PCR reactions were performed, each containing 50 ng of purified DNA, 0.2 mM dNTPs, 1.5 mM MgCl2, 1.25 U Platinum Taq DNA polymerase, 2.5 µl of 10×PCR buffer, and 0.2 µM of each primer designed to amplify the V4-V5: 563F (5'-nnnnnnnn-NNNNNNNNNNNN-AYTGGGYDTAAAGNG-3') (SEQ. ID. NO.: 3) and 926R (5'-nnnnnnnn-NNNNNNNNNNNN-CCGTCAATTYHTTTRAGT-3') (SEQ. ID. NO.: 4). A unique 12-base Golay barcode (Ns) preceded the primers for sample identification, and one to eight additional nucleotides were placed in front of the barcode to offset the sequencing of the primers. Cycling conditions were 94° C. for 3 minutes, followed by 27 cycles of 94° C. for 50 s, 51° C. for 30 s, and 72° C. for 1 minute. A condition of 72° C. for 5 minutes was used for the final elongation step. Replicate PCRs were pooled, and amplicons were purified using the Qiaquick PCR Purification Kit (Qiagen). PCR products were quantified and pooled at equimolar amounts before Illumina barcodes and adaptors were ligated on using the Illumina TruSeq Sample Preparation protocol. The completed library was sequenced on an Ilumina Miseq platform following the Illumina recommended procedures.

Sequences were analyzed using the mothur (version 1.33.3) pipeline. Potentially chimaeric sequences were removed using the UChime algorithm. Sequences with a distance-based similarity of 97% or greater were grouped into OTUs using the average neighbor algorithm and classified using the BLAST (megablast) algorithm and the GenBank 16S rRNA reference database.

Figure 37A:
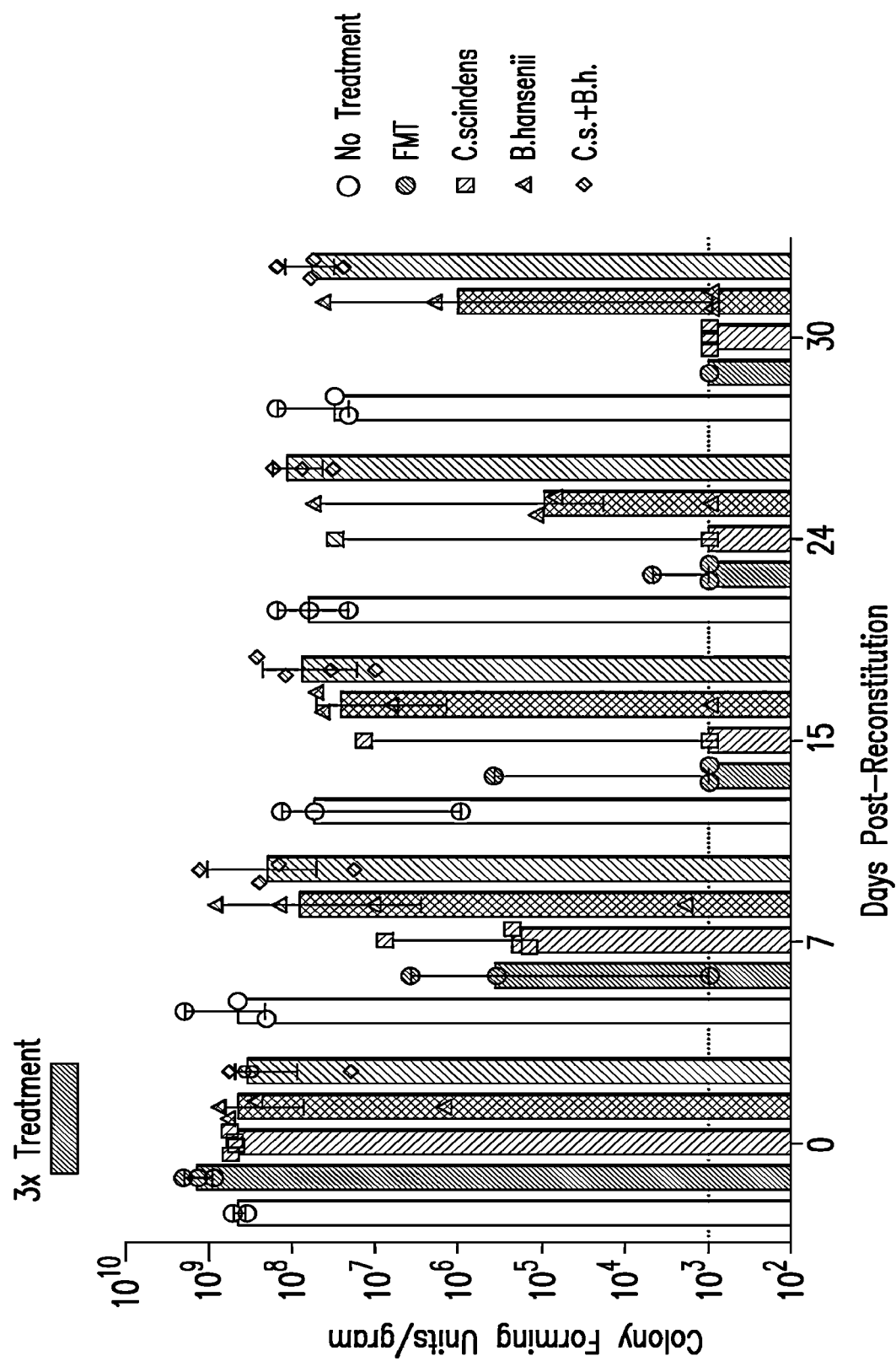
FIGS. 37A-37C are graphs showing the effects of *C. scindens* and *B. hansenii* on VRE intestinal clearance in mice in vivo over a 30 day study period.

As shown in FIG. 37A, treatment of VRE dosed mice with FMT or with *C. scindens* or *B. hansenii* alone reduced VRE burden over the 30-day study. VRE growth was at the lowest detectable limit by day 15 post-reconstitution for FMT and *C. scindens* treated animals. A combination of *C. scindens* and *B. hansenii* did not reduce VRE burden in this example.

Figure 37B:
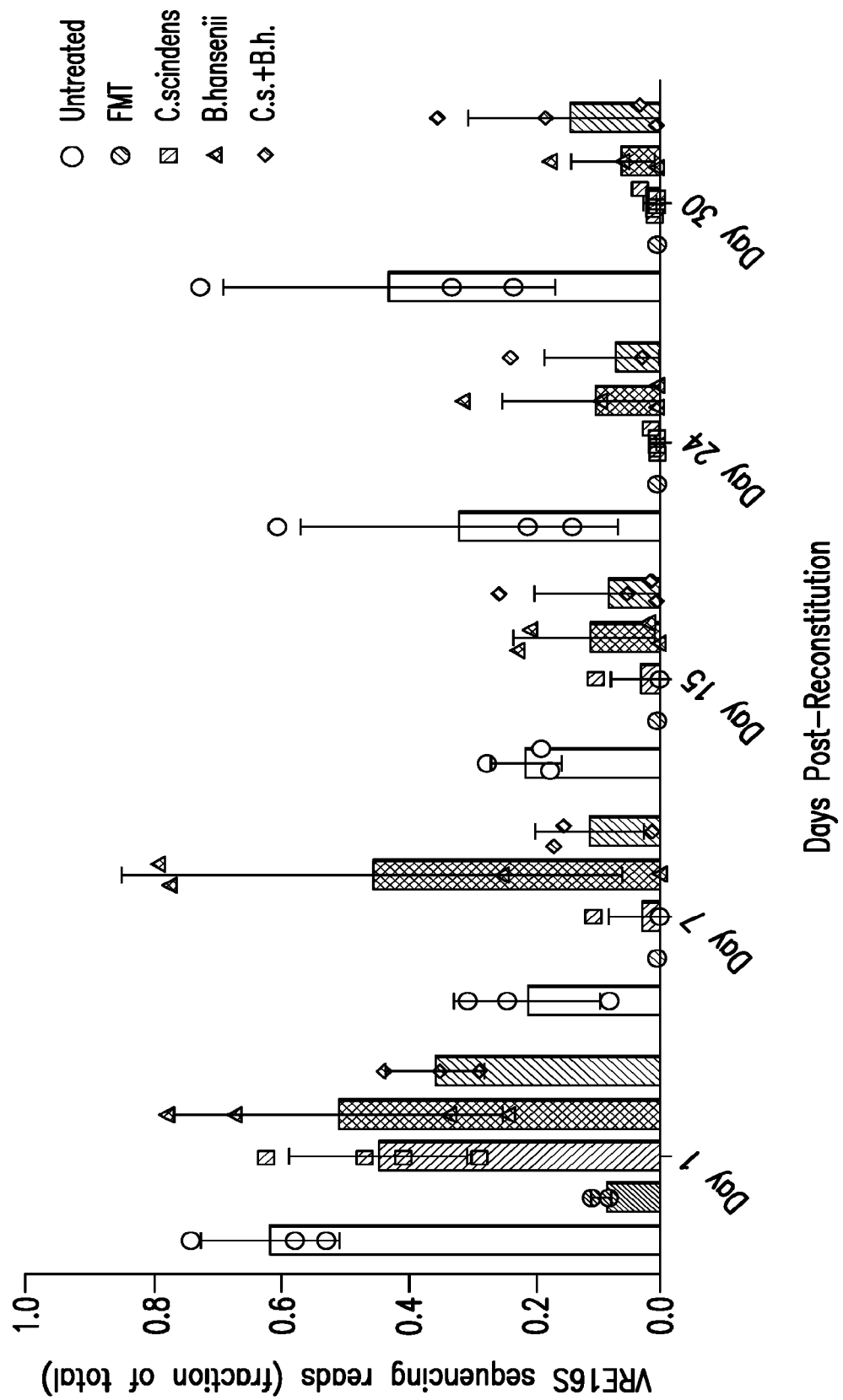
Figure 37C:
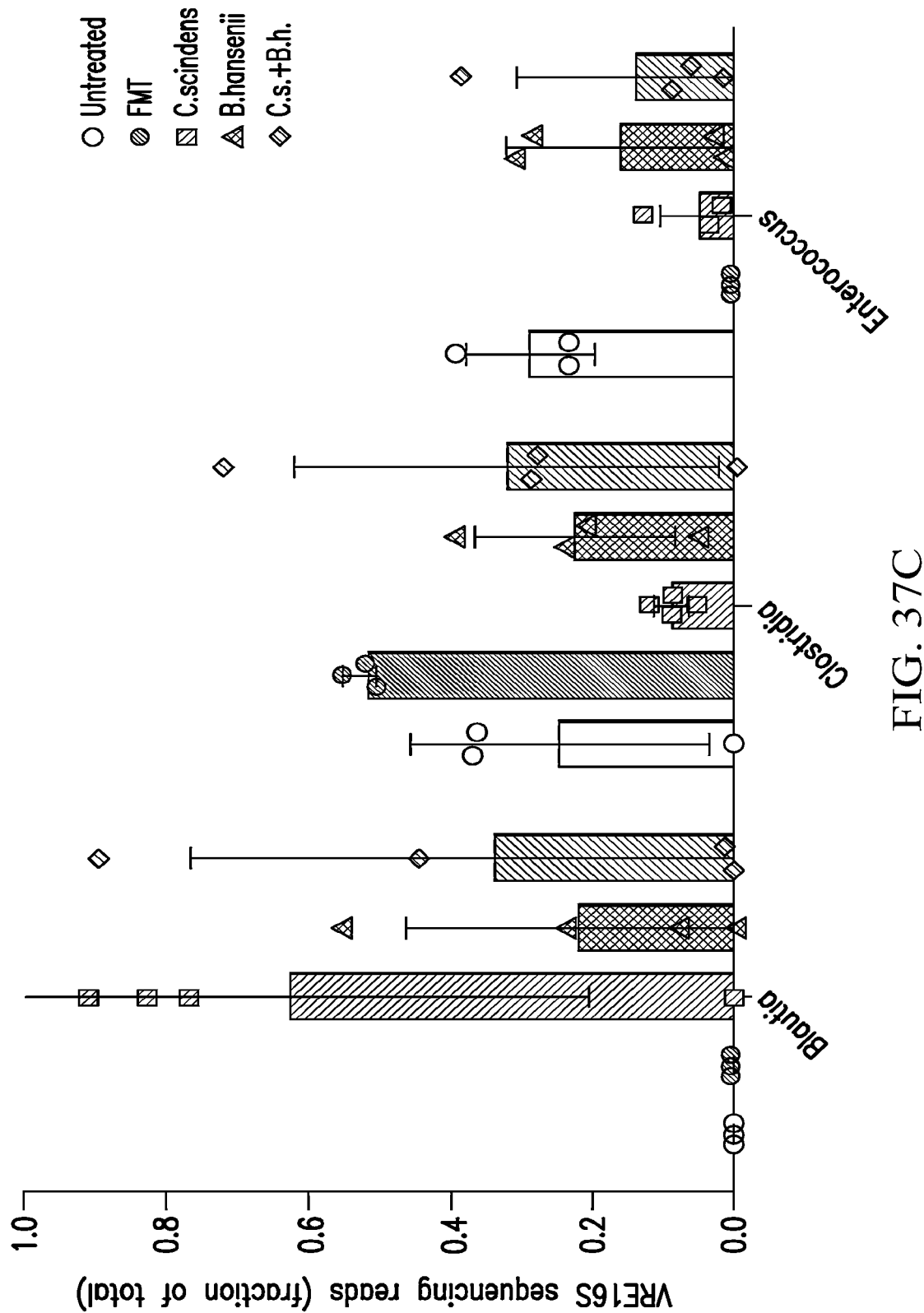

However, the amount of VRE spp. 16S sequence reads was decreased by day 15 post-reconstitution for each of the treatment conditions (p ~0.1 overall). (See FIG. 37B). Additionally, at day 15 post-reconstitution, mice treated with *C. scindens* alone that cleared VRE had very high amounts of *Blautia* spp. 16S sequence reads (see FIG. 37C), while a single mouse treated with *C. scindens* alone which had not cleared VRE at day 15 had undetectable amounts of *Blautia* spp. 16S sequence reads. Similarly, mice treated with *B. hansenii* alone, or a combination of *C. scindens* and *B. hansenii*, exhibited low amounts of *Blautia* spp. 16S sequence reads at day 15 post-reconstitution. (See FIG. 37C).

These data demonstrate that *B. hansenii* can play a role in reconstitution in the presence of *C. scindens*, but the relationship is complex. Additional improvements of these results are expected if a lantibiotic or a lantibiotic-producing bacteria were included as well.

Example 22: A Combination of *C. scindens* and *B. hansenii* Reduces VRE Growth in Intestinal Extracts Ex Vivo Independent of Bile Acids To further understand their relationship and effects on VRE, *C. scindens* and *Blautia hansenii* were tested for their ability to restore colonization resistance to VRE in mouse intestinal extracts ex vivo.

C57/B6J mice were treated for 3 days with 200 µg of clindamycin by intraperitoneal injection and sacrificed on day 4. Intestinal content was harvested from the small intestine and was transferred to an anaerobic chamber and resuspended in reduced anaerobic PBS to a concentration of 10 mg/mL. Content was then extracted with 50% w/v cholestyramine (a bile acid sequestrant) or nothing for 1 hour with rotation to allow examination of any additional effects of bile acids, which inhibit some bacterial growth. Content was then distributed to 96-well plates and inoculated with 10$^4$ CFU of *C. scindens*, *B. hansenii*, a 1:1 mix of *C. scindens* and *B. hansenii*, or an equal amount of PBS. Cultures were then incubated at 37° C. for 6 hours, followed by inoculation with 10$^4$ CFU of VRE and overnight incubation at 37° C. in the anaerobic chamber. VRE burden was determined by plating on Enterococcosel agar containing 8 ug/mL vancomycin and 100 ug/mL streptomycin.

Figure 38:
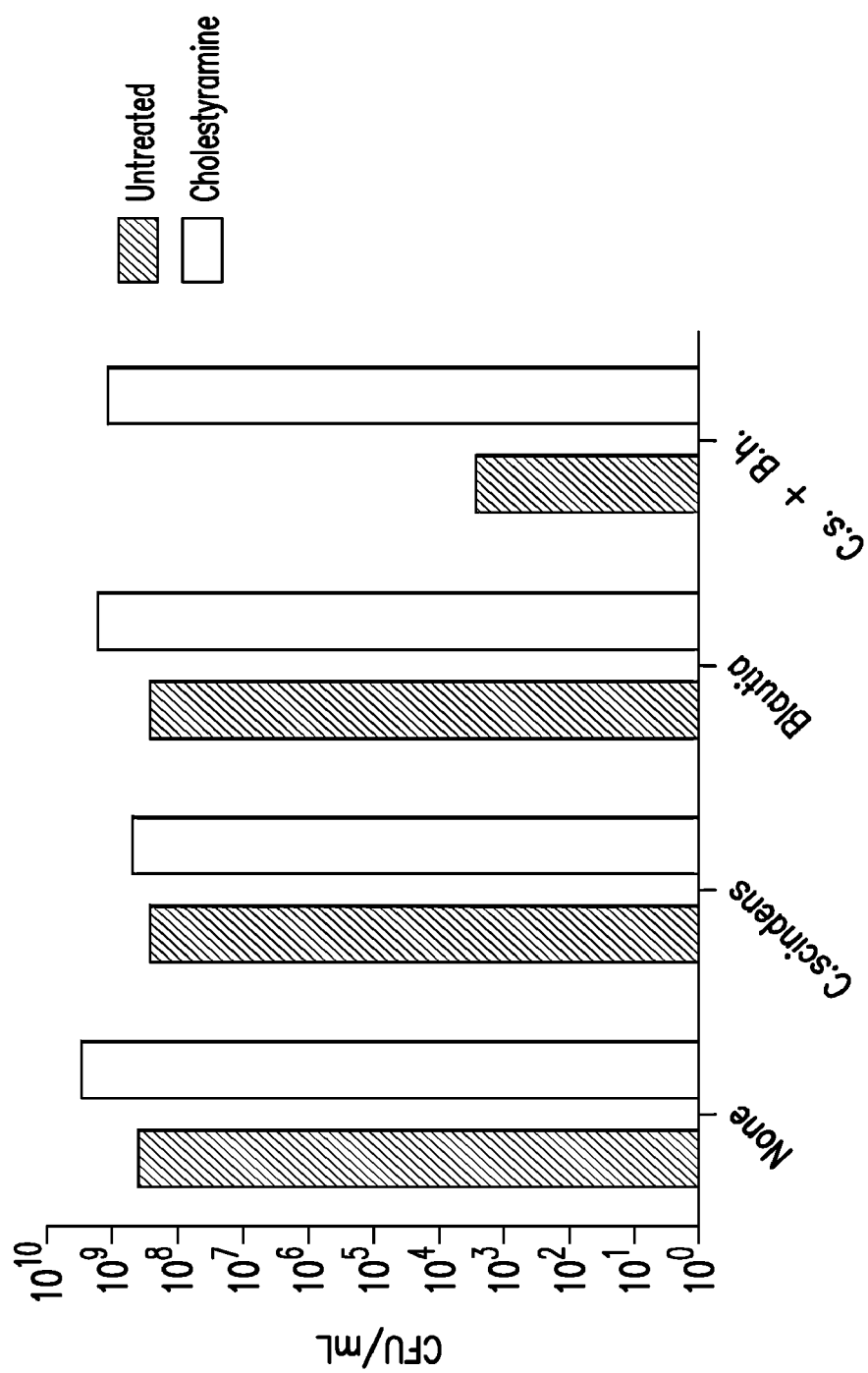
FIG. 38 is a graph of VRE CFU in intestinal extracts infected with VRE and treated with *C. scindens, B. hansenii*, a mixture of *C. scindens* and *B. hansenii*, or nothing, and also treated with cholesterylamine or untreated.

As shown in FIG. 38, mouse intestinal extracts treated with cholestyramine, a bile acid binding resin, exhibited greater VRE microbial growth than untreated cultures following VRE inoculation. Addition of a mixture of *C. scindens* and *B. hansenii* to the extracts reduced VRE microbial growth in the untreated extracts following VRE inoculation compared to extracts treated with cholestyramine. These data indicate that, although bile acids affect VRE growth in untreated samples, they have a much greater effect on VRE growth (inhibition) in samples treated with a mixture of *C. scindens* and *B. hansenii*. This indicates that the ability of *C. scindens* and *B. hansenii* to produce secondary bile acids is likely at least partially responsible for their effects in controlling VRE. Accordingly, these data demonstrate that inclusion of these species or species having similar activity, for example, in this assay, are useful for treating and/or preventing VRE infection. Additional improvements of Example 23: Combinations of *A. muciniphila, E. dolichum, B. producta* (Non-Lantibiotic-Producing Strain), *Blautia* Unclassified, *C. bolteae, B. sartorii*, and *P. distasonis* Reduce VRE Growth in Intestinal Extracts In Vivo Different combinations of seven bacteria, *A. muciniphila, E. dolichum, B. producta* (non-lantibiotic-producing strain), an unclassified *Blautia* species, *C. bolteae, B. sartorii*, and *P. distasonis* were tested for their ability to restore colonization resistance to VRE in mouse intestinal extracts in vivo. These bacteria were chosen for the intrinsic ampicillin resistance of some and the intrinsic ability of others to produce secondary bile acids, or other factors.

Experiments were carried out using 6-8 week-old C57BL/6 female mice purchased from The Jackson Laboratory (Bar Harbor, ME) and housed in sterile cages with irradiated food and acidified water. 0.5 g/L ampicillin (Fisher Scientific, Hampton, NH) was administered to animals in the drinking water and changed every 4 days. Starting 24 hours after antibiotic administration, mice were treated with 3 doses (administered daily) of either saline (PBS) or a suspension of bacteria as indicated below that were grown under anaerobic conditions. On the next day following the last bacterial suspension or PBS dose, mice were dosed with about $5 \times 10^4$ colony forming units (CFU) of vancomycin-resistant *E. faecium* (VRE). Mice were single-housed at the time of dosing with VRE and treated with ampicillin for the duration of the experiment. Fecal samples were collected on days 1, 3 and 6 or 8 post dosing for mice treated with the 7-mixture suspension, and on day 3 post dosing for mice treated with the other mixtures, to monitor VRE colonization. VRE CFU in mice feces were measured.

The bacterial suspensions used are as follows:
- 7-Mix: *A. muciniphila, E. dolichum, B. producta* (non-lantibiotic-producing strain), *Blautia* unclassified, *C. bolteae, B. sartorii*, and *P. distasonis*
- 5-Mix: *A. muciniphila, B. producta* (non-lantibiotic-producing strain), *C. bolteae, B. sartorii*, and *P. distasonis*
- 4-Mix: *B. producta* (non-lantibiotic-producing strain), *C. bolteae, B. sartorii*, and *P. distasonis*
- 3-Mix A: *C. bolteae, B. sartorii*, and *P. distasonis*
- 3-Mix B: *B. producta* (non-lantibiotic-producing strain), *B. sartorii*, and *P. distasonis*
- 2-Mix A: *B. producta* (non-lantibiotic-producing strain), and *C. bolteae*
- 2-Mix B: *B. sartorii*, and *P. distasonis*

Figure 39A:
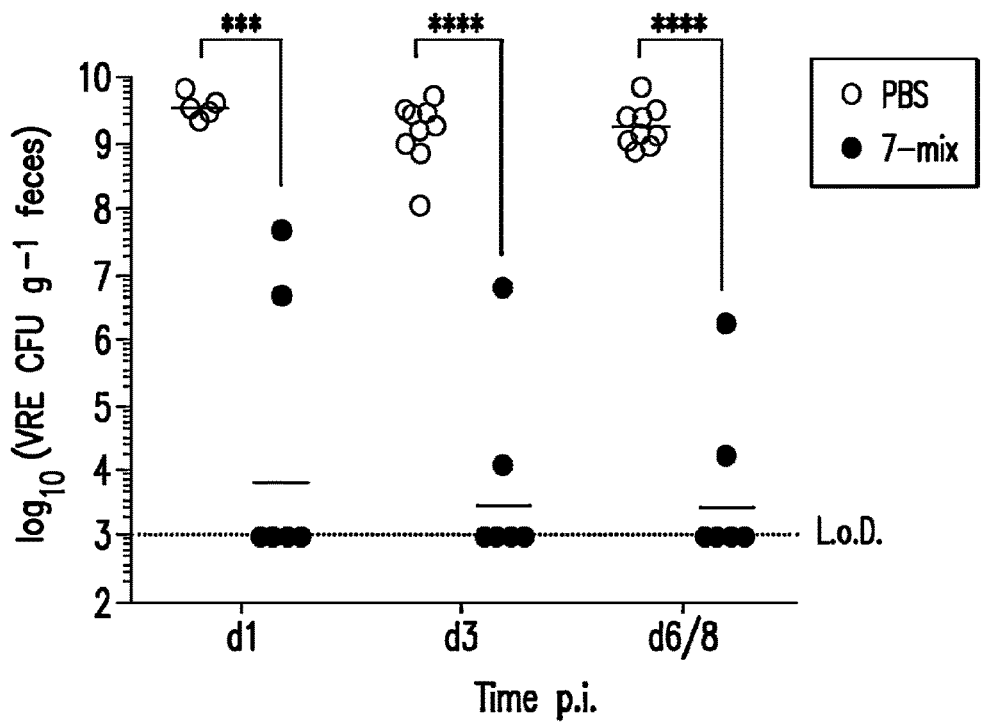
FIGS. 39A and 39B are graphs showing the effects of a bacterial suspension of different mixtures of *A. muciniphila, E. dolichum, B. producta* (non-lantibiotic-producing strain), *Blautia* unclassified, *C. bolteae, B. sartorii*, and *P.s distasonis* compared to PBS on VRE intestinal clearance in mice in vivo.
Figure 39B:
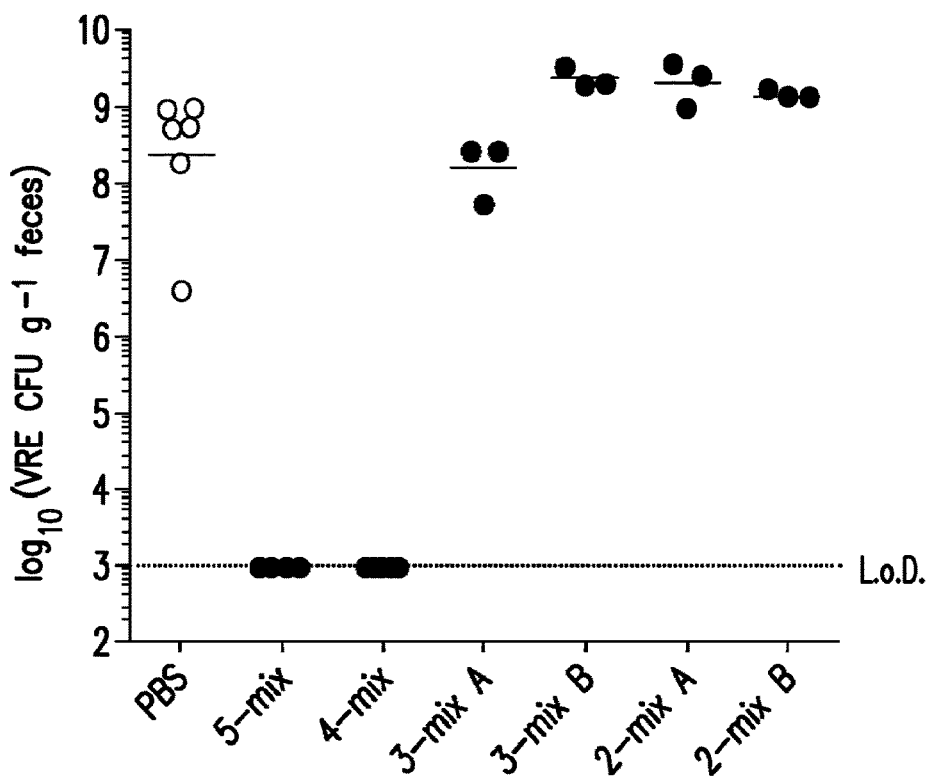

As shown in FIG. 39A and FIG. 39B, mice treated with the 7-mix bacterial suspension prior to VRE exposure exhibited less VRE growth (as measured by CFU) at days 1, 3 and 6 or 8 after exposure to VRE compared to control mice (treated with PBS prior to exposure to VRE). Mice treated with the 5-mix and 4-mix bacterial suspension prior to VRE exposure also exhibited less VRE growth (as measured by CFU) at day 3 after exposure to VRE compared to control mice (treated with PBS prior to exposure to VRE). *B. sartorii*, and *P. distasonis* are ampicillin-resistant bacteria. When antibiotic treatment was continued during and/or after treatment with bacterial mixtures, these two strains are included in the bacterial mixtures.

Overall, the data show that, although mixtures or smaller numbers of bacteria can have some effect, mixtures of multiple bacteria appear to be more effective at controlling VRE growth in vivo. These data also indicate that interactions between the different bacteria are complex.

Additional improvements of these results are expected if a lantibiotic or a lantibiotic-producing bacteria were included in the mixture.

Example 24: Combinations of *C. bolteae, B. producta* (Non-Lantibiotic-Producing Strain), *B. sartorii*, and *P. distasonis* Reduce VRE Growth in Intestinal Extracts In Vivo Combinations of *C. bolteae, B. producta* (non-lantibiotic-producing strain), *B. sartorii*, and *P. distasonis* were tested for their ability to clear VRE from mouse intestines in vivo.

Experiments were carried out using 6-8 week-old C57BL/6 female mice purchased from The Jackson Laboratory (Bar Harbor, ME) and housed in sterile cages with irradiated food and acidified water. 0.5 g/L ampicillin (Fisher Scientific, Hampton, NH) was administered to animals in the drinking water and changed every 4 days. Mice were treated with ampicillin 7 days prior to dosing about $5 \times 10^4$ colony forming units (CFU) of vancomycin-resistant *E.s faecium* (VRE). Ampicillin treatment was discontinued when the mice were dosed with VRE. The mice were then treated with 3 doses (administered daily) of either saline (PBS) or a suspension of bacteria as indicated below that were grown under anaerobic conditions. Treatment occurred 3, 4 and 5 days after VRE dosing (i.e., days 0, 1 and 2 of the study). Fecal samples were collected on days 0, 3, 6, 9 and 12 post-treatment with the bacterial suspensions to monitor VRE clearance from mouse intestines. Small intestine (ileum) samples were collected on day 12 post-exposure to bacterial mixtures.

The bacterial suspensions used are as follows:
- *C. bolteae* and *B. producta* (non-lantibiotic-producing strain) (C.b.+B.p.)
- *C. bolteae, B. producta* (non-lantibiotic-producing strain), *B. sartorii*, and *P. distasonis* (C.b.+B.p.+P.d.+B.s)

Figure 40A:
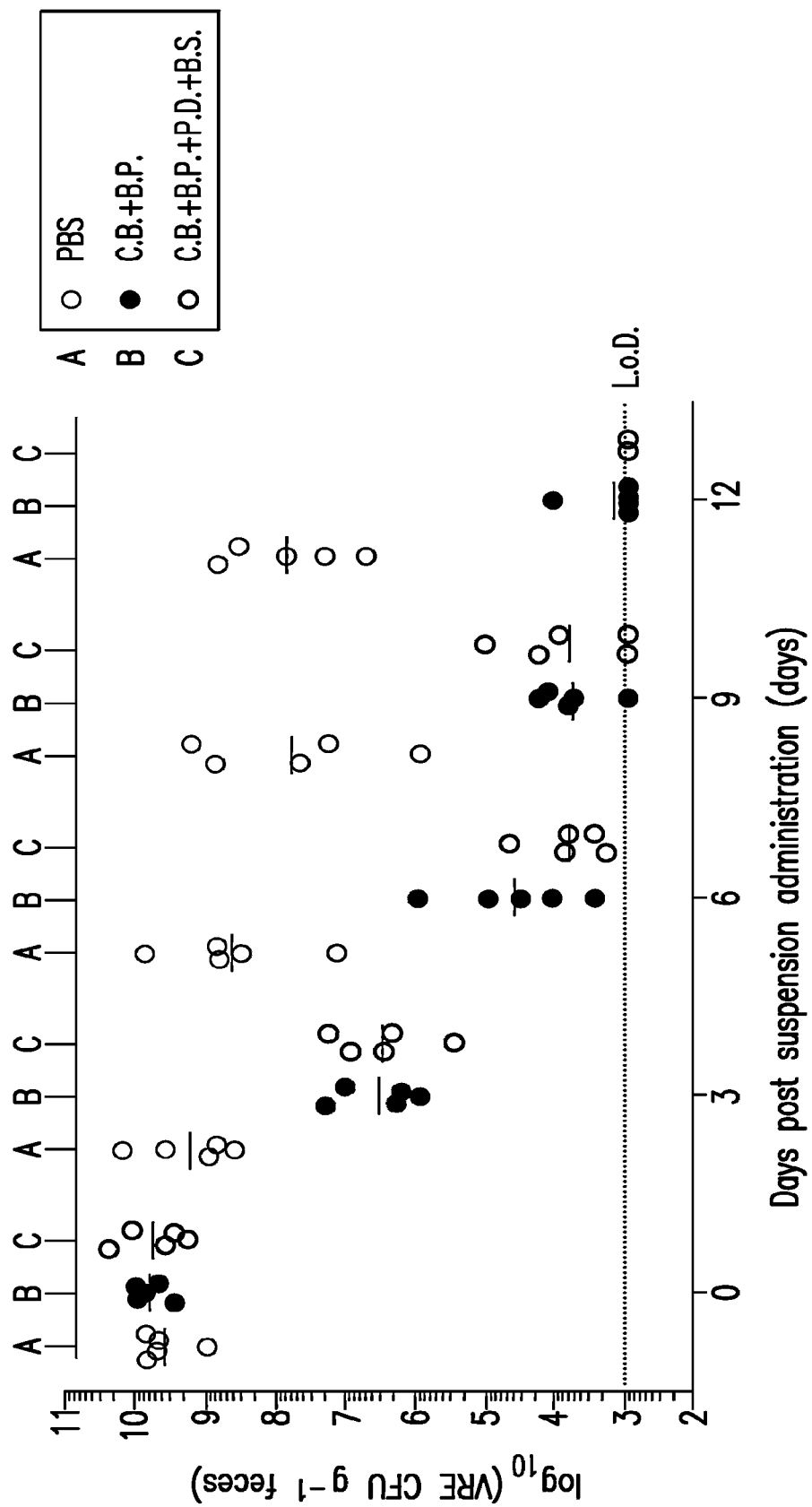
FIGS. 40A and 40B are graphs showing the effects of a mixture of *C. bolteae* and *B. producta* (C.b+B.p), or a mixture of *C. bolteae, B. producta* (non-lantibiotic-producing strain), *P. distasonis* and *B. sartorii* (C.b.+B.p+P.d.+B.s) on VRE intestinal clearance in mice in vivo.
Figure 40B:
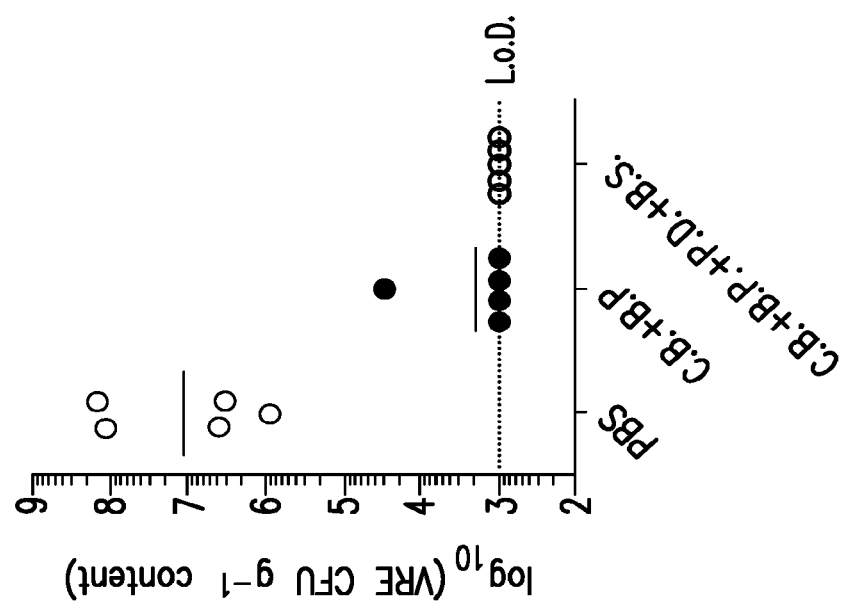
Figure 41:
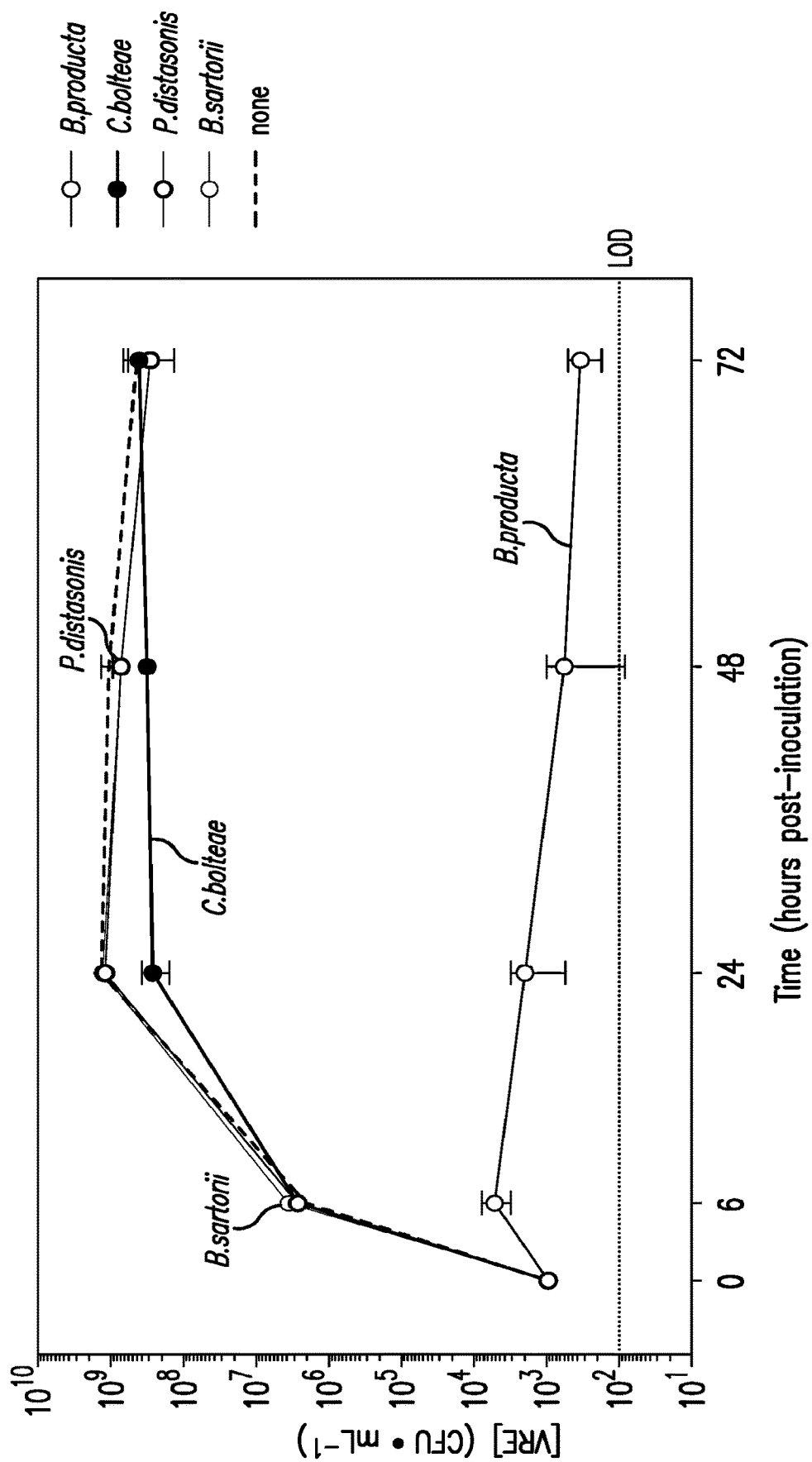
FIG. 41 is a graph of VRE CFU after in vitro co-culture with *C. bolteae, B. producta* (non-lantibiotic-producing strain), *B. sartorii*, or *P. distasonis* alone.

As shown in FIG. 40A, mice treated with either bacterial suspension after VRE dosing exhibited greater VRE clearance (as measured by CFU) at days 3, 6, 9 and 12 post-treatment with either bacterial suspension compared to control mice (treated with PBS after exposure to VRE). As shown in FIG. 40B, small intestine (ileum) samples also exhibited VRE clearance on day 12 post-exposure to either bacterial suspension. "L.o.D." is the limit of detection.

These data indicate that both bacterial suspensions were effective at clearing VRE, with the mixture also containing *B. sartorii*, and *P. distasonis* being slightly more effective. Accordingly, a bacterial pharmaceutical composition useful for treating VRE can include *B. sartorii*, and *P. distasonis* or bacteria having similar features, e.g., ampicillin-resistance. Additional improvements of these results are expected if a lantibiotic or a lantibiotic-producing bacteria were included in the bacterial pharmaceutical composition.

Example 25: Effects of *C. bolteae, B. producta* (Non-Lantibiotic-Producing Strain), *B. sartorii*, and *P. distasonis* Alone on VRE Growth In Vitro To investigate the effects of *C. bolteae, B. producta* (non-lantibiotic-producing strain), *B. sartorii*, and *P. distasonis* alone on VRE, $10^7$ CFU/ml of the test bacteria, or no bacteria was co-cultured with $10^3$ CFU/mL VRE anaerobically at 37° C. in BHIS liquid medium (Brain Heart Infusion (BHI)+5 g/L yeast extract+1 g/L L-cysteine). Samples were taken and tested for VRE after 6, 24, 48, and 72 hours of co-culture. Results are presented in FIG. 6 and show that *B. producta* alone resulted in substantially less growth of VRE, even after only 6 hours of co-culture. Similar effects were not observed with the other single bacteria, suggesting that bacterial suspensions useful in controlling and clearing VRE can contain *B. producta* (non-lantibiotic-producing strain). The additional presence of *C. bolteae* further improves results. Accordingly, a bacterial pharmaceutical composition can comprises *B. producta* (non-lantibiotic-producing strain). A bacterial pharmaceutical composition can comprise *B. producta* (non-lantibiotic-producing strain) and *C. bolteae*. Additional improvements of these results are expected if a lantibiotic or a lantibiotic-producing bacteria were included in the bacterial pharmaceutical composition.

Various references and sequence accession numbers are cited herein, the contents of which are hereby incorporated by reference in their entireties. In addition, the contents of PCT patent application PCT/US16/63643, filed Nov. 23, 2016 and titled "METHODS AND COMPOSITIONS FOR REDUCING VANCOMYCIN-RESISTANT ENTEROCOCCI INFECTION OR COLONIZATION" are incorporated by reference herein in their entirety.

Although only exemplary embodiments of the invention are specifically described above, it will be appreciated that modifications and variations of these examples are possible without departing from the spirit and intended scope of the invention. For example, various specific formulations including components not listed herein and specific methods of administering such formulations can be developed using the ordinary skill in the art. In general, all examples and embodiments described herein can be used in combination with one another unless they are clearly mutually exclusive (e.g. a naturally occurring bacteria is, by definition, not a recombinant bacteria).

The invention claimed is:

1. A method of treating a gram-positive bacteria colonization or infection, wherein the method comprises administering to a patient in need of such treatment, a therapeutically effective amount of a pharmaceutical composition comprising an isolated lantibiotic comprising a domain having the amino acid sequence of SEQ ID NO: 3 and a pharmaceutical acceptable carrier.

2. The method of claim 1, wherein the gram-positive bacteria is a vancomycin resistant enterococci (VRE).

3. The method of claim 1, wherein the gram-positive bacteria is *S. aureus, E. faecalis, E. faecium*, or *L. monocytogenes*.

4. The method of claim 1, wherein said treating comprises:
   (a) inhibiting growth of the gram-positive bacteria in the patient,
   (b) killing the gram-positive bacteria in the patient,
   (c) ameliorating at least one symptom of infection with the gram-positive bacteria in the patient; or
   (d) combinations of two or more of (a)-(c).

5. A method for treating a gram-positive bacteria colonization or infection, wherein the method comprises administering to a patient in need of such treatment, a bacterial pharmaceutical composition comprising:
   (a) lantibiotic-producing recombinant bacteria comprising an exogenous nucleic acid comprising the sequence of SEQ ID NO: 5 and operable to produce a lantibiotic having the sequence of SEQ ID NO: 3, wherein the lantibiotic-producing recombinant bacteria are bacteria that do not comprise an endogenous Lan A gene comprising the sequence of SEQ ID NO: 5; and
   (b) a pharmaceutically acceptable carrier.

6. The method of claim 5, wherein the lantibiotic-producing recombinant bacteria further comprise at least one expressible nucleic acid encoding one or more enzymes operable to convert a primary bile acid to a secondary bile acid, the nucleic acid operably linked to a promoter and operable to produce the one or more enzymes operable to convert a primary bile acid to a secondary bile acid.

7. The method of claim 5, wherein the bacterial pharmaceutical composition further comprises at least one supplementary therapeutic bacteria, wherein the supplementary therapeutic bacteria are *Clostridium scindens* (*C. scindens*), *Clostridium hiranonis* (*C. hiranonis*), *Clostridium hylemonae* (*C. hylemonae*) bacteria, a non-lantibiotic producing *B. producta* bacteria, or any combinations thereof.

8. The method of claim 5, wherein the bacterial pharmaceutical composition further comprises at least one supplementary therapeutic bacteria wherein the supplementary therapeutic bacteria are *Parabacteroides distasonis* (*P. distasonis*), *Bacteroides sartorii* (*B. sartorii*), *Clostridium innocuum* (*C. innocuum*), *Akkermansia muciniphila* (*A. muciniphila*), *C. bolteae*, *Blautia* unclassified, *Eubacterium dolichum* (*E. dolichum*), or any combinations thereof.

9. The method of claim 5, wherein the bacterial pharmaceutical composition further comprises a lantibiotic comprising a domain having the amino acid sequence of SEQ ID NO: 3.

10. The method of claim 5, wherein the bacterial pharmaceutical composition further comprises nisin.

11. The method of claim 5, wherein the bacterial pharmaceutical composition further comprises an enzyme operable to convert a primary bile acid to a secondary bile acid.

12. The method of claim 11, wherein the enzyme operable to convert a primary bile acid to a secondary bile acid comprises 7-α-hydroxysteroid dehydrogenase.

13. The method of claim 5, wherein the lantibiotic-producing recombinant bacteria further comprises a second exogenous nucleic acid comprising the sequence of SEQ ID NO: 6, 7, 8, 9, 10, 11, 12, 13 or 14.

14. The method of claim 5, wherein the exogenous nucleic acid further comprises the sequence of SEQ ID NO: 6, 7, 8, 9, 10, 11, 12, 13, 14 or a combination thereof.

15. The method of claim 5, wherein the recombinant bacteria is selected from the group consisting of *Clostridium scindens*, *Bacteroides sartorii*, *Escherichia coli*, *Parabacteroides distasonis*, *Clostridium bolteae*, *Blautia hansenii*, *Pseudoflavonifractor capillosus*, *Clostridium hiranonis*, *Clostridium hylemonae*, *Clostridium perfringens*, *Clostridium sordellii*, *Proteocatella sphenisci*, Lachnospiraceae 5_1_57FAA, Clostridiales VE202-05, Clostridiales VE202-26, *Barnesiella* intestihominis, *Clostridium innocuum*, *Akkermansia muciniphila*, *Blautia* unclassified, *Eubacterium dolichum*, a bacteria of the genus *Lactobacillus*, a bacteria of the genus *Lactococcus*, a bacteria of the genus *Bifidobacterium*, a bacteria of the Firmicutes phylum or a bacteria of the Lachnospiraceae family.

16. A method for treating a gram-positive bacteria colonization or infection, wherein the method comprises administering to a patient in need of such treatment, a bacterial pharmaceutical composition comprising:
   (a) lantibiotic-producing *Blautia producta* bacteria comprising an expressible nucleic acid comprising the sequence of SEQ ID NO: 5 and operable to produce a lantibiotic having the sequence of SEQ ID NO: 3, wherein the lantibiotic-producing *Blautia producta* bacteria are *Blautia producta* bacteria that do not comprise an endogenous Lan A gene comprising the sequence of SEQ ID NO: 5; and
   (b) a pharmaceutically acceptable carrier.

17. The method of claim 16, wherein the bacterial pharmaceutical composition further comprises:
   (i) at least one supplementary therapeutic bacteria, wherein the supplementary therapeutic bacteria are *Clostridium scindens* (*C. scindens*), *Clostridium hiranonis* (*C. hiranonis*), *Clostridium hylemonae* (*C. hylemonae*) bacteria, a non-lantibiotic producing *B. producta* bacteria, or any combinations thereof; or
   (ii) at least one supplementary therapeutic bacteria, wherein the supplementary therapeutic bacteria are *Parabacteroides distasonis* (*P. distasonis*), *Bacteroides sartorii* (*B. sartorii*), *Clostridium innocuum* (*C. innocuum*), *Akkermansia muciniphila* (*A. muciniphila*), *C. bolteae*, *Blautia* unclassified, *Eubacterium dolichum* (*E. dolichum*), or any combinations thereof.

18. The method of claim 16, wherein the bacterial pharmaceutical composition further comprises a lantibiotic comprising a domain having the amino acid sequence of SEQ ID NO: 3, nisin or both.

19. The method of claim 1, wherein the lantibiotic comprising the domain having the amino acid sequence of SEQ ID NO: 3 is purified.

20. The method of claim 1, wherein the pharmaceutical composition consists essentially of the isolated lantibiotic comprising the domain having the amino acid sequence of SEQ ID NO: 3 and the pharmaceutical acceptable carrier.

* * * * *